US012577197B2

(12) United States Patent
Aerni et al.

(10) Patent No.: US 12,577,197 B2
(45) Date of Patent: Mar. 17, 2026

(54) METHODS OF PREPARING $N^6$-((2-AZIDOETHOXY)CARBONYL)LYSINE

(71) Applicant: SANOFI, Paris (FR)

(72) Inventors: Hans Aerni, San Diego, CA (US); Randall Scheuerman, Santa Clara, CA (US); Nikolai F. Sepetov, Santa Clara, CA (US); Alexander V. Shirokov, Santa Clara, CA (US)

(73) Assignee: SANOFI, Paris (FR)

( * ) Notice: Subject to any disclaimer, the term of this patent is extended or adjusted under 35 U.S.C. 154(b) by 714 days.

(21) Appl. No.: 17/845,495

(22) Filed: Jun. 21, 2022

(65) Prior Publication Data

US 2022/0324792 A1 Oct. 13, 2022

Related U.S. Application Data

(63) Continuation of application No. PCT/US2020/066692, filed on Dec. 22, 2020.

(60) Provisional application No. 62/953,089, filed on Dec. 23, 2019.

(51) Int. Cl.
*C07C 247/22* (2006.01)
*C07D 207/404* (2006.01)

(52) U.S. Cl.
CPC ........ *C07C 247/22* (2013.01); *C07D 207/404* (2013.01)

(58) Field of Classification Search
CPC .......................... C07C 247/22; C07D 207/404
See application file for complete search history.

(56) References Cited

U.S. PATENT DOCUMENTS

| | | | | |
|---|---|---|---|---|
| 10,610,571 | B2 | 4/2020 | Ptacin et al. | |
| 11,077,195 | B2 | 8/2021 | Ptacin et al. | |
| 11,622,993 | B2 | 4/2023 | Ptacin et al. | |
| 11,701,407 | B2 | 7/2023 | Ptacin et al. | |
| 12,377,131 | B2 | 8/2025 | Caffaro et al. | |
| 2002/0028806 | A1* | 3/2002 | Goebel .................. | A01N 47/16 548/326.5 |
| 2012/0315245 | A1 | 12/2012 | Leon et al. | |
| 2016/0297855 | A1 | 10/2016 | Zhou et al. | |
| 2020/0188484 | A1 | 6/2020 | Ptacin et al. | |
| 2020/0231644 | A1 | 7/2020 | Ptacin et al. | |
| 2020/0368293 | A1 | 11/2020 | Olle | |
| 2020/0399338 | A1 | 12/2020 | Caffaro et al. | |
| 2021/0046160 | A1 | 2/2021 | Ptacin et al. | |
| 2021/0054040 | A1 | 2/2021 | Caffaro et al. | |
| 2021/0070827 | A1 | 3/2021 | Ptacin et al. | |
| 2021/0299222 | A1 | 9/2021 | Rodriguez et al. | |
| 2021/0338829 | A1 | 11/2021 | Caffaro et al. | |
| 2022/0016249 | A1 | 1/2022 | Ptacin et al. | |
| 2022/0016252 | A1 | 1/2022 | Abbadessa et al. | |
| 2022/0273767 | A1 | 9/2022 | Caffaro et al. | |
| 2023/0265148 | A1 | 8/2023 | Hu et al. | |
| 2023/0277627 | A1 | 9/2023 | Caffaro et al. | |
| 2023/0416327 | A1 | 12/2023 | Caffaro et al. | |
| 2024/0082359 | A1 | 3/2024 | Ptacin et al. | |
| 2024/0226309 | A1 | 7/2024 | Abbadessa et al. | |
| 2024/0287151 | A1 | 8/2024 | Caffaro et al. | |
| 2024/0383957 | A1 | 11/2024 | Caffaro et al. | |

FOREIGN PATENT DOCUMENTS

| | | | |
|---|---|---|---|
| CN | 102665754 | A | 9/2012 |
| CN | 104231068 | A | 12/2014 |
| CN | 108997168 | A | 12/2018 |
| EP | 4011388 | A1 | 6/2022 |
| EP | 4209503 | A1 | 7/2023 |
| WO | 2012019299 | A1 | 2/2012 |
| WO | 2019028419 | A1 | 2/2019 |
| WO | 2019028425 | A1 | 2/2019 |
| WO | 2019165453 | A1 | 8/2019 |
| WO | 2019173832 | A2 | 9/2019 |
| WO | 2020097325 | A1 | 5/2020 |
| WO | 2020163532 | A1 | 8/2020 |
| WO | 2021030706 | A1 | 2/2021 |
| WO | 2021041206 | A1 | 3/2021 |
| WO | 2021050554 | A1 | 3/2021 |
| WO | 2021091986 | A1 | 5/2021 |
| WO | 2021133839 | A1 | 7/2021 |
| WO | 2021263026 | A1 | 12/2021 |
| WO | 2022076853 | A1 | 4/2022 |
| WO | 2022076859 | A1 | 4/2022 |
| WO | 2022174101 | A1 | 8/2022 |

(Continued)

OTHER PUBLICATIONS

Emerson et al., "NMR Characterization of Interleukin-2 in Complexes with the IL-2R Receptor Component, and with Low Molecular Weight Compounds that Inhibit the IL-2/IL-R interaction", Protein Science, vol. 12 (Dec. 31, 2003).
Ghelani et al., "Defining the Threshold IL-2 Signal Required for Induction of Selective Treg Cell Responses Using Engineered IL-2 Muteins", Frontiers in Immunology, vol. 11, Article 1106, figure 2, (Jun. 30, 2020).
Levin et al., "Exploiting a Natural Conformational Switch to Engineer an Interleukin-2 Superkine", Nature, vol. 484, No. 7359, (Apr. 26, 2012).
Mei et al., "Site-Mutation of Hydrophobic Core Residues Synchronically Poise Super Interleukin 2 for Signaling: Identifying Distant Structural Effects through Affordable Computations", International Journal of Molecular Science, vol. 19, No. 3, Article 916 (Mar. 20, 2018).

(Continued)

*Primary Examiner* — Joseph K McKane
*Assistant Examiner* — Jalisa Holmes Ferguson
(74) *Attorney, Agent, or Firm* — McNeill PLLC

(57) ABSTRACT

Disclosed herein are methods of preparing $N^6$-((2-azidoethoxy)carbonyl)lysine, $N^6$-((2-azidoethoxy)carbonyl)-L-lysine, and $N^6$-((2-azidoethoxy)carbonyl)-D-lysine. Also disclosed herein are the compounds tert-butyl $N^2$-(tert-butoxycarbonyl)-$N^6$-((2-chloroethoxy)carbonyl)-L-lysinate and tert-butyl $N^6$-((2-azidoethoxy)carbonyl)-$N^2$-(tert-butoxycarbonyl)-L-lysinate, and uses thereof.

30 Claims, 5 Drawing Sheets

(56) References Cited

FOREIGN PATENT DOCUMENTS

| | | | |
|---|---|---|---|
| WO | 2022256538 | A1 | 12/2022 |
| WO | 2023122750 | A1 | 6/2023 |
| WO | 2023137401 | A1 | 7/2023 |
| WO | 2024136899 | A1 | 6/2024 |

OTHER PUBLICATIONS

Prometheus Laboratories Inc., FDA Label for Proleukin (Aldesleukin), 19 pages (2011).

Ptacin et al., "A CD25-biased interleukin-2 for autoimmune therapy engineered via a semi-synthetic organism", Communications Medicine, 4:58, pp. 1-16, (2024).

Rao et al., "Interleukin-2 Mutants with Enhanced A-Receptor Subunit Binding Affinity", Protein Engineering, vol. 16, No. 12, (Dec. 31, 2003).

International Search Report and Written Opinion issued for PCT/US2020/066692, Apr. 22, 2021, 18 pages.

Apatsanis et al., "Synthesis of N-2,2,2-(Trichloroethoxycarbonyl)-L-amino Acids and N-(9-Fluorenylmethoxycarbonyl)-L-amino Acids Involving Succinimidoxy Anion as a Leaving Group in Amino Acid Protection", Synthesis, vol. 8, Jan. 1, 1983, pp. 671-673.

Milles et al., "Click Strategies for Single-Molecule Protein Fluorescence", Journal of the American Chemical Society, vol. 134, No. 11, Mar. 5, 2012, pp. 5187-5195.

Yanagisawa et al., "Structural Basis for Genetic-Code Expansion with Bulky Lysine Derivatives by an Engineered Pyrrolysyl-tRNA Synthetase", Cell Chemical Biology, vol. 26, No. 7, Apr. 25, 2019, pp. 936-949.

Abbadessa et al., Co-pending U.S. Appl. No. 17/357,615, filed Jun. 24, 2021.

Caffaro et al., Co-pending U.S. Appl. No. 16/999,638, filed Aug. 21, 2020; also cited herein as US 2021/0054040.

Caffaro et al., Co-pending U.S. Appl. No. 17/001,965, filed Aug. 25, 2020; also cited herein as US 2020/0399338.

Caffaro et al., Co-pending U.S. Appl. No. 17/313,579, filed May 6, 2021; also cited herein as US 2021/0338829.

Caffaro et al., Co-pending U.S. Appl. No. 17/735,564, filed May 3, 2022.

Grimshaw et al., Journal of the Chemical Society, pp. 7136-7139 (1965).

Ptacin et al., Co-pending U.S. Appl. No. 16/634,487, filed Jan. 27, 2020; also cited herein as US 2020/0231644.

Ptacin et al., Co-pending U.S. Appl. No. 16/803,816, filed Feb. 27, 2020; also cited herein as US 2020/0188484.

Ptacin et al., Co-pending U.S. Appl. No. 16/993,967, filed Aug. 14, 2020; also cited herein as US 2021/0046160.

Ptacin et al., Co-pending U.S. Appl. No. 17/016,003, filed Sep. 9, 2020; also cited herein as US 2021/0070827.

Ptacin et al., Co-pending U.S. Appl. No. 17/350,672, filed Jun. 17, 2021.

Ptacin et al., Co-pending U.S. Appl. No. 16/993,967, filed Aug. 14, 2020; previously cited as US Publication No. 20210046160.

Caffaro et al., Co-pending U.S. Appl. No. 16/999,638, filed Aug. 21, 2020; previously cited as US Publication No. 20210054040.

Caffaro et al., Co-pending U.S. Appl. No. 17/001,965, filed Aug. 25, 2020; previously cited as US Publication No. 20200399338.

Ptacin et al., Co-pending U.S. Appl. No. 17/016,003, filed Sep. 9, 2020; previously cited as US Publication No. 20210070827.

Caffaro et al., Co-pending U.S. Appl. No. 17/313,579, filed May 6, 2021; previously cited as US Publication No. 2021/0338829.

Ptacin et al., Co-pending U.S. Appl. No. 17/350,672, filed Jun. 17, 2021; previously cited as US Publication No. 20220016249.

Abbadessa et al., Co-pending U.S. Appl. No. 17/357,615, filed Jun. 24, 2021; also cited herein as US Publication No. 20220016252.

Caffaro et al., Co-pending U.S. Appl. No. 17/735,564, filed May 3, 2022; also cited herein as US Publication No. 20220273767.

Caffaro et al., Co-pending U.S. Appl. No. 18/296,710, filed Apr. 6, 2023; also cited herein as US Publication No. 20230277627.

Caffaro et al., Co-pending U.S. Appl. No. 18/296,711, filed Apr. 6, 2023; also cited herein as US Publication No. 20230416327.

Ptacin et al., Co-pending U.S. Appl. No. 18/327,535, filed Jun. 1, 2023; also cited herein as US Publication No. U.S. Appl. No. 18/327,535, filed Jun. 1, 2023.

Caffaro et al., Co-pending U.S. Appl. No. 18/415,445, filed Jan. 17, 2024; also cited herein as US Publication No. 20240287151.

Caffaro et al., Co-pending U.S. Appl. No. 18/424,573, filed Jan. 26, 2024; also cited herein as US Publication No. 20240383957.

Abbadessa et al., Co-pending U.S. Appl. No. 18/524,157, filed on Nov. 30, 2023; also cited herein as US Publication No. 20240226309.

Ptacin et al., Co-pending U.S. Appl. No. 18/886,814, filed Sep. 16, 2024.

Ptacin et al., Co-pending U.S. Appl. No. 19/025,471, filed Jan. 16, 2025.

Caffaro et al., Co-pending U.S. Appl. No. 19/257,936, filed Jul. 2, 2025.

* cited by examiner

METHODS OF PREPARING N$^6$-((2-AZIDOETHOXY)CARBONYL)LYSINE

CROSS-REFERENCE TO RELATED APPLICATIONS

This application is a continuation of International Application No. PCT/US2020/066692, filed on Dec. 22, 2020, which claims priority to U.S. Provisional Application No. 62/953,089, filed on Dec. 23, 2019, the disclosure of each of which is hereby incorporated by reference in its entirety.

BACKGROUND OF THE DISCLOSURE

The compound N$^6$-((2-azidoethoxy)carbonyl)lysine and the two enantiomers, azidoethoxy)carbonyl)-L-lysine and N$^6$-((2-azidoethoxy)carbonyl)-D-lysine, are useful in the preparation of polypeptides and proteins as research tools and therapeutic products. For example, it has been demonstrated that an orthogonal *Methanosarcina barkeri* MS pyrrolysyl-tRNA synthetase/tRNA pair can direct the efficient, site-specific incorporation of N$^6$-((2-azidoethoxy)carbonyl)-L-lysine into recombinant proteins in *Escherichia coli.* Proteins containing the azide function group can be coupled via [3+2] cycloaddition reactions to attach fluorescent labels and other functional moieties to the proteins. Prior methods for the preparation of N$^6$-((2-azidoethoxy)carbonyl)lysine, including the two enantiomers, provide poor yields or rely on chemical intermediates that may present a significant safety hazard (Milles, S. et al., *J. Am. Chem. Soc.* (2012), Vol. 134, 5187-5195; US 2016/0297855). Therefore, there is a need for a reproducible, high-yielding process for the preparation of these compounds that relies on the preparation of chemical intermediates that may present a lessened safety hazard.

SUMMARY OF THE DISCLOSURE

Described herein, in certain embodiments, are methods for preparing N$^6$-((2-azidoethoxy)carbonyl)lysine and intermediates useful therein.

The following embodiments are encompassed.

Embodiment 1 is a method of preparing a compound of Formula (VI)

(VI)

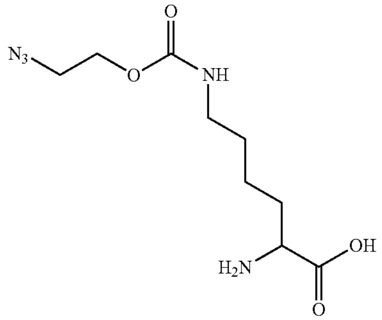

or a salt thereof, comprising reacting a compound of Formula (III)

(III)

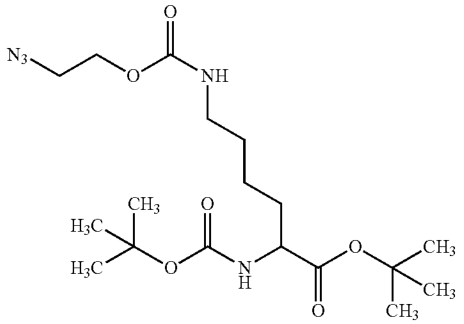

with an acid to afford the compound of Formula (VI) or a salt thereof.

Embodiment 2 is the method of embodiment 1, wherein the acid is one or more of phosphoric acid, hydrochloric acid, acetic acid, and trifluoroacetic acid.

Embodiment 3 is the method of embodiment 1 or 2, wherein the acid is hydrochloric acid.

Embodiment 4 is the method of any one of embodiments 1-3, wherein the reaction of the compound of Formula (III) with the acid is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment 5 is the method of embodiment 4, wherein the aprotic solvent is 1,4-dioxane.

Embodiment 6 is the method of any one of embodiments 1-5, wherein the method further comprises addition of a base.

Embodiment 7 is the method of embodiment 6, wherein the base is one or more of ammonium hydroxide, sodium hydroxide, or potassium hydroxide.

Embodiment 8 is the method of embodiment 6 or 7, wherein the base is ammonium hydroxide.

Embodiment 9 is the method of any one of embodiments 6-8, wherein addition of the base provides a solution having a pH in a range from 4 to 10.

Embodiment 10 is the method of any one of embodiments 6-9, wherein addition of the base provides a solution having a pH in a range from 8 to 9.

Embodiment 11 is the method of any one of embodiments 1-10, wherein the compound of Formula (VI) is a compound of Formula (VIa)

(VIa)

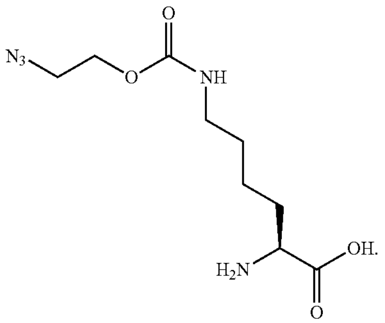

Embodiment 12 is a method of preparing a compound of Formula (III)

III

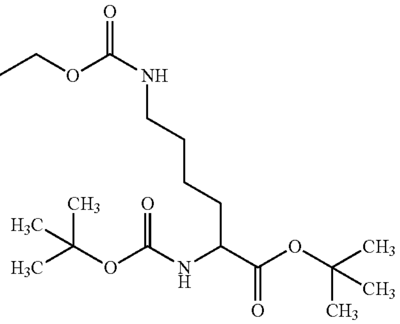

comprising reacting a compound of Formula (II)

(II)

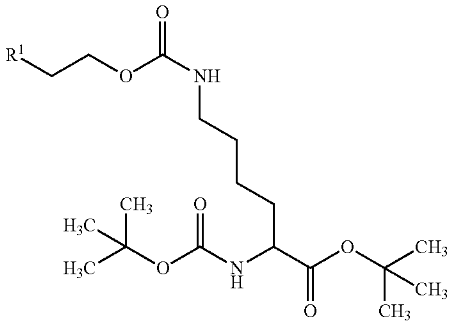

wherein $R^1$ is selected from chloro, bromo, and iodo, with an alkali azide salt to afford the compound of Formula (III).

Embodiment 13 is the method of embodiment 12, wherein $R^1$ is chloro.

Embodiment 14 is the method of embodiment 12 or 13, wherein the alkali azide salt is selected from lithium azide, sodium azide, and potassium azide.

Embodiment 15 is the method of any one of embodiments 12-14, wherein the alkali azide salt is sodium azide.

Embodiment 16 is the method of any one of embodiments 12-15, wherein the reaction of the compound of Formula (II) with the alkali azide salt is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400, polyethylene glycols.

Embodiment 17 is the method of embodiment 16, wherein the aprotic solvent is acetonitrile.

Embodiment 18 is the method of embodiment 16 or 17, wherein the solution further comprises water.

Embodiment 19 is the method of any one of embodiments 12-18, wherein the compound of Formula (III) is a compound of Formula (IIIa)

(IIIa)

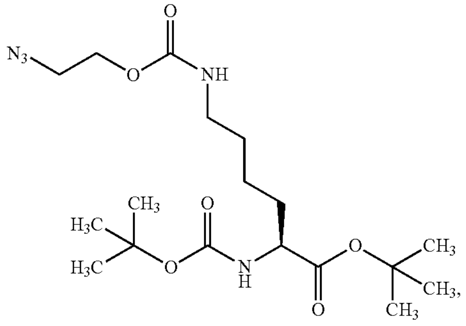

and the compound of Formula (II) is a compound of Formula (IIa)

(IIa)

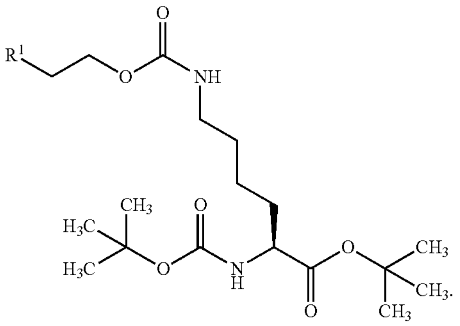

Embodiment 20 is a method of preparing a compound of Formula (II)

(II)

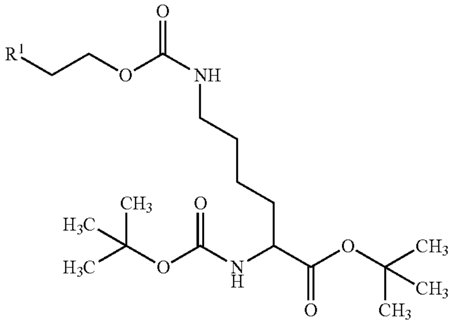

comprising reacting a compound of Formula (I)

(I)

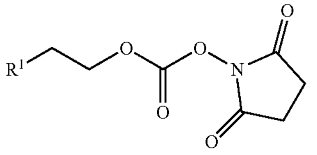

with a compound of Formula (V)

(V)

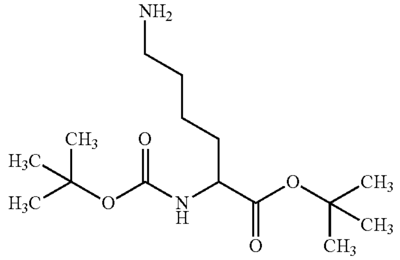

to afford the compound of Formula (II), wherein in each of the compounds of Formula (I) and Formula (II), $R^1$ is the same and is selected from chloro, bromo and iodo.

Embodiment 21 is the method of embodiment 20, wherein $R^1$ in each of the compounds of Formula (I) and Formula (II) is chloro.

Embodiment 22 is the method of embodiment 20 or 21, wherein the reaction of the compound of Formula (V) with the compound of Formula (I) is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment 23 is the method of embodiment 22, wherein the aprotic solvent is 2-methyltetrahydrofuran or N,N-dimethylformamide.

Embodiment 24 is the method of any one of embodiments 20-23, wherein the compound of Formula (II) is a compound of Formula (IIa)

(IIa)

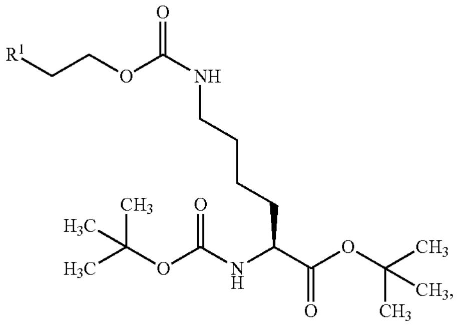

and the compound of Formula (V) is a compound of Formula (Va)

(Va)

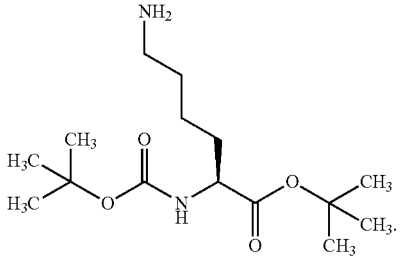

Embodiment 25 is a method of preparing a compound of Formula (I)

(I)

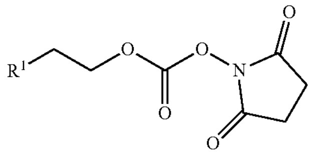

comprising reacting a compound of Formula (IV)

(IV)

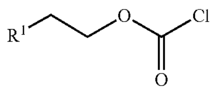

with N-hydroxysuccinimide to afford the compound of Formula (I), wherein in each of the compounds of Formula (I) and Formula (IV), $R^1$ is the same and is selected from chloro, bromo, and iodo.

Embodiment 26 is the method of embodiment 25, wherein $R^1$ is chloro.

Embodiment 27 is the method of embodiment 25 or 26, wherein the reaction of the compound of Formula (IV) with N-hydroxysuccinimide is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment 28 is the method of embodiment 27, wherein the aprotic solvent is acetonitrile or 2-methyltetrahydrofuran.

Embodiment 29 is the method of embodiment 27 or 28, wherein the solution further comprises a base.

Embodiment 30 is the method of embodiment 29, wherein the base is a trialkylamine.

Embodiment 31 is the method of embodiment 29 or 30, wherein the base is triethylamine.

Embodiment 32 is a method of preparing a compound of Formula (VIa), or a salt thereof, comprising the following steps:

(i) reacting
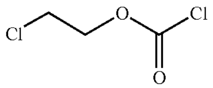
with
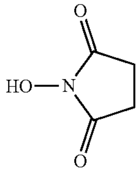
to form
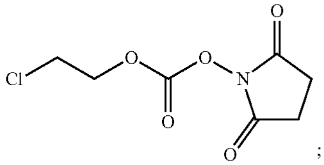 [SMILES: O=C(OCCCl)ON1C(=O)CCC1=O]
;
(ii) reacting
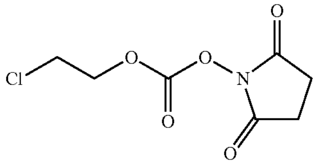 [SMILES: O=C(OCCCl)ON1C(=O)CCC1=O]
with
(Va)
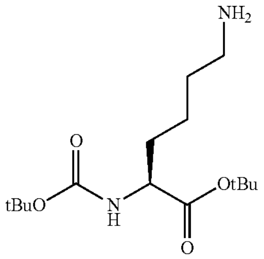
to form
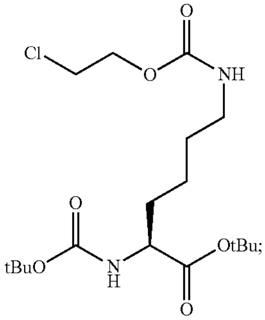 [SMILES: CC(C)(C)OC(=O)N[C@@H](CCCCNC(=O)OCCCl)C(=O)OC(C)(C)C]
(iii) reacting
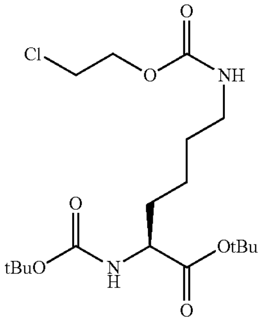 [SMILES: CC(C)(C)OC(=O)N[C@@H](CCCCNC(=O)OCCCl)C(=O)OC(C)(C)C]
with $NaN_3$ to form
(IIIa)
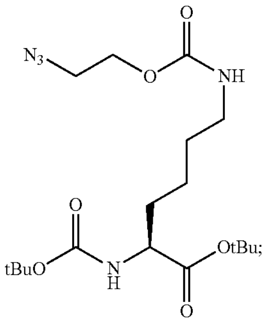
and
(iv) reacting
(IIIa)
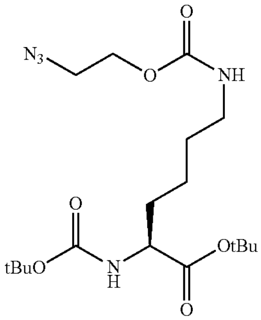

with HCl to form (VIa)

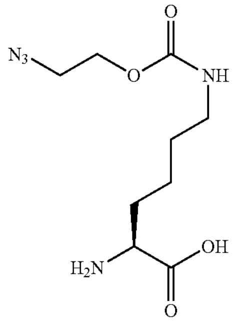

or a salt thereof.

Embodiment 33 is a compound of Formula (I):

(I)

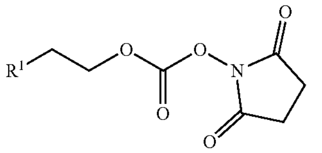

wherein $R^1$ is selected from chloro, bromo, and iodo.

Embodiment 34 is the compound of embodiment 33, wherein $R^1$ is chloro.

Embodiment 35 is a compound of Formula (II):

(II)

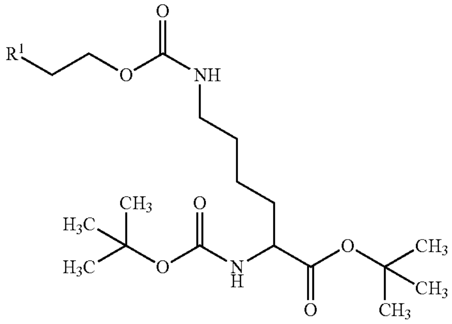

wherein $R^1$ is selected from chloro, bromo, and iodo.

Embodiment 36 is the compound of embodiment 35, wherein $R^1$ is chloro.

Embodiment 37 is the compound of embodiment 35 or 36, wherein the compound of Formula (II) is a compound of Formula (IIa):

(IIa)

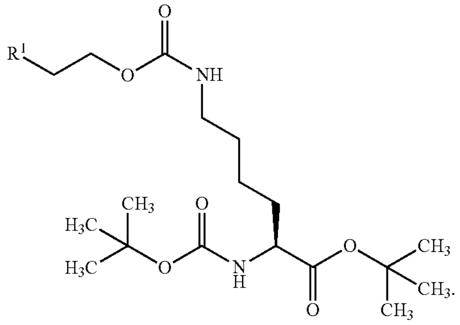

Embodiment 38 is a compound of Formula (III):

(III)

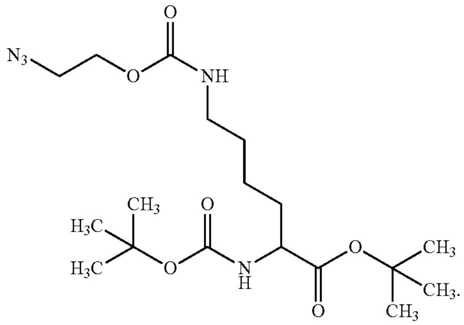

Embodiment 39 is the compound of embodiment 38, wherein the compound of Formula (III) is a compound of Formula (IIIa):

(IIIa)

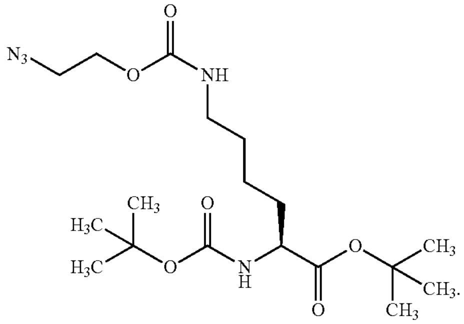

Embodiment 40 is a compound of Formula (VII):

(VII)

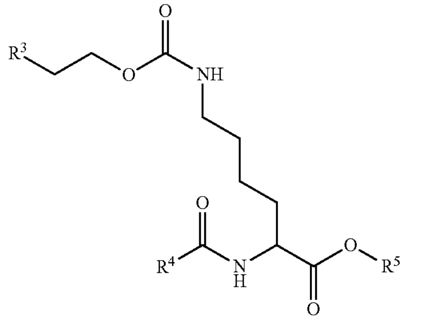

wherein:

$R^3$ is selected from chloro, bromo and iodo;

$R^4$ is selected from —$OR^6$, —$CF_3$, —$CH_2C_6$-$C_{12}$aryl, and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$ aryl.

Embodiment 41 is a compound of Formula (VIII):

(VIII)

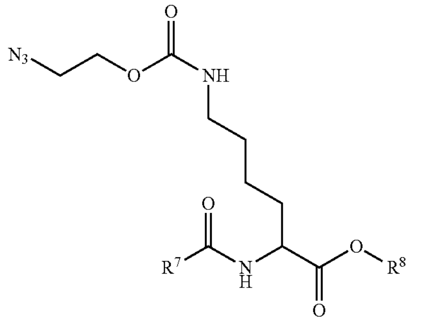

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE DISCLOSURE

Definitions

Figure 1:
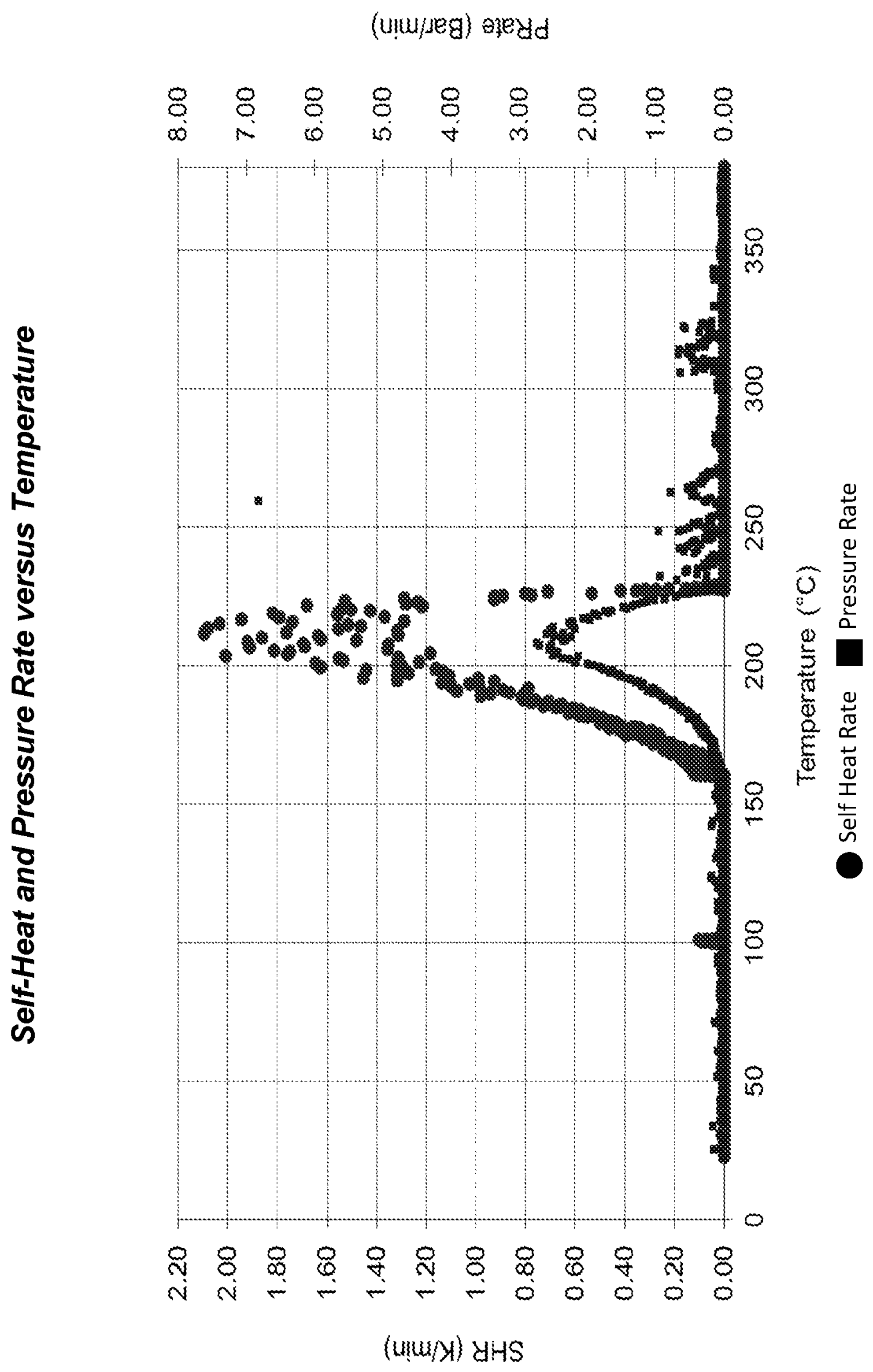
FIG. 1 shows plots of self-heat and pressure versus temperature of $N^6$-((2-azidoethoxy)carbonyl)-$N^2$-(tert-butoxycarbonyl)-L-lysinate (Formula (IIIa) for the ARC study described in Example 10.

Unless defined otherwise, all technical and scientific terms used herein have the same meaning as is commonly understood by one of skill in the art to which the claimed subject matter belongs. It is to be understood that the detailed descriptions are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the present disclosure.

As used herein, ranges and amounts can be expressed as "about" a particular value or range. About also includes the exact amount. Hence "about 0° C." means "about 0° C." and also "0° C." Generally, the term "about" includes an amount that would be expected to be within experimental error, such as for example, within 15%, 10%, or 5%.

The section headings used herein are for organizational purposes only and are not to be construed as limiting the subject matter described.

The term "$C_1$-$C_6$ alkyl", as used herein, means an acyclic, saturated hydrocarbon group of the formula $C_nH_{2n+1}$ having from 1 to 6 carbon atoms and which may be linear or branched. Examples of such groups include, but are not limited to, methyl, ethyl, n-propyl, isopropyl, n-butyl, isobutyl, sec-butyl, tert-butyl, pentyl, iso-amyl and hexyl.

The term "$C_6$-$C_{12}$aryl," as used herein, means an aromatic monocyclic or bicyclic hydrocarbon containing six to 12 ring carbon atoms which may be attached via one of the ring carbon atoms. When the $C_6$-$C_{12}$aryl is substituted, the substituent may be located on a ring carbon atom. Specific examples include, but are not limited to, phenyl, tolyl, xylyl, trimethylphenyl, and naphthyl. Examples of aryl substituents include, but are not limited to, alkyl, hydroxyl, halo, nitrile, alkoxy, trifluoromethyl, carboxamido, $SO_2CH_3$, benzyl, and substituted benzyl.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Compounds and Methods of Preparation

Compounds of Formula (I)

Described herein are compounds of Formula (I), (I)

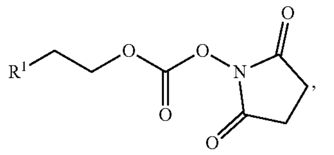

wherein $R^1$ is selected from chloro, bromo and iodo. In some embodiments, $R^1$ is chloro. In some embodiments, $R^1$ is bromo. In some embodiments, $R^1$ is iodo.

The C—$R^1$ bond, wherein $R^1$ is chloro, bromo, or iodo, of the compound of Formula (I) is of sufficient reactivity to allow further reaction, for example with a compound of Formula (V). In some embodiments, the compound of Formula (I) is more reactive than the fluoro analog

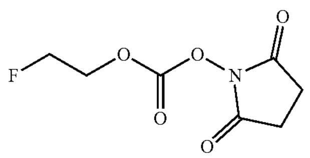 [SMILES: O=C(OCCF)ON1C(=O)CCC1=O]

(WO2012/019299), such as with a compound of Formula (V) to form a compound of Formula (II). In some embodiments, the reaction rate of the compound of Formula (I) with a compound of Formula (V) to form a compound of Formula (II) is faster than the reaction rate of the corresponding fluoro analog. In some embodiments, the reaction rate of the compound of Formula (I) with a compound of Formula (V) to form a compound of Formula (II) is more useful for chemical synthesis than the reaction rate using the corresponding fluoro analog.

The compounds of Formula (I) may be prepared using starting materials that are commercially available or are readily available by methods known to those of ordinary skill in the art. For example, the compound of Formula (I) wherein $R^1$ is chloro may be prepared by allowing 2-chloroethyl chloroformate to react with N-hydroxysuccinimide, both of which are commercially available, or may be prepared by methods known to those of ordinary skill in the art. The reaction of 2-chloroethyl chloroformate with N-hydroxysuccinimide may be conducted in a solution comprising an aprotic solvent such as acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent that may be used is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane. In other embodiments, the aprotic solvent is selected from acetonitrile, acetone, methyl ethyl ketone, dichloromethane, chloroform, tetrahydrofuran, and N,N-dimethylformamide. In still further embodiments, the aprotic solvent is acetonitrile, acetone, methyl ethyl ketone, dichloromethane, chloroform, or tetrahydrofuran. In some embodiments, the aprotic solvent that may be used is 2-methyltetrahydrofuran. The solution in which the 2-haloethyl chloroformate is allowed to react with N-hydroxysuccinimide may further comprise a base, which may comprise an organic base or an inorganic base, or both an organic base and an inorganic base. In some cases, the organic base used may be selected from a heterocyclic base and a trialkylamine, or a mixture thereof. Further, if a heterocyclic base is used, it may be selected from an aromatic heterocyclic base or a non-aromatic heterocyclic base, or a mixture of an aromatic heterocyclic base and a non-aromatic heterocyclic base. Examples of aromatic heterocyclic bases include, but are not limited to, pyridine, 1-alkylpyrrole, and 1-alkylimidazole, or a mixture thereof. Further examples aromatic heterocyclic bases that may be used include pyridine, 1-methylpyrrole, and 1-methylimidazole, or a mixture thereof. In some cases, the heterocyclic base used may be a non-aromatic heterocyclic base, including, but not limited to, an N-alkylpyrrolidine, an N-alkylpiperidine, an N-alkylmorpholine, and a 1,4-dialkylpiperazine, or a mixture thereof. Further examples of non-aromatic heterocyclic bases that may be used include, but are not limited to, N-methylpyrrolidine, N-methylpiperidine, and N-methylmorpholine. In other cases, one of ordinary skill in the art may use a base which is a trialkylamine, examples of which include, but are not limited to, trimethylamine, triethylamine, tri-n-propylamine, tri-n-butylamine, tripentylamine, trihexylamine, and diisopropylethylamine. In some embodiments, the base is triethylamine. The reaction of a 2-haloethyl chloroformate compound with N-hydroxysuccinimide may be further conducted at a temperature in the range from about −25° C. to about 100° C., or at a range from about 0° C. to about room temperature. In some embodiments, the reaction is conducted at a temperature of about 0° C. In the above embodiments and any embodiments described herein where an aprotic solvent is used, the reaction solvent may be substantially free or free of protic solvents. "Substantially free" means that the referenced substance is absent or is present in a sufficiently low quantity to have a negligible impact on the reaction (e.g., an effect of less than 15%, 10%, or 5% on the yield of the reaction).

An example of the method that may be used to prepare a compound of Formula (I), wherein $R^1$ is chloro, is shown below in Scheme 1.

Scheme 1.

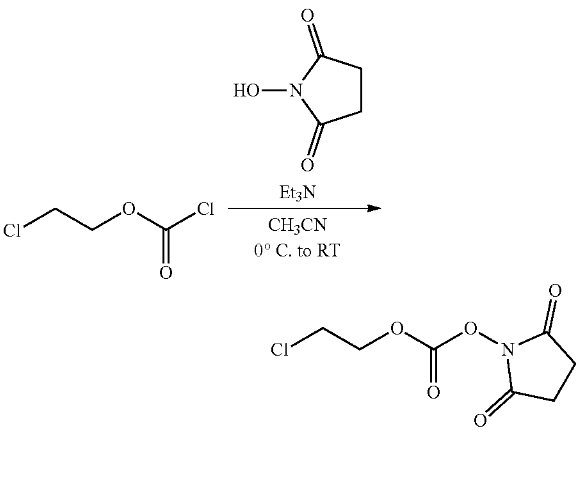

Similar methods may be used to prepare the compounds of Formula (I) wherein $R^1$ is bromo or iodo using 2-bromoethyl chloroformate or 2-iodomethyl chloroformate, respectively. The compound 2-bromoethyl chloroformate is commercially available or may be prepared by methods known to those having ordinary skill in the art. The preparation of 2-iodomethyl chloroformate is described in Grimshaw et al., *Journal of the Chemical Society,* 1965, pp. 7136-9.

In one aspect, provided herein are methods of preparing a compound of Formula (I), (I)

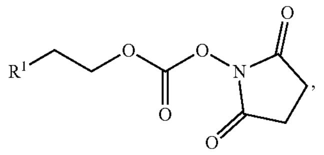

comprising allowing a compound of formula (IV), (IV)

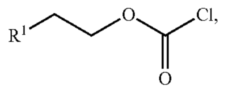

to react with N-hydroxysuccinimide to afford the compound of Formula (I), wherein, in each of the compounds of Formula (I) and (IV), $R^1$ is the same and is selected from chloro, bromo, and iodo. In some embodiments of the methods, $R^1$ is chloro. In some embodiments of the methods, $R^1$ is bromo. In some embodiments of the methods, $R^1$ is iodo.

In some embodiments of the methods of preparing the compound of Formula (I) disclosed herein, the reaction of the compound of Formula (IV) with N-hydroxysuccinimide is performed in a solution comprising an aprotic solvent. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane. In some embodiments, the aprotic solvent is selected from acetonitrile, acetone, methyl ethyl ketone, dichloromethane, chloroform, tetrahydrofuran, and N,N-dimethylformamide. In some embodiments, the aprotic solvent is acetonitrile. In some embodiments, the aprotic solvent is acetone. In some embodiments, the aprotic solvent is methyl ethyl ketone. In some embodiments, the aprotic solvent is dichloromethane. In some embodiments, the aprotic solvent is chloroform. In some embodiments, the aprotic solvent is tetrahydrofuran. In some embodiments, the aprotic solvent is 2-methyltetrahydrofuran. In some embodiments, the aprotic solvent is N,N-dimethylformamide.

In some embodiments, the solution further comprises a base. In some embodiments, the base is selected from an organic base and an inorganic base. In some embodiments, the organic base is selected from a heterocyclic base and a trialkylamine, or a mixture thereof. In some embodiments, the heterocyclic base is an aromatic heterocyclic base or a non-aromatic heterocyclic base, or a mixture of an aromatic heterocyclic base and a non-aromatic heterocyclic base. In some embodiments, the heterocyclic base is an aromatic heterocyclic base. In some embodiments, the aromatic heterocyclic base is selected from pyridine, 1-alkylpyrrole, and 1-alkylimidazole, or a mixture thereof. In some embodiments, the aromatic heterocyclic base is selected from pyridine, 1-methylpyrrole, and 1-methylimidazole, or a mixture thereof. In some embodiments, the aromatic heterocyclic base is pyridine. In some embodiments, the aromatic heterocyclic base is 1-methylpyrrole. In some embodiments, the aromatic heterocyclic base is 1-methylimidazole. In some embodiments, the heterocyclic base is a non-aromatic heterocyclic base. In some embodiments, the non-aromatic heterocyclic base is selected from an N-alkylpyrrolidine, an N-alkylpiperidine, an N-alkylmorpholine, and a 1,4-dialkylpiperazine, or a mixture thereof. In some embodiments, the non-aromatic heterocyclic base is an N-alkylpyrrolidine. In some embodiments, the non-aromatic heterocyclic base is an N-alkylpiperidine. In some embodiments, the non-aromatic heterocyclic base is an N-alkylmorpholine. In some embodiments, the non-aromatic heterocyclic base is a 1,4-dialkylpiperazine. In some embodiments, the non-aromatic heterocyclic base is selected from N-methylpyrrolidine, N-methylpiperidine, and N-methylmorpholine. In some embodiments, the non-aromatic heterocyclic base is N-methylpyrrolidine. In some embodiments, the non-aromatic heterocyclic base is N-methylpiperidine. In some embodiments, the non-aromatic heterocyclic base is N-methylmorpholine. In some embodiments, the organic base is a trialkylamine. In some embodiments, the trialkylamine is selected from trimethylamine, triethylamine, tri-n-propylamine, tri-n-butylamine, tripentylamine, trihexylamine, and diisopropylethylamine. In some embodiments, the trialkylamine is selected from trimethylamine, triethylamine, tri-n-propylamine, and diisopropylethylamine. In some embodiments, the trialkylamine is selected from triethylamine, tri-n-propylamine, and diisopropylethylamine. In some embodiments, the trialkylamine is triethylamine or diisopropylethylamine. In some embodiments, the trialkylamine is triethylamine. In some embodiments, the trialkylamine is diisopropylethylamine.

In some embodiments of the methods of preparing the compound of Formula (I) disclosed herein, $R^1$ in the compound of Formula (I) is chloro and the aprotic solvent is acetonitrile. In some embodiments, the solution further comprises a base. In some embodiments, the base is selected from a trialkylamine. In some embodiments, the trialkylamine is selected from trimethylamine, triethylamine, tri-n-propylamine, tri-n-butylamine, tripentylamine, trihexylamine, and diisopropylethylamine. In some embodiments, the trialkylamine is selected from trimethylamine, triethylamine, tri-n-propylamine, and diisopropylethylamine. In some embodiments, the trialkylamine is selected from triethylamine, tri-n-propylamine, and diisopropylethylamine. In some embodiments, the trialkylamine is triethylamine or diisopropylethylamine. In some embodiments, the trialkylamine is triethylamine. In some embodiments, the trialkylamine is diisopropylethylamine.

In some embodiments of the methods of preparing the compound of Formula (I) disclosed herein, $R^1$ in the compound of Formula (I) is bromo and the aprotic solvent is acetonitrile. In some embodiments, the solution further comprises a base. In some embodiments, the base is selected from a trialkylamine. In some embodiments, the trialkylamine is selected from trimethylamine, triethylamine, tri-n-propylamine, tri-n-butylamine, tripentylamine, trihexylamine, and diisopropylethylamine. In some embodiments, the trialkylamine is selected from trimethylamine, triethylamine, tri-n-propylamine, and diisopropylethylamine. In some embodiments, the trialkylamine is selected from triethylamine, tri-n-propylamine, and diisopropylethylamine. In some embodiments, the trialkylamine is triethylamine or diisopropylethylamine. In some embodiments, the trialkylamine is triethylamine. In some embodiments, the trialkylamine is diisopropylethylamine.

In some embodiments of the methods of preparing the compound of Formula (I) disclosed herein, $R^1$ in the compound of Formula (I) is iodo and the aprotic solvent is acetonitrile. In some embodiments, the solution further comprises a base. In some embodiments, the base is selected from a trialkylamine. In some embodiments, the trialkylamine is selected from trimethylamine, triethylamine, tri-n-propylamine, tri-n-butylamine, tripentylamine, trihexylamine, and diisopropylethylamine. In some embodiments, the trialkylamine is selected from trimethylamine, triethylamine, tri-n-propylamine, and diisopropylethylamine. In some embodiments, the trialkylamine is selected from triethylamine, tri-n-propylamine, and diisopropylethylamine. In some embodiments, the trialkylamine is triethylamine or diisopropylethylamine. In some embodiments, the trialkylamine is triethylamine. In some embodiments, the trialkylamine is diisopropylethylamine.

Compounds of Formula (II)

Also disclosed herein are compounds of Formula (II), (II)

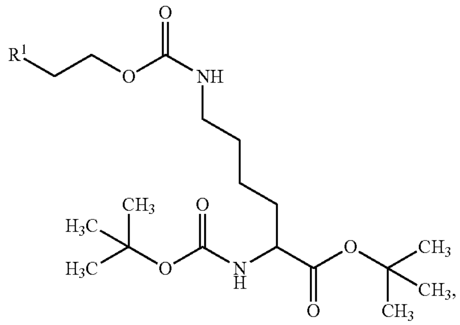

wherein $R^1$ is selected from chloro, bromo, and iodo.

In some embodiments of the compounds of Formula (II), $R^1$ is chloro. In some embodiments of the compounds of Formula (II), $R^1$ is bromo. In some embodiments of the compounds of Formula (II), $R^1$ is iodo.

Also disclosed herein are compounds of Formula (IIa), (IIa)

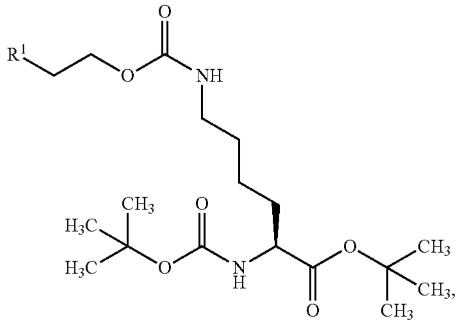

wherein $R^1$ is selected from chloro, bromo, and iodo.

In some embodiments of the compounds of Formula (IIa), $R^1$ is chloro. In some embodiments of the compounds of Formula (IIa), $R^1$ is bromo. In some embodiments of the compounds of Formula (IIa), $R^1$ is iodo.

Also disclosed herein are compounds of Formula (IIb), (IIb)

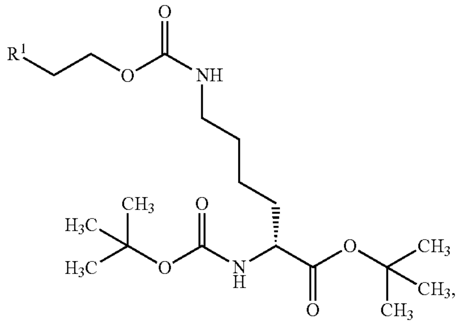

wherein $R^1$ is selected from chloro, bromo, and iodo.

In some embodiments of the compounds of Formula (IIb), $R^1$ is chloro. In some embodiments of the compounds of Formula (IIb), $R^1$ is bromo. In some embodiments of the compounds of Formula (IIb), $R^1$ is iodo.

Compounds of Formula (II) may be prepared by allowing a compound of Formula (I), wherein $R^1$ is selected from chloro, bromo and iodo (I)

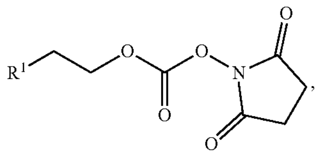

to react with a compound of Formula (V),

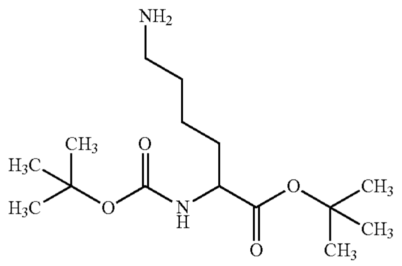

(V)

to afford the compound of Formula (II). In some embodiments, $R^1$ is chloro. In some embodiments, $R^1$ is bromo. In some embodiments, $R^1$ is iodo.

The reaction of the compound of Formula (I) with a compound of Formula (V) may be conducted in a solution comprising an aprotic solvent such as acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent that may be used is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane. In other embodiments, the aprotic solvent is selected from acetonitrile, acetone, methyl ethyl ketone, dichloromethane, chloroform, tetrahydrofuran, and N,N-dimethylformamide. In still further embodiments, the aprotic solvent is acetonitrile, or acetone, or methyl ethyl ketone, or dichloromethane, or chloroform, or tetrahydrofuran. In some embodiments, the aprotic solvent is acetonitrile. In some embodiments, the aprotic solvent is acetone. In some embodiments, the aprotic solvent is methyl ethyl ketone. In some embodiments, the aprotic solvent is dichloromethane. In some embodiments, the aprotic solvent is chloroform. In some embodiments, the aprotic solvent is tetrahydrofuran. In some embodiments, the aprotic solvent is 2-methyltetrahydrofuran. In some embodiments, the aprotic solvent is N,N-dimethylformamide.

The solution in which the compound of Formula (I) is allowed to react with the compound of Formula (V) may further comprise a base, which may comprise an organic base or an inorganic base, or both an organic base and an inorganic base. In some cases, the organic base used may be selected from a heterocyclic base and a trialkylamine, or a mixture thereof. Further, if a heterocyclic base is used, it may be selected from an aromatic heterocyclic base or a non-aromatic heterocyclic base, or a mixture of an aromatic heterocyclic base and a non-aromatic heterocyclic base. Examples of aromatic heterocyclic bases include, but are not limited to, pyridine, 1-alkylpyrrole, and 1-alkylimidazole, or a mixture thereof. Further examples aromatic heterocyclic bases that may be used include pyridine, 1-methylpyrrole, and 1-methylimidazole, or a mixture thereof. In some cases, the heterocyclic base used may be a non-aromatic heterocyclic base, including, but not limited to, an N-alkylpyrrolidine, an N-alkylpiperidine, an N-alkylmorpholine, and a 1,4-dialkylpiperazine, or a mixture thereof. Further examples of non-aromatic heterocyclic bases that may be used include, but are not limited to, N-methylpyrrolidine, N-methylpiperidine, and N-methylmorpholine. In other cases, one of ordinary skill in the art may use a base which is a trialkylamine, examples of which include, but are not limited to, trimethylamine, triethylamine, tri-n-propylamine, tri-n-butylamine, tripentylamine, trihexylamine, and diisopropylethylamine. In some embodiments, the base is diisopropylethylamine.

The reaction of a compound of Formula (I) with a compound of Formula (V) may be further conducted at a temperature in the range from about −25° C. to about 100° C., or at a range from about 0° C. to about room temperature. In some embodiments, the reaction is conducted at a temperature of about 10° C.

An example of the method that may be used to prepare a compound of Formula (II) is shown below in Scheme 2.

Scheme 2.

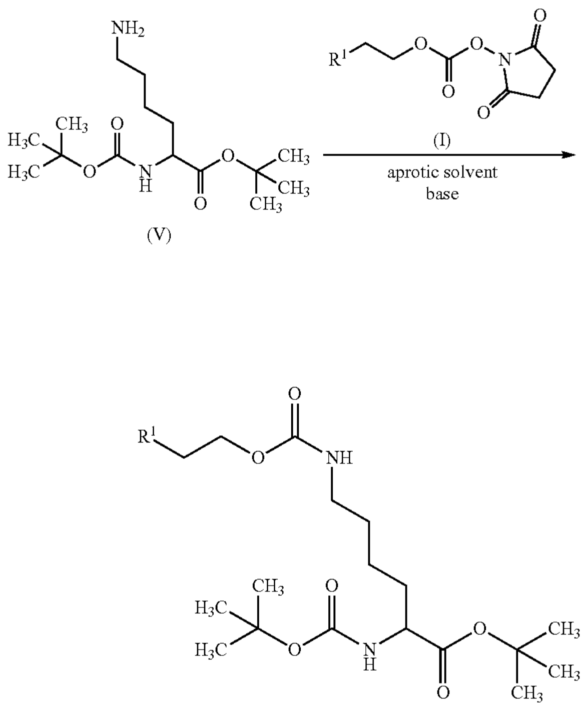

(V) (I) (II)

An example of the method that may be used to prepare a compound Formula (II), wherein $R^1$ is chloro, is shown below in Scheme 3.

Scheme 3.

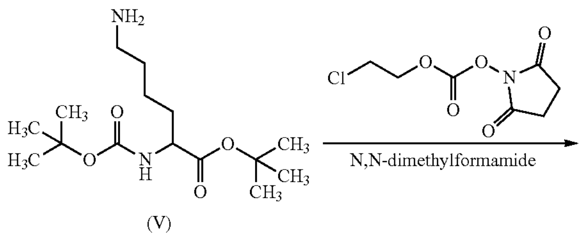

(V)

-continued

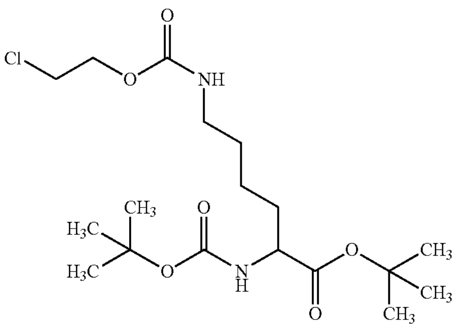

Compounds of Formula (IIa) and (IIb) may be prepared using methods that are similar to those described above by using the L-enantiomer or the D-enantiomer of the compound of Formula (V) as shown below in Scheme 4 and Scheme 5.

Scheme 4.

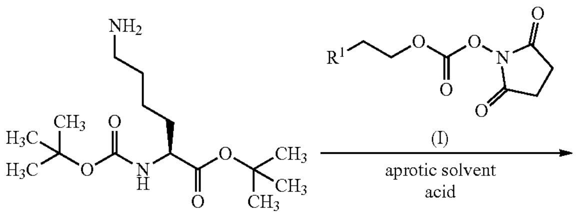

(Va)

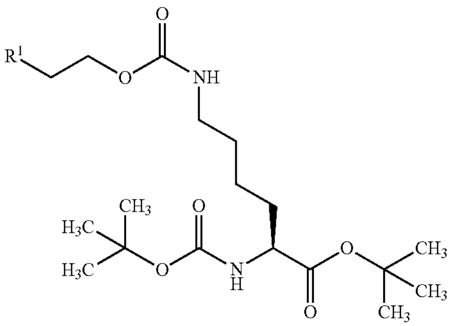

(IIa)

Scheme 5.

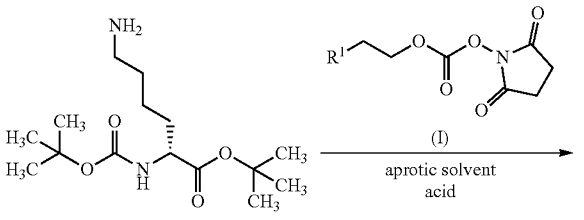

(Vb)

-continued

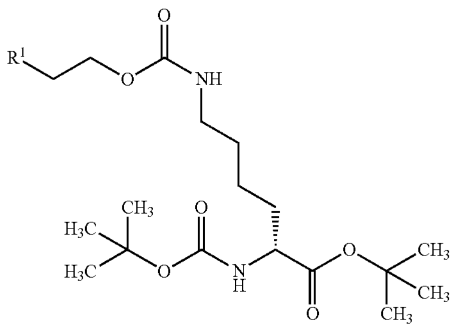

(IIb)

Also disclosed herein are methods of preparing a compound of Formula (IIa), (IIa)

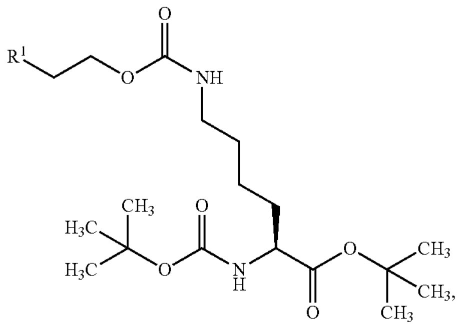

comprising allowing a compound of Formula (I), (I)

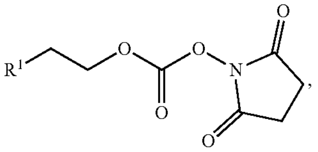

to react with a compound of Formula (Va)

(Va)

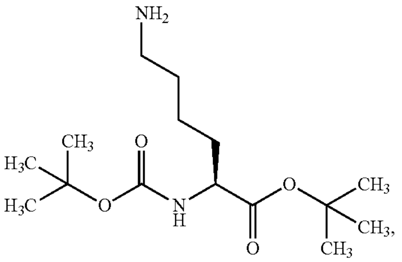

to afford the compound of Formula (IIa), wherein $R^1$ is selected from chloro, bromo and iodo. In some embodiments of the methods, $R^1$ is chloro. In some embodiments of the methods, $R^1$ is bromo. In some embodiments of the methods, $R^1$ is iodo. In some embodiments, the reaction of the compound of Formula (Va) with the compound of Formula (I) is performed in a solution comprising an aprotic solvent. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane. In some embodiments, the aprotic solvent is selected from acetonitrile, acetone, methyl ethyl ketone, dichloromethane, chloroform, tetrahydrofuran, and N,N-dimethylformamide. In some embodiments, the aprotic solvent is acetonitrile. In some embodiments, the aprotic solvent is acetone. In some embodiments, the aprotic solvent is methyl ethyl ketone. In some embodiments, the aprotic solvent is dichloromethane. In some embodiments, the aprotic solvent is chloroform. In some embodiments, the aprotic solvent is tetrahydrofuran. In some embodiments, the aprotic solvent is 2-methyltetrahydrofuran. In some embodiments, the aprotic solvent is N,N-dimethylformamide.

Also disclosed herein are methods of preparing a compound of Formula (IIb), (IIb)

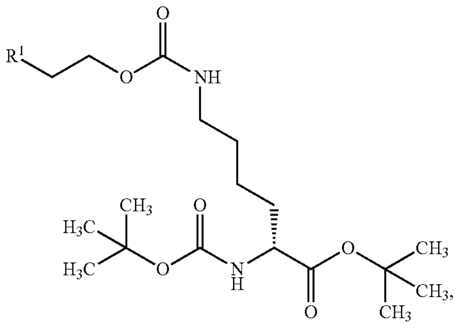

comprising allowing a compound of Formula (I), (I)

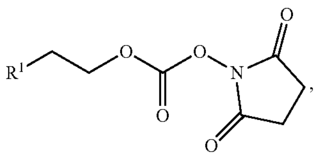

to react with a compound of Formula (Vb)

(Vb)

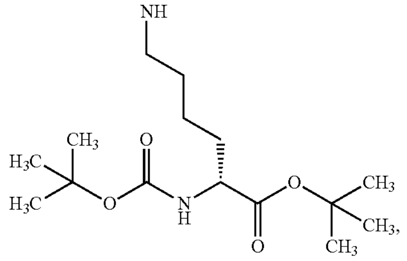

to afford the compound of Formula (IIb), wherein $R^1$ is selected from chloro, bromo and iodo. In some embodiments of the methods, $R^1$ is chloro. In some embodiments of the methods, $R^1$ is bromo. In some embodiments of the methods, $R^1$ is iodo. In some embodiments, the reaction of the compound of Formula (Vb) with the compound of Formula (I) is performed in a solution comprising an aprotic solvent. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane. In some embodiments, the aprotic solvent is selected from acetonitrile, acetone, methyl ethyl ketone, dichloromethane, chloroform, tetrahydrofuran, and N,N-dimethylformamide. In some embodiments, the aprotic solvent is acetonitrile. In some embodiments, the aprotic solvent is acetone. In some embodiments, the aprotic solvent is methyl ethyl ketone. In some embodiments, the aprotic solvent is dichloromethane. In some embodiments, the aprotic solvent is chloroform. In some embodiments, the aprotic solvent is tetrahydrofuran. In some embodiments, the aprotic solvent is 2-methyltetrahydrofuran. In some embodiments, the aprotic solvent is N,N-dimethylformamide.

Compounds of Formula (V), including the L-enantiomer and the D-enantiomer, are commercially available or may be prepared by methods known to those of ordinary skill in the art.

Compounds of Formula (III)

Also disclosed herein are compounds of Formula (III), (III)

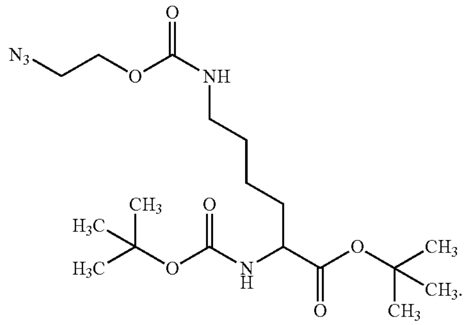

In some embodiments, the compound of Formula (III) is a compound of Formula (IIIa), (IIIa)

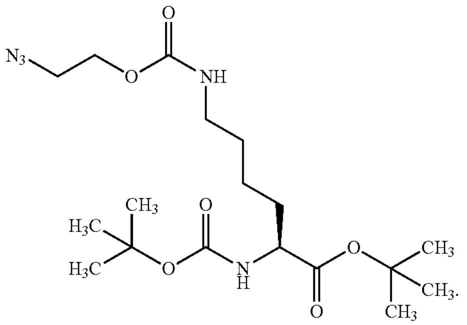

In some embodiments, the compound of formula (III) is the compound of Formula (IIIb), (IIIb)

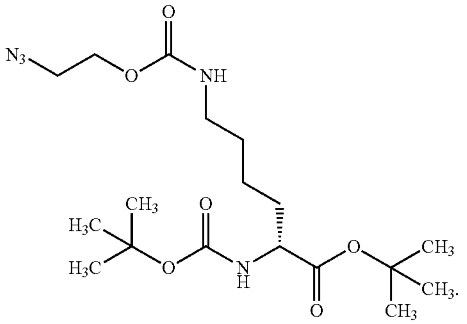

Compounds of Formula (III) may be prepared by allowing a compound of Formula (II), wherein $R^1$ is selected from chloro, bromo, and iodo, to react with an alkali azide salt to afford the compound of Formula (III). In some embodiments, the alkali azide salt is selected from lithium azide, sodium azide, and potassium azide. In some cases, the alkali azide salt is lithium azide. In other cases, the alkali azide salt is sodium azide. In still further cases, the alkali azide salt is potassium azide. The reaction of the compound of Formula (II) with the alkali azide salt may be performed in a solution comprising an aprotic solvent, a protic solvent, or a mixture thereof. The aprotic solvent that may be used may be selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some cases, the aprotic solvent is selected from acetonitrile, tetrahydrofuran, N-methylpyrrolidine, dimethylsulfoxide, N,N-dimethylformamide, dimethylacetamide, and 1,4-dioxane. In some embodiments, the aprotic solvent is acetonitrile. In some embodiments, the aprotic solvent is tetrahydrofuran. In some embodiments, the aprotic solvent is 2-methyltetrahydrofuran. In some embodiments, the aprotic solvent is N,N-dimethylformamide. In some embodiments, the aprotic solvent is 1,4-dioxane. In some cases, the reaction of the compound of Formula (II) with the alkali azide salt may be performed in a solution comprising a mixture of an aprotic solvent and a protic solvent, wherein the aprotic solvent is as described above and the protic solvent may be selected from water and an alcohol. In some embodiments, the protic solvent is water. In some embodiments, the protic solvent is an alcohol. Examples of alcohols that may be used include, but are not limited to, methanol, ethanol, n-propanol, iso-propanol, n-butanol, iso-butanol, n-pentanol, and iso-pentanol. In some embodiments, the alcohol is selected from methanol, ethanol, n-propanol, and iso-propanol. In some cases, the solution may comprise a mixture of water and 1,4-dioxane. In some cases, the solution may comprise a mixture of water and acetonitrile. The reaction of a compound of Formula (II), wherein $R^1$ is selected from chloro, bromo, and iodo, with an alkali azide salt may be conducted at a temperature in the range from about 25° C. to about 150° C., or from about 75° C. to about 80° C. In some embodiments, the reaction is conducted at a temperature of about 80° C.

An example of the method that may be used to prepare a compound of Formula (III) by reaction of a compound of Formula (II), wherein $R^1$ is selected from chloro, bromo, and iodo, to react with an alkali azide salt is shown below in Scheme 6.

Scheme 6.

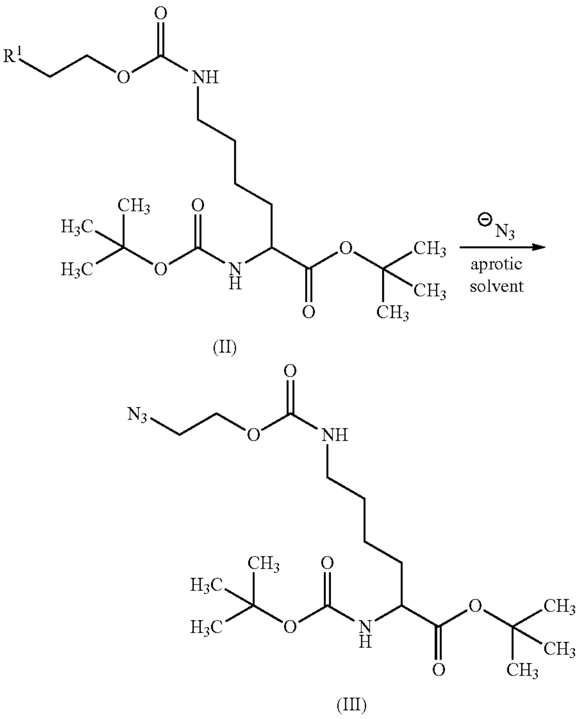

(II)

(III)

An example of the method that may be used to prepare a compound Formula (III) by reaction of a compound of Formula (II), wherein $R^1$ is chloro, and sodium azide is shown below in Scheme 7.

Scheme 7.

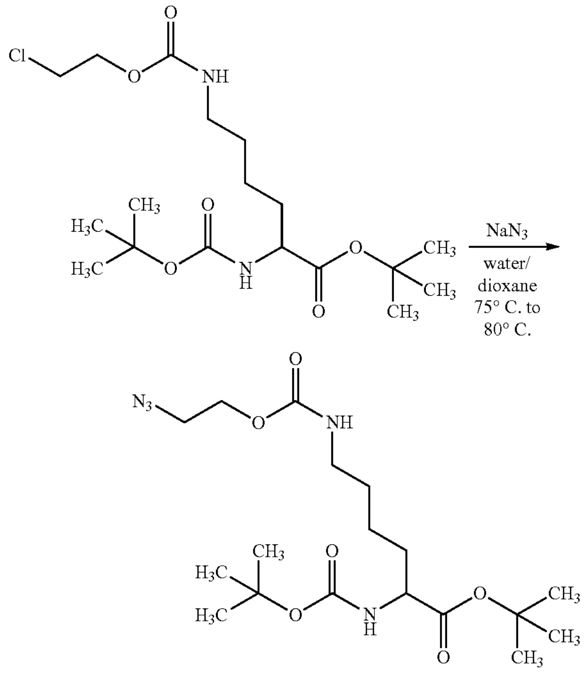

(III)

Compounds of Formula (IIIa) and (IIIb) may be prepared using methods that are similar to those described above by using the L-enantiomer or the D-enantiomer of the compound of Formula (II) as shown below in Scheme 8 and Scheme 9.

Scheme 8.

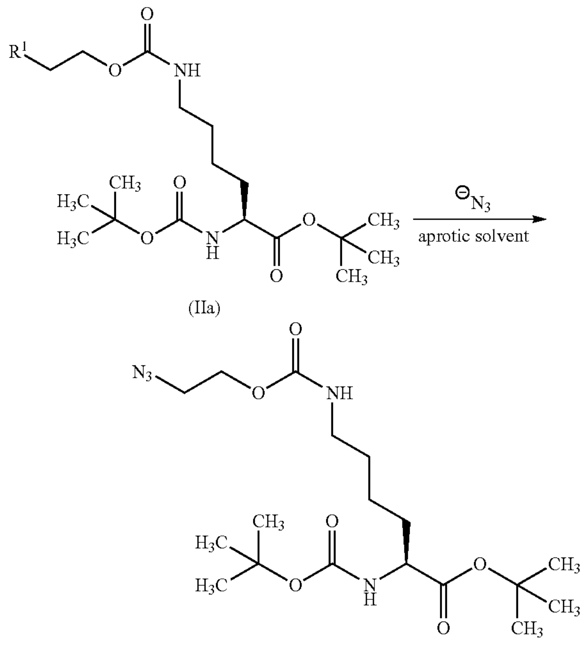

(IIa)

(IIIa)

Scheme 9.

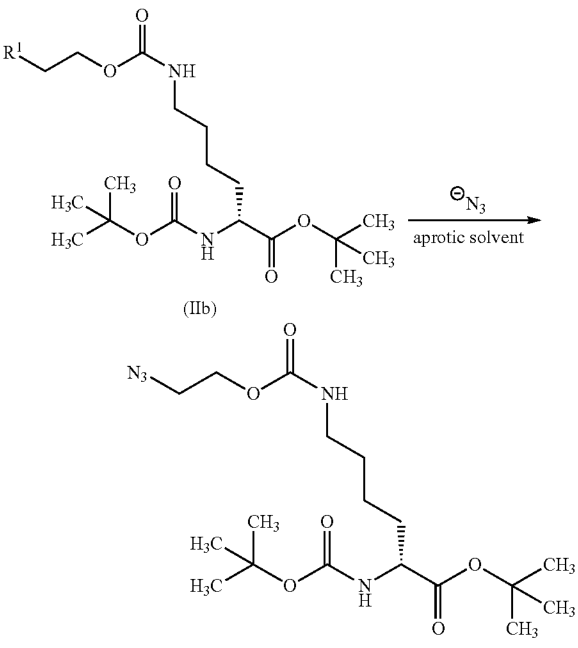

(IIb)

(IIIb)

Also disclosed herein are method of preparing a compound of Formula (IIIa), (IIIa)

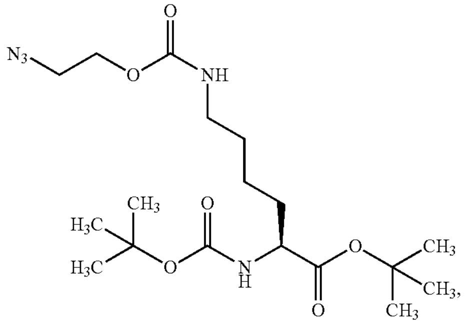

comprising allowing a compound of Formula (IIa), (IIa)

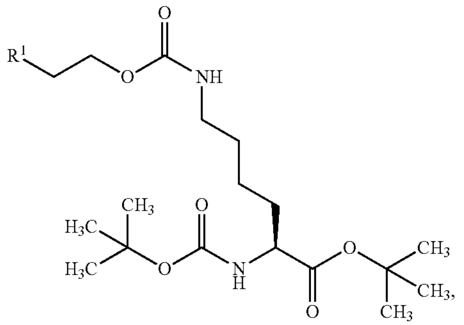

wherein $R^1$ is selected from chloro, bromo, and iodo, to react with an alkali azide salt to afford the compound of Formula (IIIa). In some embodiments, the alkali azide salt is selected from lithium azide, sodium azide, and potassium azide. In some embodiments, the alkali azide salt is lithium azide. In some embodiments, the alkali azide salt is sodium azide. In some embodiments, the alkali azide salt is potassium azide. In some embodiments, the reaction of the compound of Formula (IIa) with the alkali azide salt is performed in a solution comprising an aprotic solvent, a protic solvent, or a mixture thereof. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, tetrahydrofuran, N-methylpyrrolidine, dimethylsulfoxide, N,N-dimethylformamide, dimethylacetamide, and 1,4-dioxane. In some embodiments, the aprotic solvent is selected from acetonitrile, tetrahydrofuran, N,N-dimethylformamide, and 1,4-dioxane. In some embodiments, the aprotic solvent is acetonitrile. In some embodiments, the aprotic solvent is tetrahydrofuran. In some embodiments, the aprotic solvent is 2-methyltetrahydrofuran. In some embodiments, the aprotic solvent is N,N-dimethylformamide. In some embodiments, the aprotic solvent is 1,4-dioxane. In some embodiments, the reaction of the compound of Formula (IIa) with the alkali azide salt is performed in a solution comprising a mixture of an aprotic solvent and a protic solvent. In some embodiments, the protic solvent is selected from water and an alcohol. In some embodiments, the protic solvent is water. In some embodiments, the protic solvent is an alcohol. In some embodiments, the alcohol is selected from methanol, ethanol, n-propanol, iso-propanol, n-butanol, iso-butanol, n-pentanol, and iso-pentanol. In some embodiments, the alcohol is selected from methanol, ethanol, n-propanol, and iso-propanol. In some embodiments, the solution comprises a mixture of water and 1,4-dioxane. In some embodiments, the solution comprises a mixture of water and acetonitrile.

Also disclosed herein are methods of preparing a compound of Formula (IIIb), (IIIb)

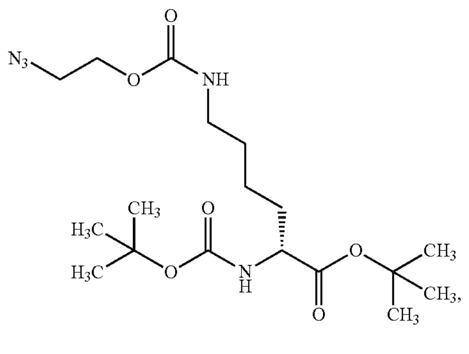

comprising allowing a compound of Formula (IIb), (IIb)

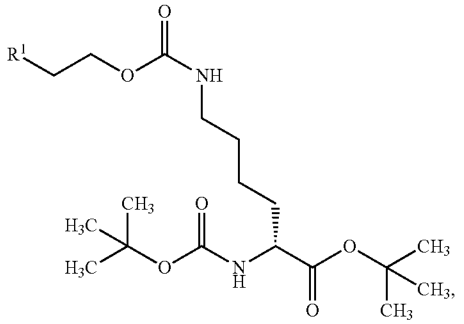

wherein $R^1$ is selected from chloro, bromo, and iodo, to react with an alkali azide salt to afford the compound of Formula (IIIb). In some embodiments, the alkali azide salt is selected from lithium azide, sodium azide, and potassium azide. In some embodiments, the alkali azide salt is lithium azide. In some embodiments, the alkali azide salt is sodium azide. In some embodiments, the alkali azide salt is potassium azide. In some embodiments, the reaction of the compound of Formula (IIb) with the alkali azide salt is performed in a solution comprising an aprotic solvent, a protic solvent, or a mixture thereof. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, tetrahydrofuran, N-methylpyrrolidine, dimethylsulfoxide, N,N-dimethylformamide, dimethylacetamide, and 1,4-dioxane. In some embodiments, the aprotic solvent is selected from acetonitrile, tetrahydrofuran, N,N-dimethylformamide, and 1,4-dioxane. In some embodiments, the aprotic solvent is acetonitrile. In some embodiments, the aprotic solvent is tetrahydrofuran. In some embodiments, the aprotic solvent is 2-methyltetrahydrofuran. In some embodiments, the aprotic solvent is N,N-dimethylformamide. In some embodiments, the aprotic solvent is 1,4-dioxane. In some embodiments, the reaction of the compound of Formula (IIb) with the alkali azide salt is performed in a solution comprising a mixture of an aprotic solvent and a protic solvent. In some embodiments, the protic solvent is selected from water and an alcohol. In some embodiments, the protic solvent is water. In some embodiments, the protic solvent is an alcohol. In some embodiments, the alcohol is selected from methanol, ethanol, n-propanol, iso-propanol, n-butanol, iso-butanol, n-pentanol, and iso-pentanol. In some embodiments, the alcohol is selected from methanol, ethanol, n-propanol, and iso-propanol. In some embodiments, the solution comprises a mixture of water and 1,4-dioxane. In some embodiments, the solution comprises a mixture of water and acetonitrile.

Compounds of Formula (VI)

Also disclosed herein are methods of preparing a compound of Formula (VI)

(VI)

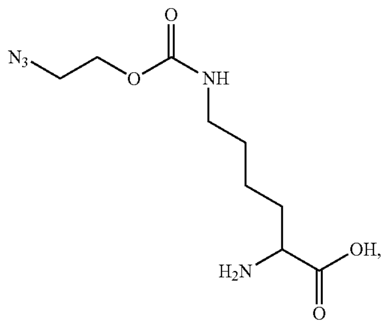

or a salt thereof, comprising allowing a compound of Formula (III)

(III)

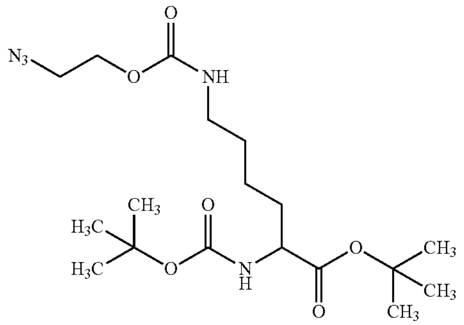

to react with an acid to afford a compound of Formula (VI) or a salt thereof. In some embodiments, the compound of Formula (VI) is isolated as a salt thereof. In some embodiments, the compound of Formula (VI) is converted to a salt thereof using methods known to a person of ordinary skill in the art. In some embodiments, the reaction of the compound of Formula (III) with an acid is performed in a solution comprising an aprotic solvent, a protic solvent, or a mixture thereof. The aprotic solvents that may be used to conduct the reaction include, but are not limited to, acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, tetrahydrofuran, N-methylpyrrolidine, dimethylsulfoxide, N,N-dimethylformamide, dimethylacetamide, and 1,4-dioxane. In other cases, the aprotic solvent is selected from acetonitrile, tetrahydrofuran, N,N-dimethylformamide, and 1,4-dioxane. In some embodiments, the aprotic solvent is acetonitrile. In some embodiments, the aprotic solvent is tetrahydrofuran. In some embodiments, the aprotic solvent is 2-methyltetrahydrofuran. In some embodiments, the aprotic solvent is N,N-dimethylformamide. In some embodiments, the aprotic solvent is 1,4-dioxane. In some cases, the reaction of the compound of Formula (III) with an acid is performed in a solution comprising a mixture of a protic solvent and an aprotic solvent, wherein the protic solvent comprises, for example, water. In some embodiments, the reaction of the compound of Formula (III) with an acid is performed in a solution comprising a mixture of 1,4-dioxane and water. The reaction of the compound of Formula (III) with an acid may be conducted using acids that include, but are not limited to, phosphoric acid, hydrochloric acid, acetic acid, and trifluoroacetic acid. In some cases, the acid may be phosphoric acid. In other cases, the acid may be hydrochloric acid. In still other cases, the acid may be acetic acid. In further cases, the acid may be trifluoroacetic acid. In some embodiments, a base is added to the acidic mixture comprising the compound of Formula (III). In some embodiments, the base is ammonium hydroxide, sodium hydroxide, or potassium hydroxide. In some embodiments, the base is ammonium hydroxide. In some embodiments, the base is added to the acid mixture comprising the compound of Formula (III) to adjust the pH of the solution to a range of from about 4 to 10. In some embodiments, the base is added to the acid mixture comprising the compound of Formula (III) to adjust the pH of the solution to a range of from about 7 to 9.5. In some embodiments, the pH of the solution is adjusted to a range of from about 8 to 9.5. In some embodiments, the base is added to the acid mixture comprising the compound of Formula (III) to adjust the pH of the solution to a range of from about 7 to 9. In some embodiments, the pH of the solution is adjusted to a range of from about 7 to 8. In some embodiments, the pH of the solution is adjusted to a range of from about 8 to 9. In some embodiments, the pH of the solution is adjusted to about 4. In some embodiments, the pH of the solution is adjusted to about 5. In some embodiments, the pH of the solution is adjusted to about 6. In some embodiments, the pH of the solution is adjusted to about 7. In some embodiments, the pH of the solution is adjusted to about 8. In some embodiments, the pH of the solution is adjusted to about 9. In some embodiments, the pH of the solution is adjusted to about 10. The reaction may be conducted at a temperature in the range from about 0° C. to about 100° C., or from about 25° C. to about 75° C., or from about 25° C. to about 50° C., or at about 40° C. In some embodiments, the reaction is conducted at a temperature range from about 0° C. to about 50° C., such as from about 10° C. to about 45° C.

An example in which a compound of Formula (III) is allowed to react with an acid to afford a compound of Formula (VI) is shown below, in which the compound of Formula (III) is allowed to react with hydrochloric acid in a mixture of acetonitrile and water at a temperature of 40° C. to afford the compound of Formula (VI). The compound of Formula (VI) may be isolated as a salt, for example the hydrochloride salt, or it may be isolated as the zwitterionic form of the compound by neutralization of the reaction mixture following reaction of the compound of Formula (III) with an acid as shown in Scheme 10.

Scheme 10.

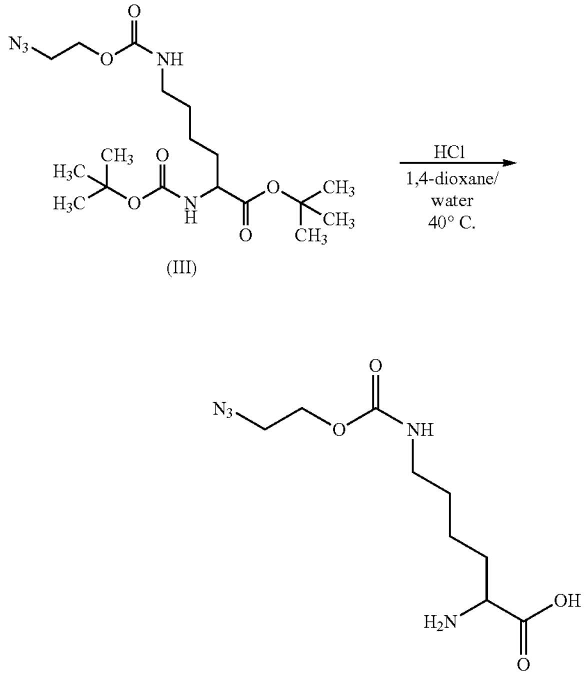

(III)

(VI)

Compounds of Formula (VIa) and (VIb) may be prepared as described above for the compounds of Formula (VI), wherein a compound of Formula (IIIa) or Formula (IIIb) is allowed to react with an acid as described above and as shown below in Schemes 11 and 12.

Scheme 11.

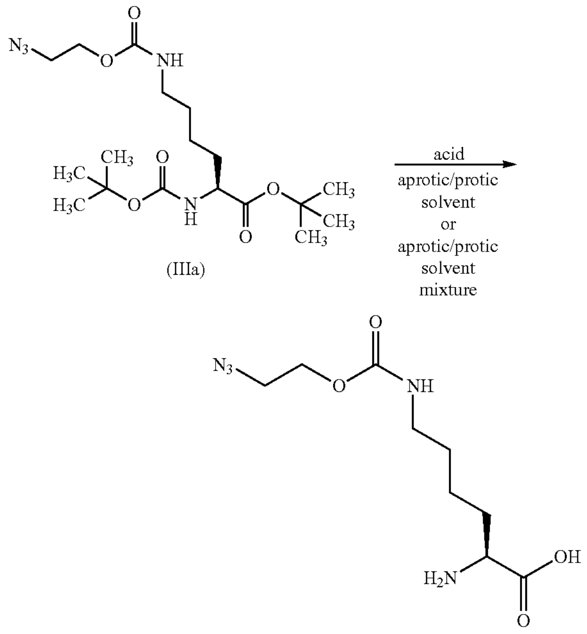

(IIIa)

(VIa)

Scheme 12.

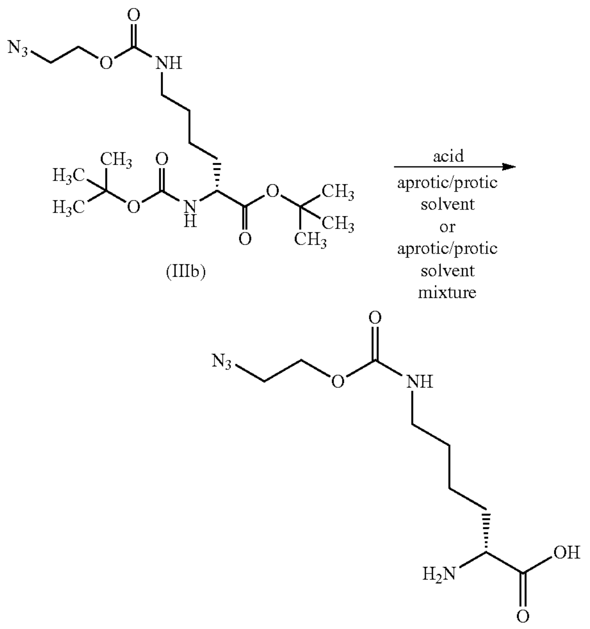

(IIIb)

(VIb)

Also disclosed herein are methods of preparing a compound of Formula (VIa)

(VIa)

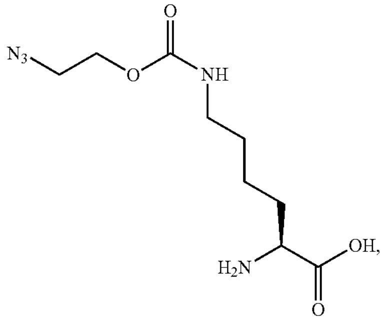

or a salt thereof, comprising allowing a compound of Formula (IIIa)

(IIIa)

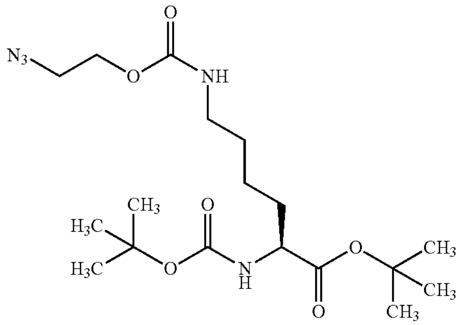

to react with an acid to afford a compound of Formula (VIa) or a salt thereof. In some embodiments, the reaction of the compound of Formula (IIIa) with the acid is performed in a solution comprising an aprotic solvent, a protic solvent, or a mixture thereof. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, tetrahydrofuran, N-methylpyrrolidine, dimethylsulfoxide, N,N-dimethylformamide, dimethylacetamide, and 1,4-dioxane. In some embodiments, the aprotic solvent is selected from acetonitrile, tetrahydrofuran, N,N-dimethylformamide, and 1,4-dioxane. In some embodiments, the aprotic solvent is acetonitrile. In some embodiments, the aprotic solvent is tetrahydrofuran. In some embodiments, the aprotic solvent is 2-methyltetrahydrofuran. In some embodiments, the aprotic solvent is N,N-dimethylformamide. In some embodiments, the aprotic solvent is 1,4-dioxane. In some embodiments, the reaction of the compound of Formula (IIIa) with the acid is performed in a solution comprising a mixture of a protic solvent and an aprotic solvent, wherein the protic solvent may be water. In some embodiments, the reaction of the compound of Formula (IIIa) with the acid is performed in a solution comprising a mixture of 1,4-dioxane and water. In some embodiments, the acid is selected from phosphoric acid, hydrochloric acid, acetic acid, and trifluoroacetic acid. In some embodiments, the acid is phosphoric acid. In some embodiments, the acid is hydrochloric acid. In some embodiments, the acid is acetic acid. In some embodiments, the acid is trifluoroacetic acid. In some embodiments, a base is added to the acidic mixture comprising Formula (IIIa). In some embodiments, the base is ammonium hydroxide, sodium hydroxide, or potassium hydroxide. In some embodiments, the base is ammonium hydroxide. In some embodiments, the base is added to the acid mixture comprising Formula (IIIa) to adjust the pH of the solution to a range of from about 4 to 10. In some embodiments, the base is added to the acid mixture comprising Formula (IIIa) to adjust the pH of the solution to a range of from about 7 to 9. In some embodiments, the pH of the solution is adjusted to a range of from about 8 to 9. In some embodiments, the pH of the solution is adjusted to about 4. In some embodiments, the pH of the solution is adjusted to about 5. In some embodiments, the pH of the solution is adjusted to about 6. In some embodiments, the pH of the solution is adjusted to about 7. In some embodiments, the pH of the solution is adjusted to about 8. In some embodiments, the pH of the solution is adjusted to about 9. In some embodiments, the pH of the solution is adjusted to about 10.

Also disclosed herein are methods of preparing a compound of Formula (VIb)

(VIb)

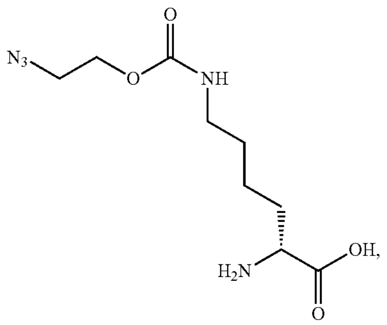

or a salt thereof, comprising allowing a compound of Formula (IIIb)

(IIIb)

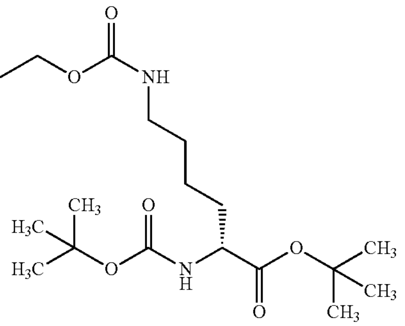

to react with an acid to afford a compound of Formula (VIb) or a salt thereof. In some embodiments, the reaction of the compound of Formula (IIIb) with the acid is performed in a solution comprising an aprotic solvent, a protic solvent, or a mixture thereof. In some embodiments, the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols. In some embodiments, the aprotic solvent is selected from acetonitrile, tetrahydrofuran, N-methylpyrrolidine, dimethylsulfoxide, N,N-dimethylformamide, dimethylacetamide, and 1,4-dioxane. In some embodiments, the aprotic solvent is selected from acetonitrile, tetrahydrofuran, N,N-dimethylformamide, and 1,4-dioxane. In some embodiments, the aprotic solvent is acetonitrile. In some embodiments, the aprotic solvent is tetrahydrofuran. In some embodiments, the aprotic solvent is 2-methyltetrahydrofuran. In some embodiments, the aprotic solvent is N,N-dimethylformamide. In some embodiments, the aprotic solvent is 1,4-dioxane. In some embodiments, the reaction of the compound of Formula (IIIb) with the acid is performed in a solution comprising a mixture of a protic solvent and an aprotic solvent, wherein the protic solvent may be water. In some embodiments, the reaction of the compound of Formula (IIIb) with the acid is performed in a solution comprising a mixture of 1,4-dioxane and water. In some embodiments, the acid is selected from phosphoric acid, hydrochloric acid, acetic acid, and trifluoroacetic acid. In some embodiments, the acid is phosphoric acid. In some embodiments, the acid is hydrochloric acid. In some embodiments, the acid is acetic acid. In some embodiments, the acid is trifluoroacetic acid. In some embodiments, a base is added to the acidic mixture comprising Formula (IIIb). In some embodiments, the base is ammonium hydroxide, sodium hydroxide, or potassium hydroxide. In some embodiments, the base is ammonium hydroxide. In some embodiments, the base is added to the acid mixture comprising Formula (IIIb) to adjust the pH of the solution to a range of from about 4 to 10. In some embodiments, the base is added to the acid mixture comprising Formula (IIIb) to adjust the pH of the solution to a range of from about 7 to 9. In some embodiments, the pH of the solution is adjusted to a range of from about 8 to 9. In some embodiments, the pH of the solution is adjusted to about 4. In some embodiments, the pH of the solution is adjusted to about 5. In some embodiments, the pH of the solution is adjusted to about 6. In some embodiments, the pH of the solution is adjusted to about 7. In some embodiments, the pH of the solution is adjusted to about 8. In some embodiments, the pH of the solution is adjusted to about 9. In some embodiments, the pH of the solution is adjusted to about 10.

In one aspect, provided herein is a method of preparing the compound of Formula (VI), or a salt thereof, as outlined in Scheme 13.

Scheme 13.

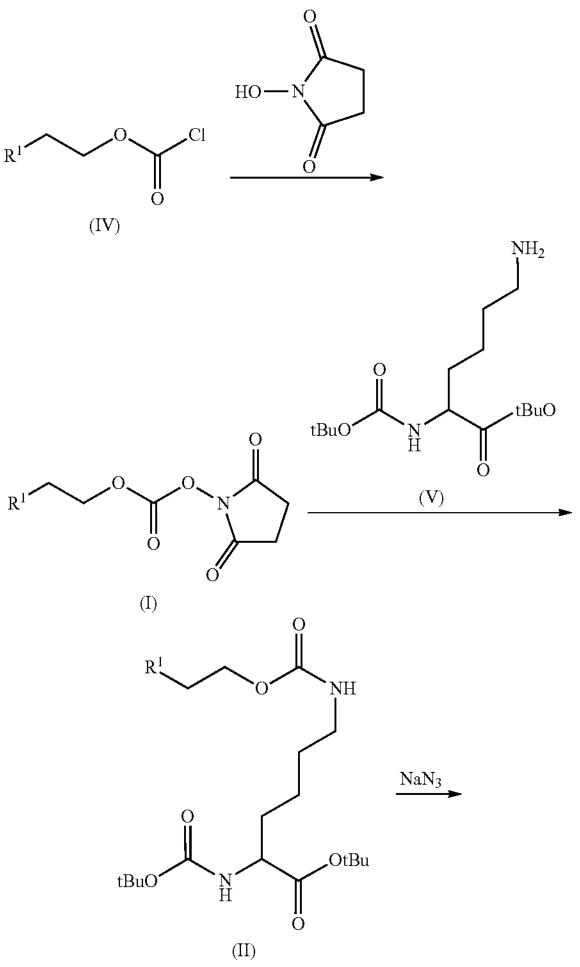

(IV)

(V)

(I)

(II)

-continued

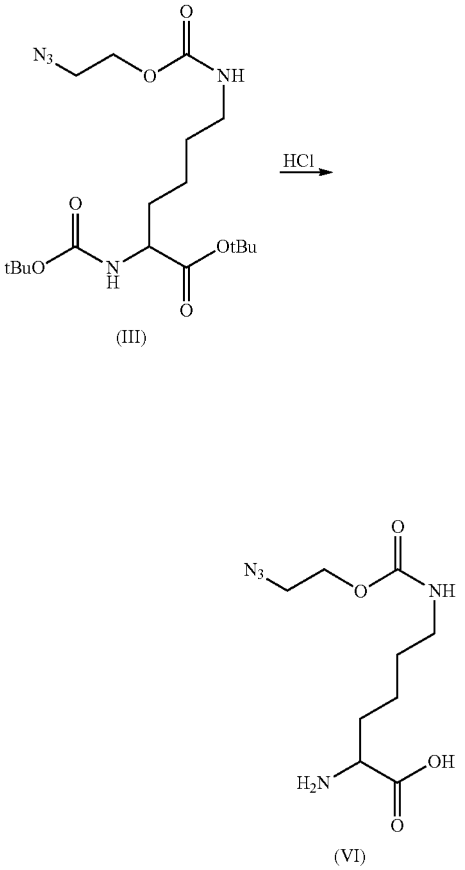

(III)

(VI)

wherein $R^1$ is chloro, bromo, or iodo.

In some embodiments wherein $R^1$ is chloro, the compound of Formula (VI) is prepared as outlined in Scheme 14.

Scheme 14.

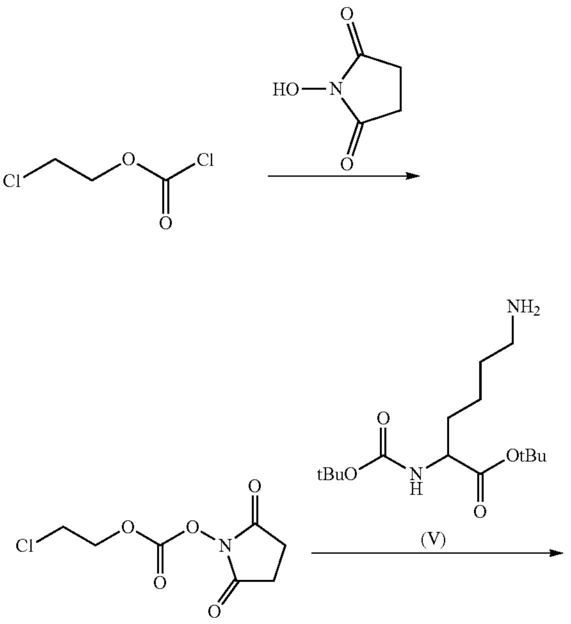

(V)

-continued
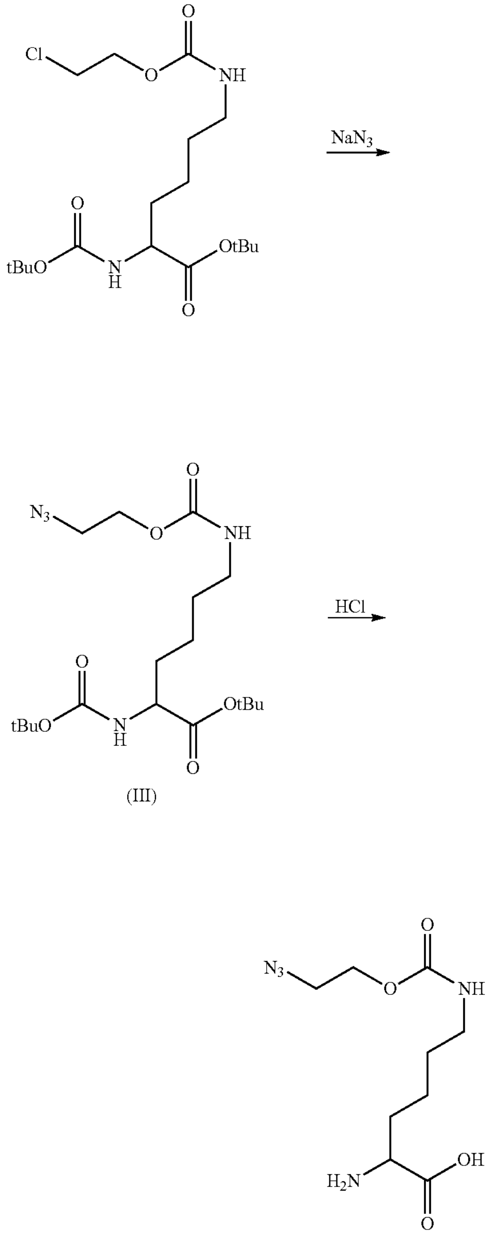
(III)
(VI)
In some variations, the compounds of Formula (VIa) and (VIb), or salts thereof, are prepared as outlined in Scheme 15 and Scheme 16.
Scheme 15.
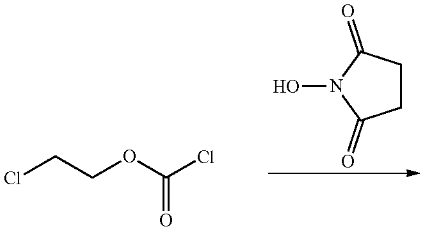
-continued
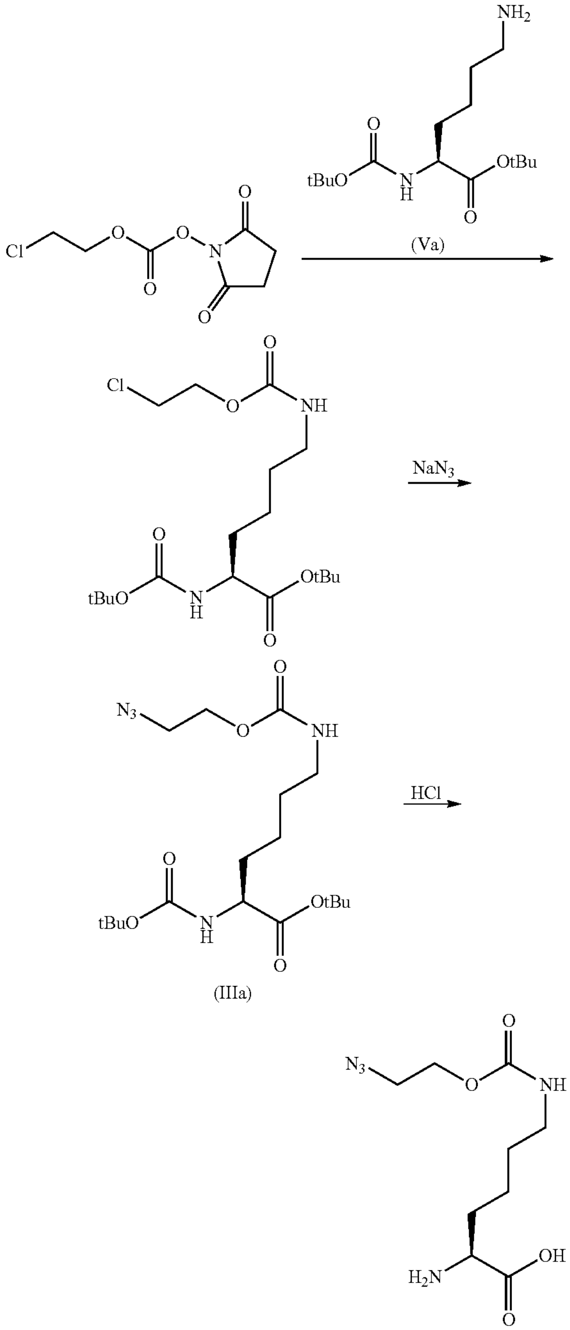
(IIIa)
(VIa)
Scheme 16.
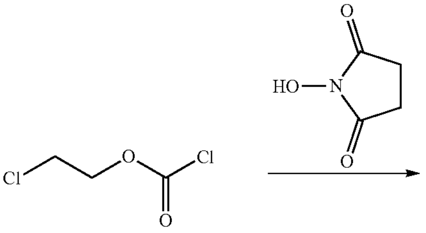

-continued

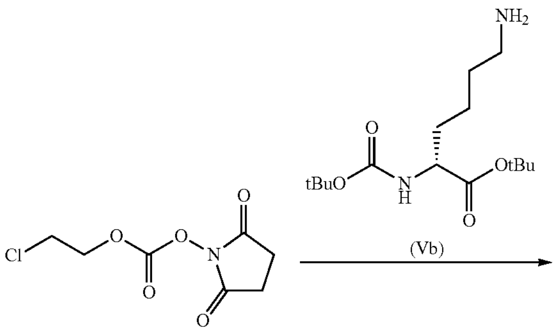

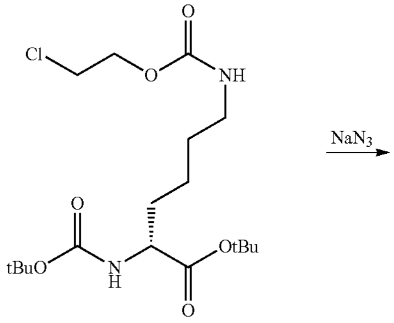

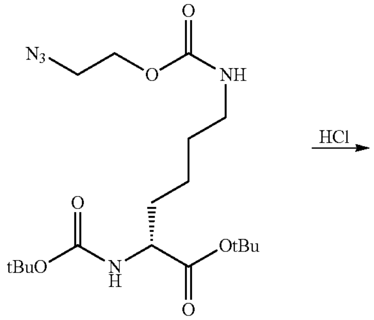

(IIIb)

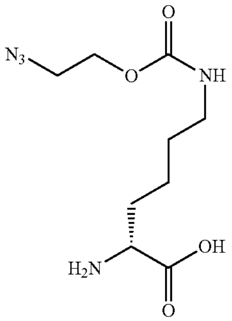

(VIb)

Compounds of Formula (VII)

Also disclosed herein are compounds of Formula (VII)

(VII)

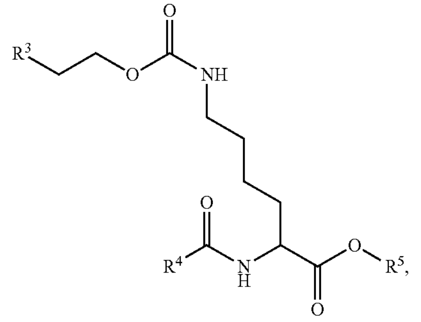

wherein:

$R^3$ is selected from chloro, bromo and iodo;

$R^4$ is selected from —$OR^6$, —$CF_3$, —$CH_2C_6$-$C_{12}$aryl, and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$aryl.

In some embodiments of the compounds of Formula (VII), $R^4$ is —$OR^6$, and $R^5$ is $C_1$-$C_6$ alkyl. In some embodiments, $R^6$ is $C_1$-$C_6$ alkyl. In some embodiments, $C_1$-$C_6$ alkyl is tert-butyl. In some embodiments, $R^5$ is tert-butyl.

In some embodiments of the compounds of Formula (VII), $R^3$ is chloro. In some embodiments, $R^6$ is $C_1$-$C_6$ alkyl. In some embodiments, $C_1$-$C_6$ alkyl is tert-butyl. In some embodiments, $R^5$ is tert-butyl. In some embodiments, $R^4$ is —$OR^6$, and $R^5$ is $C_1$-$C_6$ alkyl.

In some embodiments of the compounds of Formula (VII), $R^3$ is bromo. In some embodiments, $R^6$ is $C_1$-$C_6$ alkyl. In some embodiments, $C_1$-$C_6$ alkyl is tert-butyl. In some embodiments, $R^5$ is tert-butyl. In some embodiments, $R^4$ is —$OR^6$, and $R^5$ is $C_1$-$C_6$ alkyl.

In some embodiments of the compounds of Formula (VII), $R^3$ is iodo. In some embodiments, $R^6$ is $C_1$-$C_6$ alkyl. In some embodiments, $C_1$-$C_6$ alkyl is tert-butyl. In some embodiments, $R^5$ is tert-butyl. In some embodiments, $R^4$ is —$OR^6$, and $R^5$ is $C_1$-$C_6$ alkyl.

Also disclosed herein are compounds of Formula (VIIa)

(VIIa)

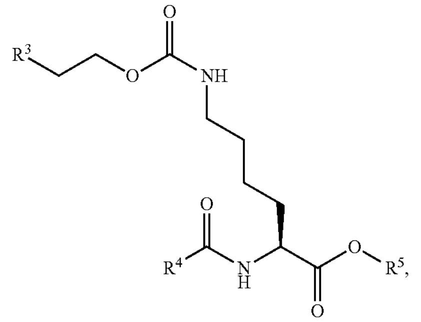

wherein:

$R^3$ is selected from chloro, bromo and iodo;

$R^4$ is selected from —$OR^6$, —$CF_3$, —$CH_2C_6$-$C_{12}$aryl, and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$aryl.

In some embodiments of the compounds of Formula (VIIa), $R^6$ is selected from $C_1$-$C_6$ alkyl, $C_6$-$C_{12}$aryl, and —$CH_2C_6$-$C_{12}$aryl. In some embodiments, $R^4$ is —$OR^6$, and $R^5$ is $C_1$-$C_6$ alkyl. In some embodiments, $R^6$ is $C_1$-$C_6$ alkyl. In some embodiments, $C_1$-$C_6$ alkyl is tert-butyl. In some embodiments, $R^5$ is tert-butyl.

In some embodiments of the compounds of Formula (VIIa), $R^3$ is chloro. In some embodiments, $R^6$ is $C_1$-$C_6$ alkyl. In some embodiments, $C_1$-$C_6$ alkyl is tert-butyl. In some embodiments, $R^5$ is tert-butyl. In some embodiments, $R^4$ is —$OR^6$, and $R^5$ is $C_1$-$C_6$ alkyl.

In some embodiments of the compounds of Formula (VIIa), $R^3$ is bromo. In some embodiments, $R^6$ is $C_1$-$C_6$ alkyl. In some embodiments, $C_1$-$C_6$ alkyl is tert-butyl. In some embodiments, $R^5$ is tert-butyl. In some embodiments, $R^4$ is —$OR^6$, and $R^5$ is $C_1$-$C_6$ alkyl.

In some embodiments of the compounds of Formula (VIIa), $R^3$ is iodo. In some embodiments, $R^6$ is $C_1$-$C_6$ alkyl. In some embodiments, $C_1$-$C_6$ alkyl is tert-butyl. In some embodiments, $R^5$ is tert-butyl. In some embodiments, $R^4$ is —$OR^6$, and $R^5$ is $C_1$-$C_6$ alkyl.

Also disclosed herein are compounds of Formula (VIIb)

(VIIb)

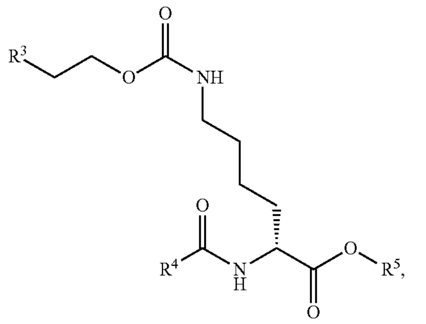

wherein:

$R^3$ is selected from chloro, bromo and iodo;

$R^4$ is selected from —$OR^6$, —$CF_3$, —$CH_2C_6$-$C_{12}$aryl and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$aryl. In some embodiments, $R^6$ is selected from $C_1$-$C_6$ alkyl, $C_6$-$C_{12}$aryl, and —$CH_2C_6$-$C_{12}$aryl.

In some embodiments of the compounds of Formula (VIIb), $R^4$ is —$OR^6$, and $R^5$ is $C_1$-$C_6$ alkyl. In some embodiments, $R^6$ is $C_1$-$C_6$ alkyl. In some embodiments, $C_1$-$C_6$ alkyl is tert-butyl. In some embodiments, $R^5$ is tert-butyl.

In some embodiments of the compounds of Formula (VIIb), $R^3$ is chloro. In some embodiments, $R^6$ is selected from $C_1$-$C_6$ alkyl, $C_6$-$C_{12}$aryl, and —$CH_2C_6$-$C_{12}$aryl. In some embodiments, $R^4$ is —$OR^6$, and $R^5$ is $C_1$-$C_6$ alkyl. In some embodiments, $R^6$ is $C_1$-$C_6$ alkyl. In some embodiments, $C_1$-$C_6$ alkyl is tert-butyl. In some embodiments, $R^5$ is tert-butyl.

In some embodiments of the compounds of Formula (VIIb), $R^3$ is bromo. In some embodiments, $R^6$ is selected from $C_1$-$C_6$ alkyl, $C_6$-$C_{12}$aryl, and —$CH_2C_6$-$C_{12}$aryl. In some embodiments, $R^4$ is —$OR^6$, and $R^5$ is $C_1$-$C_6$ alkyl. In some embodiments, $R^6$ is $C_1$-$C_6$ alkyl. In some embodiments, $C_1$-$C_6$ alkyl is tert-butyl. In some embodiments, $R^5$ is tert-butyl.

In some embodiments of the compounds of Formula (VIIb), $R^3$ is iodo. In some embodiments, $R^6$ is selected from $C_1$-$C_6$ alkyl, $C_6$-$C_{12}$aryl, and —$CH_2C_6$-$C_{12}$aryl. In some embodiments, $R^4$ is —$OR^6$, and $R^5$ is $C_1$-$C_6$ alkyl. In some embodiments, $R^6$ is $C_1$-$C_6$ alkyl. In some embodiments, $C_1$-$C_6$ alkyl is tert-butyl. In some embodiments, $R^5$ is tert-butyl.

Compounds of Formula (VIII)

Also disclosed herein are compounds of Formula (VIII)

(VIII)

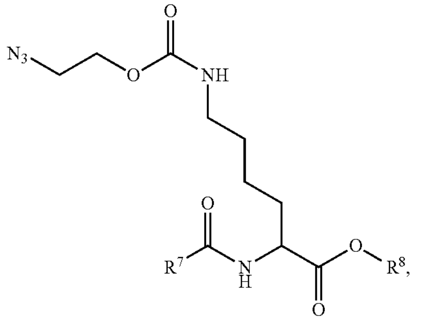

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl.

In some embodiments of the compounds of Formula (VIII), $R^7$ is —$OR^9$, and $R^8$ is $C_1$-$C_6$ alkyl. In some embodiments, $R^9$ is $C_1$-$C_6$ alkyl. In some embodiments, $C_1$-$C_6$ alkyl is tert-butyl. In some embodiments, $R^8$ is tert-butyl.

Also disclosed herein are compounds of Formula (VIIIa)

(VIIIa)

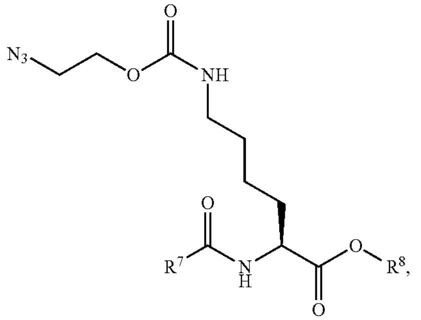

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl. In some embodiments, $R^7$ is —$OR^9$, and $R^8$ is $C_1$-$C_6$ alkyl.

In some embodiments of the compounds of Formula (VIIIa), $R^9$ is $C_1$-$C_6$ alkyl. In some embodiments, $C_1$-$C_6$ alkyl is tert-butyl. In some embodiments, $R^8$ is tert-butyl.

Also disclosed herein are compounds of Formula (VIIIb)

(VIIIb)

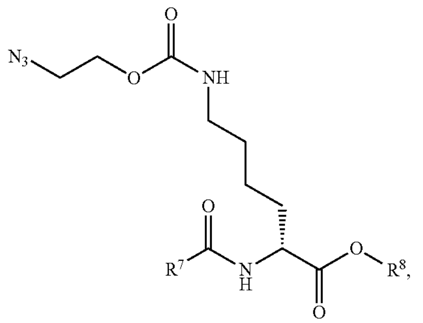

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl.

In some embodiments of the compounds of Formula (VIIIb), $R^7$ is —$OR^9$, and $R^8$ is $C_1$-$C_6$ alkyl. In some embodiments, $R^9$ is $C_1$-$C_6$ alkyl. In some embodiments, $C_1$-$C_6$ alkyl is tert-butyl. In some embodiments, $R^8$ is tert-butyl.

All compounds of Formula (I), (II), (III), (IV), (V), (VI), (VII), or (VIII), or any variation thereof as described herein, which exist in free base or acid form can be converted to their salts by treatment with the appropriate inorganic or organic base or acid by methods known to one skilled in the art. Salts of the compounds of the disclosure can be converted to their free base or acid form by standard techniques.

EXEMPLARY EMBODIMENTS

The present disclosure is further described by the following embodiments. The features of each of the embodiments are combinable with any of the other embodiments where appropriate and practical.

Embodiment P1. A compound of Formula (I), (I)

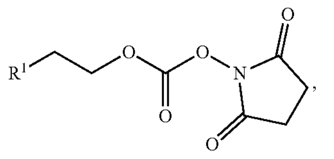

wherein $R^1$ is selected from chloro, bromo and iodo.

Embodiment P2. The compound of embodiment P1, wherein $R^1$ is chloro.

Embodiment P3. The compound of embodiment P1, wherein $R^1$ is bromo.

Embodiment P4. The compound of embodiment P1, wherein $R^1$ is iodo.

Embodiment P5. A compound of Formula (II), (II)

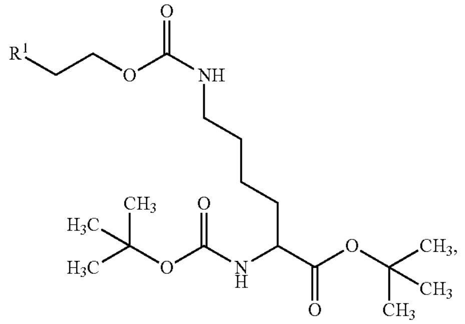

wherein $R^1$ is selected from chloro, bromo, and iodo.

Embodiment P6. The compound of embodiment P5, wherein $R^1$ is chloro.

Embodiment P7. The compound of embodiment P5, wherein $R^1$ is bromo.

Embodiment P8. The compound of embodiment P5, wherein $R^1$ is iodo.

Embodiment P9. A compound of Formula (IIa), (IIa)

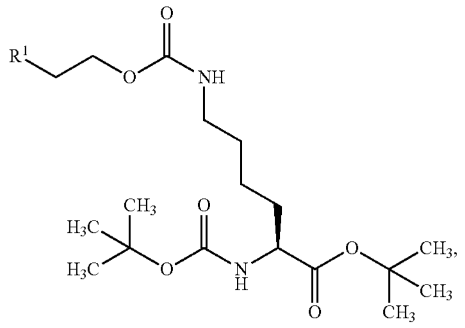

wherein $R^1$ is selected from chloro, bromo, and iodo.

Embodiment P10. The compound of embodiment P9, wherein $R^1$ is chloro.

Embodiment P11. The compound of embodiment P9, wherein $R^1$ is bromo.

Embodiment P12. The compound of embodiment P9, wherein $R^1$ is iodo.

Embodiment P13. A compound of Formula (IIb), (IIb)

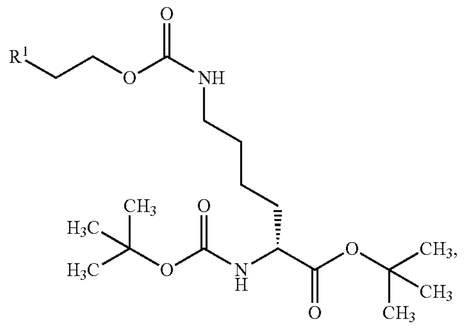

wherein $R^1$ is selected from chloro, bromo, and iodo.

Embodiment P14. The compound of embodiment P13, wherein $R^1$ is chloro.

Embodiment P15. The compound of embodiment P13, wherein $R^1$ is bromo.

Embodiment P16. The compound of embodiment P13, wherein $R^1$ is iodo.

Embodiment P17. A compound of Formula (III), (III)

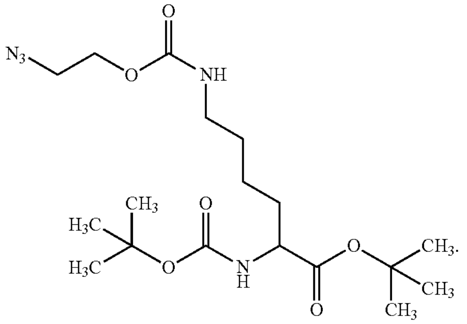

Embodiment P18. A compound of Formula (IIIa), (IIIa)

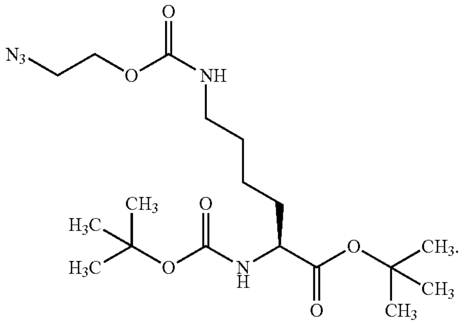

Embodiment P19. A compound of Formula (IIIb), (IIIb)

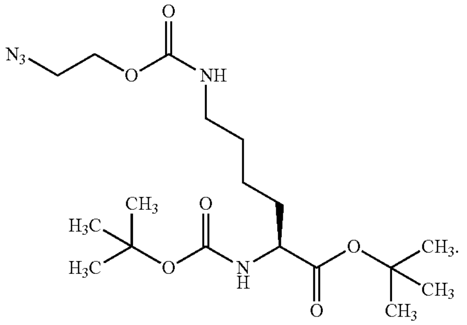

Embodiment P20. A method of preparing a compound of Formula (I), (I)

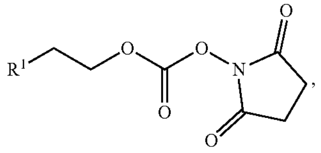

comprising allowing a compound of formula (IV), (IV)

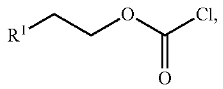

to react with N-hydroxysuccinimide to afford the compound of Formula (I), wherein, in each of the compounds of Formula (I) and (IV), $R^1$ is the same and is selected from chloro, bromo and iodo.

Embodiment P21. The method of embodiment P20, wherein $R^1$ is chloro.

Embodiment P22. The method of embodiment P20, wherein $R^1$ is bromo.

Embodiment P23. The method of embodiment P20, wherein $R^1$ is iodo.

Embodiment P24. The method of any one of embodiments P20 to P23, wherein the reaction of the compound of Formula (IV) with N-hydroxysuccinimide is performed in a solution comprising an aprotic solvent.

Embodiment P25. The method of embodiment P24, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P26. The method of embodiment P25, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane.

Embodiment P27. The method of embodiment P26, wherein the aprotic solvent is selected from acetonitrile, acetone, methyl ethyl ketone, dichloromethane, chloroform, tetrahydrofuran, and N,N-dimethylformamide.

Embodiment P28. The method of embodiment P27, wherein the aprotic solvent is acetonitrile.

Embodiment P29. The method of embodiment P27, wherein the aprotic solvent is acetone.

Embodiment P30. The method of embodiment P27, wherein the aprotic solvent is methyl ethyl ketone.

Embodiment P31. The method of embodiment P27, wherein the aprotic solvent is dichloromethane.

Embodiment P32. The method of embodiment P27, wherein the aprotic solvent is chloroform.

Embodiment P33. The method of embodiment P27, wherein the aprotic solvent is tetrahydrofuran.

Embodiment P34. The method of embodiment P27, wherein the aprotic solvent is N,N-dimethylformamide.

Embodiment P35. The method of any one of embodiments P24 to P34, wherein the solution further comprises a base.

Embodiment P36. The method of embodiment P35, wherein the base is selected from an organic base and an inorganic base.

Embodiment P37. The method of embodiment P36, wherein the organic base is selected from a heterocyclic base and a trialkylamine, or a mixture thereof.

Embodiment P38. The method of embodiment P36, wherein the heterocyclic base is an aromatic heterocyclic base or a non-aromatic heterocyclic base, or a mixture of an aromatic heterocyclic base and a non-aromatic heterocyclic base.

Embodiment P39. The method of embodiment P38, wherein the heterocyclic base is an aromatic heterocyclic base.

Embodiment P40. The method of embodiment P39, wherein the aromatic heterocyclic base is selected from pyridine, 1-alkylpyrrole, and 1-alkylimidazole, or a mixture thereof.

Embodiment P41. The method of embodiment P40, wherein the aromatic heterocyclic base is selected from pyridine, 1-methylpyrrole, and 1-methylimidazole, or a mixture thereof.

Embodiment P42. The method of embodiment P41, wherein the aromatic heterocyclic base is pyridine.

Embodiment P43. The method of embodiment P41, wherein the aromatic heterocyclic base is 1-methylpyrrole.

Embodiment P44. The method of embodiment P41, wherein the aromatic heterocyclic base is 1-methylimidazole.

Embodiment P45. The method of embodiment P38, wherein the heterocyclic base is a non-aromatic heterocyclic base.

Embodiment P46. The method of embodiment P38, wherein the non-aromatic heterocyclic base is selected from an N-alkylpyrrolidine, an N-alkylpiperidine, an N-alkylmorpholine, and a 1,4-dialkylpiperazine, or a mixture thereof.

Embodiment P47. The method of embodiment P46, wherein the non-aromatic heterocyclic base is an N-alkylpyrrolidine.

Embodiment P48. The method of embodiment P46, wherein the non-aromatic heterocyclic base is an N-alkylpiperidine.

Embodiment P49. The method of embodiment P46, wherein the non-aromatic heterocyclic base is an N-alkylmorpholine.

Embodiment P50. The method of embodiment P46, wherein the non-aromatic heterocyclic base is a 1,4-dialkylpiperazine.

Embodiment P51. The method of embodiment P46, wherein the non-aromatic heterocyclic base is selected from N-methylpyrrolidine, N-methylpiperidine, and N-methylmorpholine.

Embodiment P52. The method of embodiment P51, wherein the non-aromatic heterocyclic base is N-methylpyrrolidine.

Embodiment P53. The method of embodiment P51, wherein the non-aromatic heterocyclic base is N-methylpiperidine.

Embodiment P54. The method of embodiment P51, wherein the non-aromatic heterocyclic base is N-methylmorpholine.

Embodiment P55. The method of embodiment P37, wherein the organic base is a trialkylamine.

Embodiment P56. The method of embodiment P55, wherein the trialkylamine is selected from trimethylamine, triethylamine, tri-n-propylamine, tri-n-butylamine, tripentylamine, trihexylamine, and diisopropylethylamine.

Embodiment P57. The method of embodiment P56, wherein the trialkylamine is selected from trimethylamine, triethylamine, tri-n-propylamine, and diisopropylethylamine.

Embodiment P58. The method of embodiment P57, wherein the trialkylamine is selected from triethylamine, tri-n-propylamine, and diisopropylethylamine.

Embodiment P59. The method of embodiment P58, wherein the trialkylamine is triethylamine or diisopropylethylamine.

Embodiment P60. The method of embodiment P58, wherein the trialkylamine is triethylamine.

Embodiment P61. The method of embodiment P58, wherein the trialkylamine is diisopropylethylamine.

Embodiment P62. The method of embodiment P24, wherein $R^1$ is chloro and the aprotic solvent is acetonitrile.

Embodiment P63. The method of embodiment P62, wherein the solution further comprises a base.

Embodiment P64. The method of embodiment P63, wherein the base is selected from a trialkylamine.

Embodiment P65. The method of embodiment P64, wherein the trialkylamine is selected from trimethylamine, triethylamine, tri-n-propylamine, tri-n-butylamine, tripentylamine, trihexylamine, and diisopropylethylamine.

Embodiment P66. The method of embodiment P65, wherein the trialkylamine is selected from trimethylamine, triethylamine, tri-n-propylamine, and diisopropylethylamine.

Embodiment P67. The method of embodiment P66, wherein the trialkylamine is selected from triethylamine, tri-n-propylamine, and diisopropylethylamine.

Embodiment P68. The method of embodiment P67, wherein the trialkylamine is triethylamine or diisopropylethylamine.

Embodiment P69. The method of embodiment P68, wherein the trialkylamine is triethylamine.

Embodiment P70. The method of embodiment P68, wherein the trialkylamine is diisopropylethylamine.

Embodiment P71. The method of embodiment P24, wherein $R^1$ is bromo and the aprotic solvent is acetonitrile.

Embodiment P72. The method of embodiment P71, wherein the solution further comprises a base.

Embodiment P73. The method of embodiment P72, wherein the base is selected from a trialkylamine.

Embodiment P74. The method of embodiment P73, wherein the trialkylamine is selected from trimethylamine, triethylamine, tri-n-propylamine, tri-n-butylamine, tripentylamine, trihexylamine, and diisopropylethylamine.

Embodiment P75. The method of embodiment P74, wherein the trialkylamine is selected from trimethylamine, triethylamine, tri-n-propylamine, and diisopropylethylamine.

Embodiment P76. The method of embodiment P75, wherein the trialkylamine is selected from triethylamine, tri-n-propylamine, and diisopropylethylamine.

Embodiment P77. The method of embodiment P76, wherein the trialkylamine is triethylamine or diisopropylethylamine.

Embodiment P78. The method of embodiment P77, wherein the trialkylamine is triethylamine.

Embodiment P79. The method of embodiment P77, wherein the trialkylamine is diisopropylethylamine.

Embodiment P80. The method of embodiment P24, wherein $R^1$ is iodo and the aprotic solvent is acetonitrile.

Embodiment P81. The method of embodiment P80, wherein the solution further comprises a base.

Embodiment P82. The method of embodiment P81, wherein the base is selected from a trialkylamine.

Embodiment P83. The method of embodiment P82, wherein the trialkylamine is selected from trimethylamine, triethylamine, tri-n-propylamine, tri-n-butylamine, tripentylamine, trihexylamine, and diisopropylethylamine.

Embodiment P84. The method of embodiment P83, wherein the trialkylamine is selected from trimethylamine, triethylamine, tri-n-propylamine, and diisopropylethylamine.

Embodiment P85. The method of embodiment P84, wherein the trialkylamine is selected from triethylamine, tri-n-propylamine, and diisopropylethylamine.

Embodiment P86. The method of embodiment P85, wherein the trialkylamine is triethylamine or diisopropylethylamine.

Embodiment P87. The method of embodiment P86, wherein the trialkylamine is triethylamine.

Embodiment P88. The method of embodiment P86, wherein the trialkylamine is diisopropylethylamine.

Embodiment P89. A method of preparing a compound of Formula (II), (II)

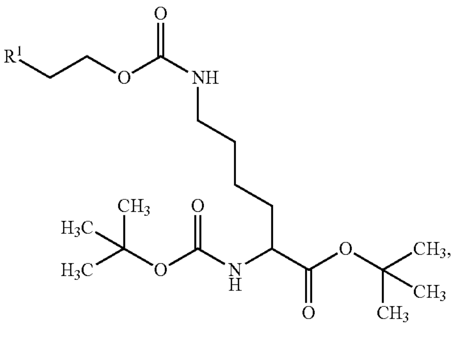

comprising allowing a compound of Formula (I), (I)

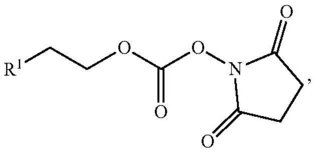

to react with a compound of Formula (V)

(V)

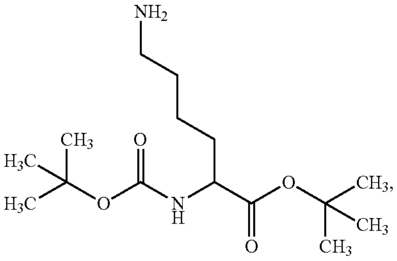

to afford the compound of Formula (II), wherein $R^1$ in each of the compounds of Formula (I) and (II) are the same and are selected from chloro, bromo and iodo.

Embodiment P90. The method of embodiment P89, wherein the reaction of the compound of Formula (V) with the compound of Formula (I) is performed in a solution comprising an aprotic solvent.

Embodiment P91. The method of embodiment P90, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P92. The method of embodiment P91, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane.

Embodiment P93. The method of embodiment P92, wherein the aprotic solvent is selected from acetonitrile, acetone, methyl ethyl ketone, dichloromethane, chloroform, tetrahydrofuran, and N,N-dimethylformamide.

Embodiment P94. The method of embodiment P93, wherein the aprotic solvent is acetonitrile.

Embodiment P95. The method of embodiment P93, wherein the aprotic solvent is acetone.

Embodiment P96. The method of embodiment P93, wherein the aprotic solvent is methyl ethyl ketone.

Embodiment P97. The method of embodiment P93, wherein the aprotic solvent is dichloromethane.

Embodiment P98. The method of embodiment P93, wherein the aprotic solvent is chloroform.

Embodiment P99. The method of embodiment P93, wherein the aprotic solvent is tetrahydrofuran.

Embodiment P100. The method of embodiment P93, wherein the aprotic solvent is N,N-dimethylformamide.

Embodiment P101. The method of any one of embodiments P89 to P100, wherein $R^1$ in each of the compounds of Formula (I) and (II) is chloro.

Embodiment P102. The method of any one of embodiments P89 to P100, wherein $R^1$ in each of the compounds of Formula (I) and (II) is bromo.

Embodiment P103. The method of any one of embodiments P89 to P100, wherein $R^1$ in each of the compounds of Formula (I) and (II) is iodo.

Embodiment P104. A method of preparing a compound of Formula (IIa), (IIa)

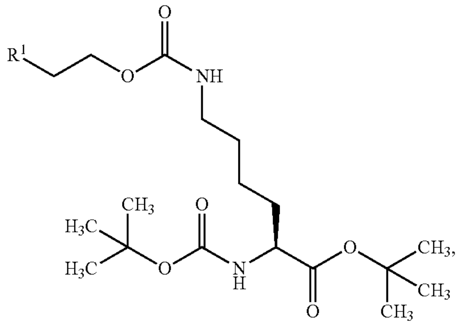

comprising allowing a compound of Formula (I), (I)

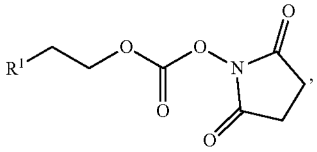

to react with a compound of Formula (Va)

(Va)

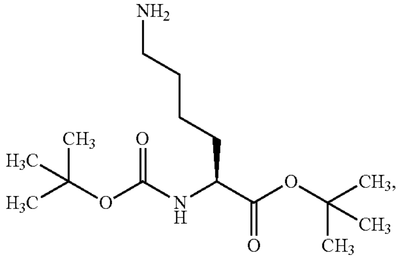

to afford the compound of Formula (IIa), wherein $R^1$ in each of the compounds of Formula (I) and (IIa) are the same and are selected from chloro, bromo and iodo.

Embodiment P105. The method of embodiment P104, wherein the reaction of the compound of Formula (Va) with the compound of Formula (I) is performed in a solution comprising an aprotic solvent.

Embodiment P106. The method of embodiment P105, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P107. The method of embodiment P106, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, and 1,4-dioxane.

Embodiment P108. The method of embodiment P107, wherein the aprotic solvent is selected from acetonitrile, acetone, methyl ethyl ketone, dichloromethane, chloroform, tetrahydrofuran, and N,N-dimethylformamide.

Embodiment P109. The method of embodiment P108, wherein the aprotic solvent is acetonitrile.

Embodiment P110. The method of embodiment P108, wherein the aprotic solvent is acetone.

Embodiment P111. The method of embodiment P108, wherein the aprotic solvent is methyl ethyl ketone.

Embodiment P112. The method of embodiment P108, wherein the aprotic solvent is dichloromethane.

Embodiment P113. The method of embodiment P108, wherein the aprotic solvent is chloroform.

Embodiment P114. The method of embodiment P108, wherein the aprotic solvent is tetrahydrofuran.

Embodiment P115. The method of embodiment P108, wherein the aprotic solvent is N,N-dimethylformamide.

Embodiment P116. The method of any one of embodiments P104 to P115, wherein $R^1$ in each of the compounds of Formula (I) and (IIa) is chloro.

Embodiment P117. The method of any one of embodiments P104 to P115, wherein $R^1$ in each of the compounds of Formula (I) and (IIa) is bromo.

Embodiment P118. The method of any one of embodiments P104 to P115, wherein $R^1$ in each of the compounds of Formula (I) and (IIa) is iodo.

Embodiment P119. A method of preparing a compound of Formula (IIb), (IIb)

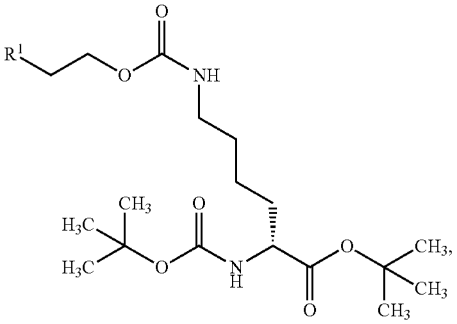

comprising allowing a compound of Formula (I), (I)

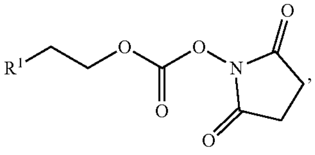

to react with a compound of Formula (Vb)

(Vb)

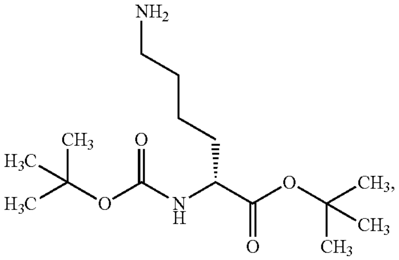

to afford the compound of Formula (IIb), wherein $R^1$ in each of the compounds of Formula (I) and (IIb) are the same and are selected from chloro, bromo and iodo.

Embodiment P120. The method of embodiment P119, wherein the reaction of the compound of Formula (Vb) with the compound of Formula (I) is performed in a solution comprising an aprotic solvent.

Embodiment P121. The method of embodiment P120, wherein the aprotic solvent is selected from acetonitrile, acetone, methyl ethyl ketone, dichloromethane, chloroform, tetrahydrofuran, N-methylpyrrolidine, dim ethyl sulfoxide, N,N-dimethylformamide, dimethylacetamide, 1,4-dioxane, sulfolane, gamma butyrolactone, pyrrolidones, 1-methyl-2- pyrrolidinone, methylpyrroline, ethylene glycol monomethyl ether, diethylene glycol monomethyl ether, PEG400 and polyethylene glycols.

Embodiment P122. The method of embodiment P121, wherein the aprotic solvent is selected from acetonitrile, acetone, methyl ethyl ketone, dichloromethane, chloroform, tetrahydrofuran, N-methylpyrrolidine, dim ethyl sulfoxide, N,N-dimethylformamide, dimethylacetamide, and 1,4-dioxane.

Embodiment P123. The method of embodiment P122, wherein the aprotic solvent is selected from acetonitrile, acetone, methyl ethyl ketone, dichloromethane, chloroform, tetrahydrofuran, and N,N-dimethylformamide.

Embodiment P124. The method of embodiment P123, wherein the aprotic solvent is acetonitrile.

Embodiment P125. The method of embodiment P123, wherein the aprotic solvent is acetone.

Embodiment P126. The method of embodiment P123, wherein the aprotic solvent is methyl ethyl ketone.

Embodiment P127. The method of embodiment P123, wherein the aprotic solvent is dichloromethane.

Embodiment P128. The method of embodiment P123, wherein the aprotic solvent is chloroform.

Embodiment P129. The method of embodiment P123, wherein the aprotic solvent is tetrahydrofuran.

Embodiment P130. The method of embodiment P123, wherein the aprotic solvent is N,N-dimethylformamide.

Embodiment P131. The method of any one of embodiments P119 to P130, wherein $R^1$ in each of the compounds of Formula (I) and (IIb) is chloro.

Embodiment P132. The method of any one of embodiments P119 to P130, wherein $R^1$ in each of the compounds of Formula (I) and (IIb) is bromo.

Embodiment P133. The method of any one of embodiments P119 to P130, wherein $R^1$ in each of the compounds of Formula (I) and (IIb) is iodo.

Embodiment P134. A method of preparing a compound of Formula (III), (III)

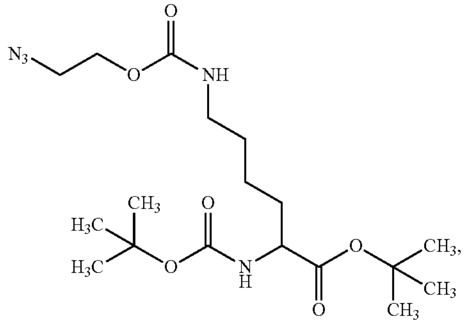

comprising allowing a compound of Formula (II), (II)

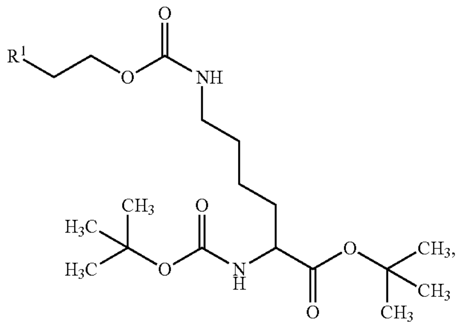

wherein $R^1$ is selected from chloro, bromo, and iodo, to react with an alkali azide salt to afford the compound of Formula (III).

Embodiment P135. The method of embodiment P134, wherein the alkali azide salt is selected from lithium azide, sodium azide, and potassium azide.

Embodiment P136. The method of embodiment P135, wherein the alkali azide salt is lithium azide.

Embodiment P137. The method of embodiment P135, wherein the alkali azide salt is sodium azide.

Embodiment P138. The method of embodiment P135, wherein the alkali azide salt is potassium azide.

Embodiment P139. The method of any one of embodiments P134 to P138, wherein the reaction of the compound of Formula (II) with the alkali azide salt is performed in a solution comprising an aprotic solvent, a protic solvent, or a mixture thereof.

Embodiment P140. The method of embodiment P139, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P141. The method of embodiment P140, wherein the aprotic solvent is selected from acetonitrile, tetrahydrofuran, N-methylpyrrolidine, dimethylsulfoxide, N,N-dimethylformamide, dimethylacetamide, and 1,4-dioxane.

Embodiment P142. The method of embodiment P141, wherein the aprotic solvent is selected from acetonitrile, tetrahydrofuran, N,N-dimethylformamide, and 1,4-dioxane.

Embodiment P143. The method of embodiment P142, wherein the aprotic solvent is acetonitrile.

Embodiment P144. The method of embodiment P142, wherein the aprotic solvent is tetrahydrofuran.

Embodiment P145. The method of embodiment P142, wherein the aprotic solvent is N,N-dimethylformamide.

Embodiment P146. The method of embodiment P142, wherein the aprotic solvent is 1,4-dioxane.

Embodiment P147. The method of embodiment P139, wherein the reaction of the compound of Formula (II) with the alkali azide salt is performed in a solution comprising a mixture of an aprotic solvent and a protic solvent.

Embodiment P148. The method of embodiment P147, wherein the solution further comprises a protic solvent.

Embodiment P149. The method of embodiment P148, wherein the protic solvent is selected from water and an alcohol.

Embodiment P150. The method of embodiment P149, wherein the protic solvent is water.

Embodiment P151. The method of embodiment P149, wherein the protic solvent is an alcohol.

Embodiment P152. The method of embodiment P151, wherein the alcohol is selected from methanol, ethanol, n-propanol, iso-propanol, n-butanol, iso-butanol, n-pentanol, and iso-pentanol.

Embodiment P153. The method of embodiment P152, wherein the alcohol is selected from methanol, ethanol, n-propanol, and iso-propanol.

Embodiment P154. The method of embodiment P139, wherein the solution comprises a mixture of water and 1,4-dioxane.

Embodiment P155. A method of preparing a compound of Formula (IIIa), (IIIa)

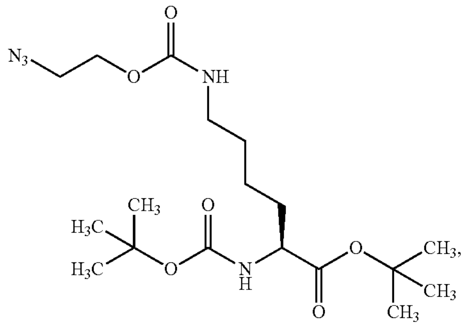

comprising allowing a compound of Formula (IIa), (IIa)

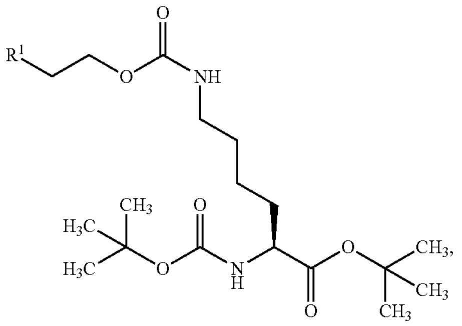

wherein $R^1$ is selected from chloro, bromo, and iodo, to react with an alkali azide salt to afford the compound of Formula (IIIa).

Embodiment P156. The method of embodiment P155, wherein the alkali azide salt is selected from lithium azide, sodium azide, and potassium azide.

Embodiment P157. The method of embodiment P156, wherein the alkali azide salt is lithium azide.

Embodiment P158. The method of embodiment P156, wherein the alkali azide salt is sodium azide.

Embodiment P159. The method of embodiment P156, wherein the alkali azide salt is potassium azide.

Embodiment P160. The method of any one of embodiments P155 to P159, wherein the reaction of the compound of Formula (IIa) with the alkali azide salt is performed in a solution comprising an aprotic solvent, a protic solvent, or a mixture thereof.

Embodiment P161. The method of embodiment P160, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P162. The method of embodiment P161, wherein the aprotic solvent is selected from acetonitrile, tetrahydrofuran, N-methylpyrrolidine, dimethylsulfoxide, N,N-dimethylformamide, dimethylacetamide, and 1,4-dioxane.

Embodiment P163. The method of embodiment P162, wherein the aprotic solvent is selected from acetonitrile, tetrahydrofuran, N,N-dimethylformamide, and 1,4-dioxane.

Embodiment P164. The method of embodiment P163, wherein the aprotic solvent is acetonitrile.

Embodiment P165. The method of embodiment P163, wherein the aprotic solvent is tetrahydrofuran.

Embodiment P166. The method of embodiment P163, wherein the aprotic solvent is N,N-dimethylformamide.

Embodiment P167. The method of embodiment P163, wherein the aprotic solvent is 1,4-dioxane.

Embodiment P168. The method of embodiment P160, wherein the reaction of the compound of Formula (IIa) with the alkali azide salt is performed in a solution comprising a mixture of an aprotic solvent and a protic solvent.

Embodiment P169. The method of any one of embodiments P161 to P168, wherein the solution further comprises a protic solvent.

Embodiment P170. The method of embodiment P169, wherein the protic solvent is selected from water and an alcohol.

Embodiment P171. The method of embodiment P170, wherein the protic solvent is water.

Embodiment P172. The method of embodiment P170, wherein the protic solvent is an alcohol.

Embodiment P173. The method of embodiment P172, wherein the alcohol is selected from methanol, ethanol, n-propanol, iso-propanol, n-butanol, iso-butanol, n-pentanol, and iso-pentanol.

Embodiment P174. The method of embodiment P173, wherein the alcohol is selected from methanol, ethanol, n-propanol, and iso-propanol.

Embodiment P175. The method of embodiment P160, wherein the solution comprises a mixture of water and 1,4-dioxane.

Embodiment P176. A method of preparing a compound of Formula (IIIb), (IIIb)

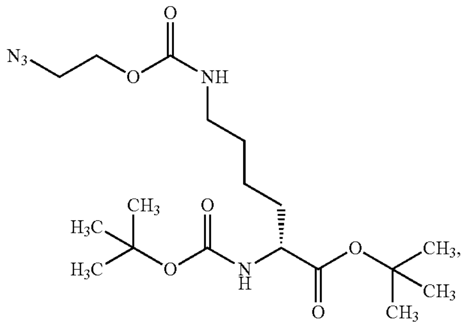

comprising allowing a compound of Formula (IIb), (IIb)

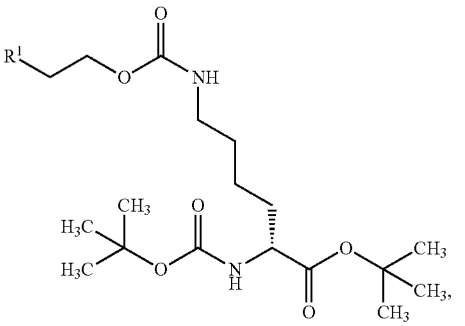

wherein $R^1$ is selected from chloro, bromo, and iodo, to react with an alkali azide salt to afford the compound of Formula (IIIb).

Embodiment P177. The method of embodiment P176, wherein the alkali azide salt is selected from lithium azide, sodium azide, and potassium azide.

Embodiment P178. The method of embodiment P177, wherein the alkali azide salt is lithium azide.

Embodiment P179. The method of embodiment P177, wherein the alkali azide salt is sodium azide.

Embodiment P180. The method of embodiment P177, wherein the alkali azide salt is potassium azide.

Embodiment P181. The method of any one of embodiments P176 to P180, wherein the reaction of the compound of Formula (IIb) with the alkali azide salt is performed in a solution comprising an aprotic solvent, a protic solvent, or a mixture thereof.

Embodiment P182. The method of embodiment P181, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P183. The method of embodiment P182, wherein the aprotic solvent is selected from acetonitrile, tetrahydrofuran, N-methylpyrrolidine, dimethylsulfoxide, N,N-dimethylformamide, dimethylacetamide, and 1,4-dioxane.

Embodiment P184. The method of embodiment P183, wherein the aprotic solvent is selected from acetonitrile, tetrahydrofuran, N,N-dimethylformamide, and 1,4-dioxane.

Embodiment P185. The method of embodiment P184, wherein the aprotic solvent is acetonitrile.

Embodiment P186. The method of embodiment P184, wherein the aprotic solvent is tetrahydrofuran.

Embodiment P187. The method of embodiment P184, wherein the aprotic solvent is N,N-dimethylformamide.

Embodiment P188. The method of embodiment P184, wherein the aprotic solvent is 1,4-dioxane.

Embodiment P189. The method of embodiment P181, wherein the reaction of the compound of Formula (IIb) with the alkali azide salt is performed in a solution comprising a mixture of an aprotic solvent and a protic solvent.

Embodiment P190. The method of any one of embodiments P182 to P188, wherein the solution further comprises a protic solvent.

Embodiment P191. The method of embodiment P190, wherein the protic solvent is selected from water and an alcohol.

Embodiment P192. The method of embodiment P191, wherein the protic solvent is water.

Embodiment P193. The method of embodiment P191, wherein the protic solvent is an alcohol.

Embodiment P194. The method of embodiment P193, wherein the alcohol is selected from methanol, ethanol, n-propanol, iso-propanol, n-butanol, iso-butanol, n-pentanol, and iso-pentanol.

Embodiment P195. The method of embodiment P194, wherein the alcohol is selected from methanol, ethanol, n-propanol, and iso-propanol.

Embodiment P196. The method of embodiment P195, wherein the solution comprises a mixture of water and 1,4-dioxane.

Embodiment P197. A method of preparing a compound of Formula (VI)

(VI)

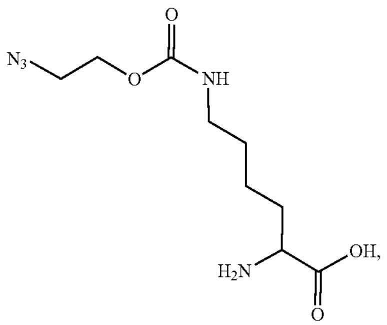

or a salt thereof, comprising allowing a compound of Formula (III)

(III)

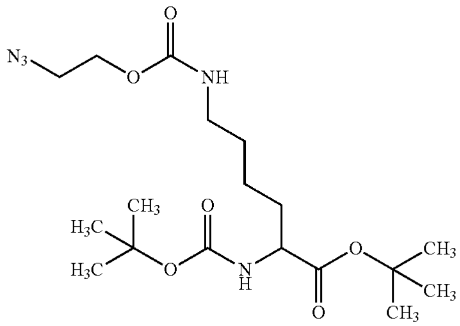

to react with an acid to afford a compound of Formula (VI).

Embodiment P198. The method of embodiment P197, wherein the reaction of the compound of Formula (III) with the acid is performed in a solution comprising an aprotic solvent, a protic solvent, or a mixture thereof.

Embodiment P199. The method of embodiment P198, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P200. The method of embodiment P199, wherein the aprotic solvent is selected from acetonitrile, tetrahydrofuran, N-methylpyrrolidine, dimethylsulfoxide, N,N-dimethylformamide, dimethylacetamide, and 1,4-dioxane.

Embodiment P201. The method of embodiment P200, wherein the aprotic solvent is selected from acetonitrile, tetrahydrofuran, N,N-dimethylformamide, and 1,4-dioxane.

Embodiment P202. The method of embodiment P201, wherein the aprotic solvent is acetonitrile.

Embodiment P203. The method of embodiment P201, wherein the aprotic solvent is tetrahydrofuran.

Embodiment P204. The method of embodiment P201, wherein the aprotic solvent is N,N-dimethylformamide.

Embodiment P205. The method of embodiment P201, wherein the aprotic solvent is 1,4-dioxane.

Embodiment P206. The method of embodiment P198, wherein the reaction of the compound of Formula (III) with the acid is performed in a solution comprising a mixture of a protic solvent and an aprotic solvent.

Embodiment P207. The method of any one of embodiments P198 to P206, wherein the protic solvent is water.

Embodiment P208. The method of embodiment P198, wherein the reaction of the compound of Formula (III) with the acid is performed in a solution comprising a mixture of 1,4-dioxane and water.

Embodiment P209. The method of any one of embodiments P197 to P208, wherein the acid is selected from phosphoric acid, hydrochloric acid, acetic acid, and trifluoroacetic acid.

Embodiment P210. The method of embodiment P209, wherein the acid is phosphoric acid.

Embodiment P211. The method of embodiment P209, wherein the acid is hydrochloric acid.

Embodiment P212. The method of embodiment P209, wherein the acid is acetic acid.

Embodiment P213. The method of embodiment P209, wherein the acid is trifluoroacetic acid.

Embodiment P214. A method of preparing a compound of Formula (VIa)

(VIa)

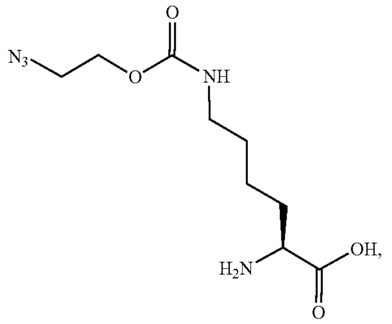

or a salt thereof, comprising allowing a compound of Formula (IIIa)

(IIIa)

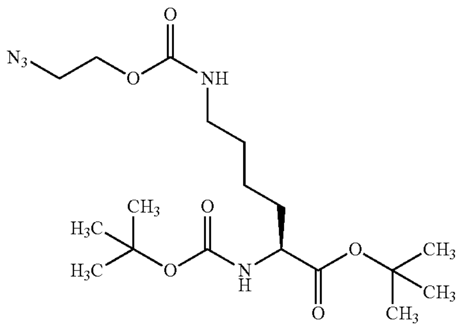

with an acid to afford a compound of Formula (VIa).

Embodiment P215. The method of embodiment P214, wherein the reaction of the compound of Formula (IIIa) with the acid is performed in a solution comprising an aprotic solvent, a protic solvent, or a mixture thereof.

Embodiment P216. The method of embodiment P215, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P217. The method of embodiment P216, wherein the aprotic solvent is selected from acetonitrile, tetrahydrofuran, N-methylpyrrolidine, dimethylsulfoxide, N,N-dimethylformamide, dimethylacetamide, and 1,4-dioxane.

Embodiment P218. The method of embodiment P217, wherein the aprotic solvent is selected from acetonitrile, tetrahydrofuran, N,N-dimethylformamide, and 1,4-dioxane.

Embodiment P219. The method of embodiment P218, wherein the aprotic solvent is acetonitrile.

Embodiment P220. The method of embodiment P218, wherein the aprotic solvent is tetrahydrofuran.

Embodiment P221. The method of embodiment P218, wherein the aprotic solvent is N,N-dimethylformamide.

Embodiment P222. The method of embodiment P218, wherein the aprotic solvent is 1,4-dioxane.

Embodiment P223. The method of embodiment P214, wherein the reaction of the compound of Formula (IIIa) with the acid is performed in a solution comprising a mixture of a protic solvent and an aprotic solvent.

Embodiment P224. The method of any one of embodiments P215 to P223, wherein the protic solvent is water.

Embodiment P225. The method of embodiment P215, wherein the reaction of the compound of Formula (IIIa) with the acid is performed in a solution comprising a mixture of 1,4-dioxane and water.

Embodiment P226. The method of any one of embodiments P214 to P225, wherein the acid is selected from phosphoric acid, hydrochloric acid, acetic acid, and trifluoroacetic acid.

Embodiment P227. The method of embodiment P226, wherein the acid is phosphoric acid.

Embodiment P228. The method of embodiment P226, wherein the acid is hydrochloric acid.

Embodiment P229. The method of embodiment P226, wherein the acid is acetic acid.

Embodiment P230. The method of embodiment P226, wherein the acid is trifluoroacetic acid.

Embodiment P231. A method of preparing a compound of Formula (VIb)

(VIb)

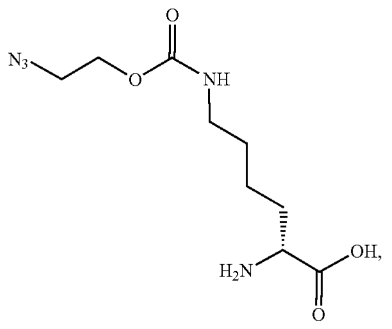

or a salt thereof, comprising allowing a compound of Formula (IIIb)

(IIIb)

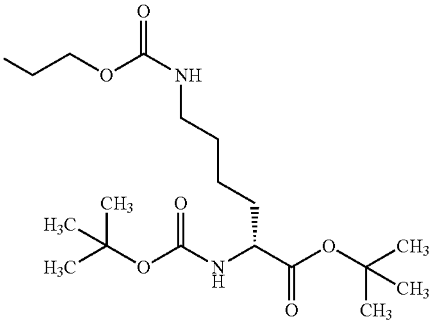

with an acid to afford a compound of Formula (VIb).

Embodiment P232. The method of embodiment P231, wherein the reaction of the compound of Formula (IIIb) with the acid is performed in a solution comprising an aprotic solvent, a protic solvent, or a mixture thereof.

Embodiment P233. The method of embodiment P232, wherein the aprotic solvent is selected from acetonitrile, acetone, methyl ethyl ketone, dichloromethane, chloroform, tetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Embodiment P234. The method of embodiment P233, wherein the aprotic solvent is selected from acetonitrile, tetrahydrofuran, N-methylpyrrolidine, dimethylsulfoxide, N,N-dimethylformamide, dimethylacetamide, and 1,4-dioxane.

Embodiment P235. The method of embodiment P234, wherein the aprotic solvent is selected from acetonitrile, tetrahydrofuran, N,N-dimethylformamide, and 1,4-dioxane.

Embodiment P236. The method of embodiment P235, wherein the aprotic solvent is acetonitrile.

Embodiment P237. The method of embodiment P235, wherein the aprotic solvent is tetrahydrofuran.

Embodiment P238. The method of embodiment P235, wherein the aprotic solvent is N,N-dimethylformamide.

Embodiment P239. The method of embodiment P235, wherein the aprotic solvent is 1,4-dioxane.

Embodiment P240. The method of embodiment P232, wherein the reaction of the compound of Formula (IIIb) with the acid is performed in a solution comprising a mixture of a protic solvent and an aprotic solvent.

Embodiment P241. The method of any one of embodiments P232 to P240, wherein the protic solvent is water.

Embodiment P242. The method of embodiment P232, wherein the reaction of the compound of Formula (IIIb) with the acid is performed in a solution comprising a mixture of 1,4-dioxane and water.

Embodiment P243. The method of any one of embodiments P231 to P242, wherein the acid is selected from phosphoric acid, hydrochloric acid, acetic acid, and trifluoroacetic acid.

Embodiment P244. The method of embodiment P243, wherein the acid is phosphoric acid.

Embodiment P245. The method of embodiment P243, wherein the acid is hydrochloric acid.

Embodiment P246. The method of embodiment P243, wherein the acid is acetic acid.

Embodiment P247. The method of embodiment P243, wherein the acid is trifluoroacetic acid.

Embodiment P248. A compound of Formula (VII)

(VII)

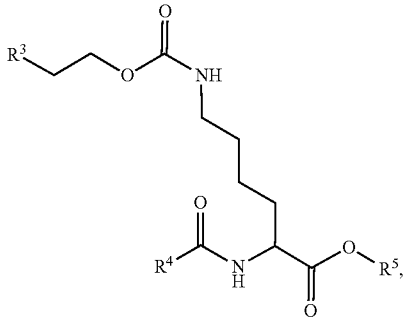

wherein:

$R^3$ is selected from chloro, bromo and iodo;

$R^4$ is selected from —$OR^6$, —$CF_3$, —$CH_2C_6$-$C_{12}$aryl, and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$ aryl.

Embodiment P249. The compound of embodiment P248, wherein $R^3$ is chloro.

Embodiment P250. The compound of embodiment P248, wherein $R^3$ is bromo.

Embodiment P251. The compound of embodiment P248, wherein $R^3$ is iodo.

Embodiment P252. The compound of embodiment P249, wherein $R^4$ is —$OR^6$, and $R^5$ is $C_1$-$C_6$ alkyl.

Embodiment P253. The compound of embodiment P252, wherein $R^6$ is $C_1$-$C_6$ alkyl.

Embodiment P254. The compound of embodiment P253, wherein $C_1$-$C_6$ alkyl is tert-butyl.

Embodiment P255. The compound of embodiment P254, wherein $R^5$ is tert-butyl.

Embodiment P256. The compound of embodiment P250, wherein $R^4$ is —$OR^6$, and $R^5$ is $C_1$-$C_6$ alkyl.

Embodiment P257. The compound of embodiment P256, wherein $R^6$ is $C_1$-$C_6$ alkyl.

Embodiment P258. The compound of embodiment P257, wherein $C_1$-$C_6$ alkyl is tert-butyl.

Embodiment P259. The compound of embodiment P258, wherein $R^5$ is tert-butyl.

Embodiment P260. The compound of embodiment P251, wherein $R^4$ is —$OR^6$, and $R^5$ is $C_1$-$C_6$ alkyl.

Embodiment P261. The compound of embodiment P260, wherein $R^6$ is $C_1$-$C_6$ alkyl.

Embodiment P262. The compound of embodiment P261, wherein $C_1$-$C_6$ alkyl is tert-butyl.

Embodiment P263. The compound of embodiment P262, wherein $R^5$ is tert-butyl.

Embodiment P264. A compound of Formula (VIIa)

(VIIa)

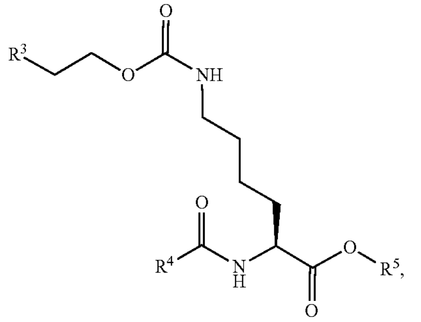

wherein:

$R^3$ is selected from chloro, bromo and iodo;

$R^4$ is selected from —$OR^6$, —$CF_3$, —$CH_2C_6$-$C_{12}$aryl, and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$aryl.

Embodiment P265. The compound of embodiment P264, wherein $R^3$ is chloro.

Embodiment P266. The compound of embodiment P264, wherein $R^3$ is bromo.

Embodiment P267. The compound of embodiment P264, wherein $R^3$ is iodo.

Embodiment P268. The compound of embodiment P265, wherein $R^4$ is —$OR^6$, and $R^5$ is $C_1$-$C_6$ alkyl.

Embodiment P269. The compound of embodiment P268, wherein $R^6$ is $C_1$-$C_6$ alkyl.

Embodiment P270. The compound of embodiment P269, wherein $C_1$-$C_6$ alkyl is tert-butyl.

Embodiment P271. The compound of embodiment P270, wherein $R^5$ is tert-butyl.

Embodiment P272. The compound of embodiment P266, wherein $R^4$ is —$OR^6$, and $R^5$ is $C_1$-$C_6$ alkyl.

Embodiment P273. The compound of embodiment P272, wherein $R^6$ is $C_1$-$C_6$ alkyl.

Embodiment P274. The compound of embodiment P273, wherein $C_1$-$C_6$ alkyl is tert-butyl.

Embodiment P275. The compound of embodiment P274, wherein $R^5$ is tert-butyl.

Embodiment P276. The compound of embodiment P267, wherein $R^4$ is —$OR^6$, and $R^5$ is $C_1$-$C_6$ alkyl.

Embodiment P277. The compound of embodiment P276, wherein $R^6$ is $C_1$-$C_6$ alkyl.

Embodiment P278. The compound of embodiment P277, wherein $C_1$-$C_6$ alkyl is tert-butyl.

Embodiment P279. The compound of embodiment P278, wherein $R^5$ is tert-butyl.

Embodiment P280. A compound of Formula (VIIb)

(VIIb)

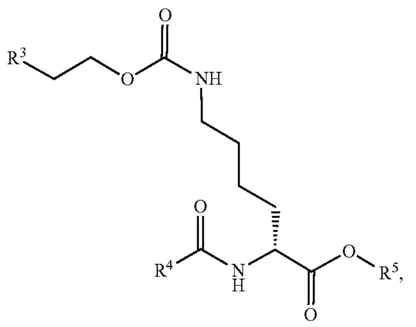

wherein:

$R^3$ is selected from chloro, bromo and iodo;

$R^4$ is selected from —$OR^6$, —$CF_3$, —$CH_2C_6$-$C_{12}$aryl and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$aryl.

Embodiment P281. The compound of embodiment P280, wherein $R^3$ is chloro.

Embodiment P282. The compound of embodiment P280, wherein $R^3$ is bromo.

Embodiment P283. The compound of embodiment P280, wherein $R^3$ is iodo.

Embodiment P284. The compound of embodiment P281, wherein $R^4$ is —$OR^6$, and $R^5$ is $C_1$-$C_6$ alkyl.

Embodiment P285. The compound of embodiment P284, wherein $R^6$ is $C_1$-$C_6$ alkyl.

Embodiment P286. The compound of embodiment P285, wherein $C_1$-$C_6$ alkyl is tert-butyl.

Embodiment P287. The compound of embodiment P286, wherein $R^5$ is tert-butyl.

Embodiment P288. The compound of embodiment P282, wherein $R^4$ is —$OR^6$, and $R^5$ is $C_1$-$C_6$ alkyl.

Embodiment P289. The compound of embodiment P288, wherein $R^6$ is $C_1$-$C_6$ alkyl.

Embodiment P290. The compound of embodiment P289, wherein $C_1$-$C_6$ alkyl is tert-butyl.

Embodiment P291. The compound of embodiment P290, wherein $R^5$ is tert-butyl.

Embodiment P292. The compound of embodiment P283, wherein $R^4$ is —$OR^6$, and $R^5$ is $C_1$-$C_6$ alkyl.

Embodiment P293. The compound of embodiment P292, wherein $R^6$ is $C_1$-$C_6$ alkyl.

Embodiment P294. The compound of embodiment P293, wherein $C_1$-$C_6$ alkyl is tert-butyl.

Embodiment P295. The compound of embodiment P294, wherein $R^5$ is tert-butyl.

Embodiment P296. A compound of Formula (VIII)

(VIII)

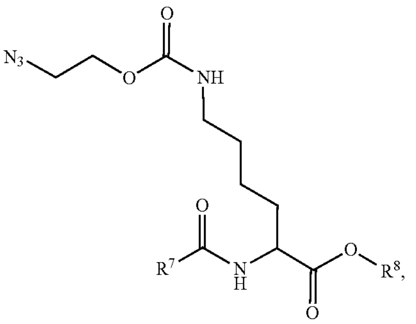

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl.

Embodiment P297. The compound of embodiment P281, wherein $R^7$ is —$OR^9$, and $R^8$ is $C_1$-$C_6$ alkyl.

Embodiment P298. The compound of embodiment P297, wherein $R^9$ is $C_1$-$C_6$ alkyl.

Embodiment P299. The compound of embodiment P298, wherein $C_1$-$C_6$ alkyl is tert-butyl.

Embodiment P300. The compound of embodiment P299, wherein $R^8$ is tert-butyl.

Embodiment P301. A compound of Formula (VIIIa)

(VIIIa)

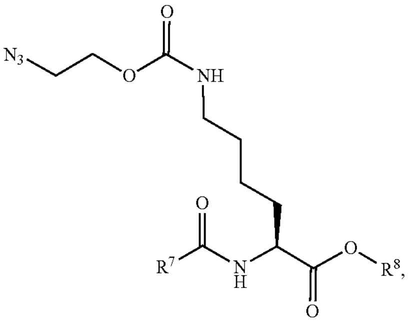

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl.

Embodiment P302. The compound of embodiment P301, wherein $R^7$ is —$OR^9$, and $R^8$ is $C_1$-$C_6$ alkyl.

Embodiment P303. The compound of embodiment P302, wherein $R^9$ is $C_1$-$C_6$ alkyl.

Embodiment P304. The compound of embodiment P303, wherein $C_1$-$C_6$ alkyl is tert-butyl.

Embodiment P305. The compound of embodiment P304, wherein $R^8$ is tert-butyl.

Embodiment P306. A compound of Formula (VIIIb)

(VIIIb)

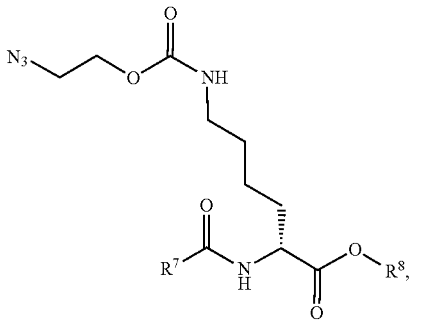

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl.

Embodiment P307. The compound of embodiment P306, wherein $R^7$ is —$OR^9$, and $R^8$ is $C_1$-$C_6$ alkyl.

Embodiment P308. The compound of embodiment P307, wherein $R^9$ is $C_1$-$C_6$ alkyl.

Embodiment P309. The compound of embodiment P308, wherein $C_1$-$C_6$ alkyl is tert-butyl.

Embodiment P310. The compound of embodiment P309, wherein $R^8$ is tert-butyl.

EXAMPLES

These examples are provided for illustrative purposes only and not to limit the scope of the claims provided herein.

Example 1

Preparation of 2-chloroethyl (2,5-dioxopyrrolidin-1-yl) carbonate

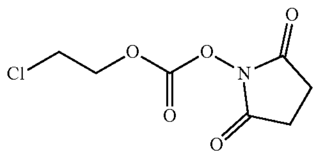 [SMILES: O=C(OCCCl)ON1C(=O)CCC1=O]

A 100 L jacketed reactor was equipped with an overhead stirrer, thermocouple probe and a reflux condenser. To the reactor was added about 750 grams of 2-chloroethyl chloroformate and about 15 liters of acetonitrile. The resulting reaction mixture was cooled to 0° C. and was agitated. To the mixture was added about 786 grams N-hydroxysuccinimide (1.3 equivalents), and then about 954 mL of triethylamine were added to the mixture over 1 hour while maintaining the temperature of the mixture at or below 3° C. for a period of about one hour, after which time the reaction mixture was allowed to gradually warm to ambient temperature. Reaction progress was monitored using thin-layer chromatography (TLC) employing ethyl acetate/hexanes (1/3 v/v) for developing the TLC plate and iodine vapor and a potassium permanganate staining solution were used for visualization. The reaction mixture was allowed to continue to stir until the presence of 2-chloroethyl chloroformate was no longer detected by TLC, after which time about 30 liters of deionized water were added resulting in a clear solution. To the reactor was then added about 12 liters of ethyl acetate and the resulting mixture was agitated. Following agitation, the layers of the mixture were allowed to separate, the bottom, aqueous layer was removed and placed in clean carboy containers, following which the remaining organic layer was removed and placed into clean carboy containers. The aqueous phase was returned to the reactor and to the reactor was added another portion of ethyl acetate (about 12 liters), the resulting mixture was agitated, after which the phases were allowed to separate. The bottom, aqueous phase was removed from the reactor and placed in clean carboy containers, after which the remaining organic phase was removed and placed into clean carboy containers. This process was repeated a third time, after which the remaining aqueous phases were discarded. Anhydrous magnesium sulfate was added to the organic layers, the mixture was stirred with a glass rod and the solution was allowed to stand for not less than an hour until they were deemed to be dry. The mixture was filtered through a medium-porosity filter and the remaining filter cake was washed with two volumes of ethyl acetate. The resulting mixture was concentrated on a rotary evaporator under reduced pressure until no more distillate was observed (maximum bath temperature 60° C.), after which about 1.8 liters of hexane were added to the remaining residue to form a solid. The solid was then filtered through a medium porosity filter, the remaining filter cake was washed with several volumes of hexane, and the remaining solid was then allowed to dry under reduced pressure to afford the title compound. $^1$H NMR (500 MHz, Chloroform-d) δ 4.56 (t, J=5.8, 5.8 Hz, 2H), 3.76 (t, J=5.8, 5.8 Hz, 2H), 2.85 (s, 4H).

Example 2

Preparation of $N^2$-[(1,1-dimethylethoxy)carbonyl]-L-lysine 1,1-dimethylethyl ester (Formula (Va))

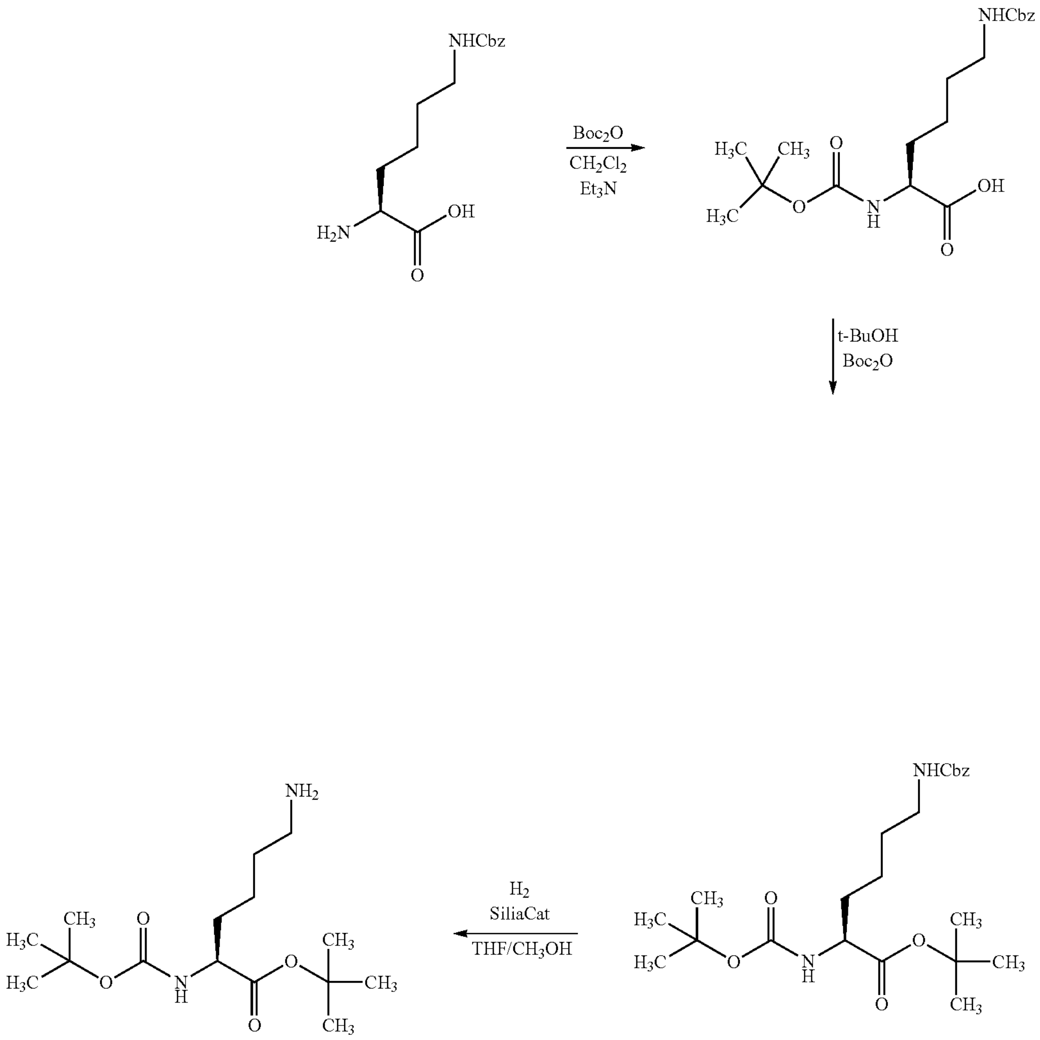

(Va)

$N^2$-[(1,1-dimethylethoxy)carbonyl]-$N^6$-[(phenylmethoxy)carbonyl]-L-lysine

A 100 L jacketed reactor was equipped with an overhead stirrer, thermocouple probe and a reflux condenser. To the reactor was added about 3.8 kilograms of $N^6$-[(phenylmethoxy)carbonyl]-L-lysine, about 40 liters of deionized water, and about 2.05 kilograms (1.1 equiv.) of potassium carbonate. In a separate container was added about 3.1 kilograms (1.05 equiv.) of di-tert-butyldicarbonate and about 16 liters of 1,4-dioxane. The di-tert-butyldicarbonate solution was then gradually added to the solution of $N^6$-[(phenylmethoxy)carbonyl]-L-lysine over 1 hour while the temperature of the reaction mixture was maintained at a temperature between about 20° C. and 25° C., and the resulting reaction mixture was stirred until less than 1% of the $N^6$-[(phenylmethoxy)carbonyl]-L-lysine material was determined to be present. The resulting mixture was concentrated under reduced pressure using a rotary evaporator, having a bath temperature of about 45° C., to a volume of approximately 20 liters, following which about 7 liters of deionized water were added. The pH of the resulting mixture was then adjusted to a pH of approximately 3 to 4 by the gradual addition of 1 N hydrochloric acid (approximately 22.4 liters). To the resulting mixture was added about 20 liters of ethyl acetate, the mixture was agitated, the phases were allowed to separate, the aqueous phase was separated and placed into clean containers and the remaining organic phase was placed into clean containers. The aqueous phase was returned to the reactor, an additional portion (about 20 liters) of ethyl acetate were added, the mixture was agitated, the phases were allowed to separate, and the aqueous and organic layers were separated. This process was repeated a second time, after which the aqueous phases were discarded. The combined organic phases were returned to the reactor, about 13 liters of 1 N hydrochloric acid were added, the resulting mixture was agitated, the phases were allowed to separate, and the aqueous phase was removed and discarded. To the remaining organic phase was added about 13 liters of deionized water, the resulting mixture was agitated, the layers were allowed to separate, and the aqueous layer was separated and discarded. The organic phase was added about 10 liters of saturated, aqueous sodium chloride, the mixture was agitated, the phases were allowed to separate, and the bottom aqueous phase was removed and discarded. Another portion of about 10 liters of sodium chloride were added, the mixture was agitated, the phases were allowed to separate, and the bottom aqueous phase was removed and discarded. To the remaining organic phase were added about 2 kilograms of anhydrous magnesium sulfate, the mixture was stirred with a glass rod and then allowed to stand for not less than an hour. The resulting mixture was filtered through a medium porosity filter and the filter cake was washed with several volumes of ethyl acetate. The resulting solution was concentrated on a rotary evaporator, having a bath temperature of about 45° C. (maximum bath temperature 60° C.), under reduced pressure until no further weight loss was observed to afford $N^2$-[(1,1-dimethylethoxy)carbonyl]-$N^6$-[(phenylmethoxy)carbonyl]-L-lysine as a solid. The resulting solid was dried, with occasional stirring of the solid, in a vacuum oven having an oven temperature of about 50° C. until loss on drying was less than about 0.2% per hour.

$N^2$-[(1,1-dimethylethoxy)carbonyl]-$N^6$-[(phenylmethoxy)carbonyl]-L-lysine 1,1-dimethylethyl ester A 100 L jacketed reactor was equipped with an overhead stirrer, thermocouple probe and a reflux condenser. To the reactor was added about 3.75 kilograms of $N^2$-[(1,1-dimethylethoxy)carbonyl]-$N^6$-[(phenylmethoxy)carbonyl]-L-lysine and about 22 liters of tert-butanol. The resulting mixture was allowed to stir at a temperature of from about 20° C. to about 23° C. until a clear solution was observed, after which about 2.85 kilograms (1.1 equiv.) of di-tert-butyl dicarbonate was added to the reactor and the resulting mixture was stirred at a temperature of from about 20° C. to about 25° C. until a clear solution was achieved, followed by the addition of about 290 grams (0.2 equiv.) of 4-dimethylaminopyridine. The resulting mixture was stirred for not less than about 1.5 hours at a temperature of from about 20° C. to about 24° C., and the reaction was monitored until less than about 1% of $N^2$-[(1,1-dimethylethoxy)carbonyl]-$N^6$-[(phenylmethoxy)carbonyl]-L-lysine remained, after which about 105 grams (0.1 equiv.) of 1,1-dimethyl-ethylenediamine were added, and the resulting mixture was stirred for not less than 15 minutes at a temperature of about 20° C. The reaction mixture was then cooled to a temperature of from about −2° C. to about 3° C. and about 40 liters of 0.5 molar aqueous hydrochloric acid and about 20 liters of ethyl acetate resulting in a mixture that was stirred, the phases were allowed to separate, and the aqueous and organic layers were separated and placed into clean containers. The aqueous phase was returned to the reactor to which about 20 liters of ethyl acetate were added, the mixture stirred, the phases were allowed to separate, and the aqueous phase was removed and was discarded. The combined organic phases were returned to the reactor, about 20 liters of a saturated sodium bicarbonate solution were added, the resulting mixture was agitated, the phases were allowed to separate, and the aqueous layer was removed and discarded. To the organic phase was added about 10 liters of an aqueous sodium chloride solution, the mixture was agitated, the phases were allowed to separate, and the phase aqueous phase was removed and discarded. About 2 kilograms of anhydrous magnesium sulfate were added to the organic layer, the mixture was stirred with a glass rod and was then allowed to sit for not less than lhour. The mixture was then filtered through a medium porosity filter, the filter cake was washed with several volumes of ethyl acetate and the resulting solution was concentrated under reduced pressure using a rotary evaporator, having a bath temperature of about 45° C. (maximum bath temperature of about 60° C.) until no further weight loss was observed to provide $N^2$-[(1,1-dimethylethoxy)carbonyl]-$N^6$-[(phenylmethoxy)carbonyl]-L-lysine 1,1-dimethylethyl ester as a solid. The resulting solid was dried in a vacuum oven having a temperature of about 50° C., with occasional stirring of the solid, until the loss on drying was determined to be less than about 0.2% per hour.

$N^2$-[(1,1-dimethylethoxy)carbonyl]-L-lysine 1,1-dimethylethyl ester (Formula (Va))

A jacketed, 100-liter, stainless steel pressure reactor was equipped with an overhead mechanical stirrer and hydrogen/nitrogen inlets. To the reactor were added about 4360 grams of $N^2$-[(1,1-dimethylethoxy)carbonyl]-$N^6$-[(phenylmethoxy)carbonyl]-L-lysine 1,1-dimethylethyl ester, about 600 grams of 10% palladium on carbon, and about 50 liters of tetrahydrofuran (THF). The reactor was then pressurized with nitrogen in the range of about 20 psi to 40 psi and the pressure was then vented. The pressurization/venting process with nitrogen was repeated three times, after which the reactor was pressurized with hydrogen in the range of about 20 psi to 40 psi, following which the pressure was vented. The pressurization/venting process with hydrogen was repeated three times, after the reactor was pressurized with about 40 psi of hydrogen. The reaction mixture was then heated to a temperature of from about 40° C. to about 60° C. and stirred. The progress of the reaction was monitored until less than about 1% of the $N^2$-[(1,1-dimethylethoxy)carbonyl]-$N^6$-[(phenylmethoxy)carbonyl]-L-lysine 1,1-dimethylethyl ester reactant was present, after which the mixture was allowed to cool and maintained at a temperature of from about 20° C. to 25° C. for not less than 4 hours. The reactor was then vented, pressurized with nitrogen and vented three times. The resulting mixture was filtered through a bed of Celite® that was slurried in THF using a medium porosity filter and the resulting filter cake was washed with several volumes of THF. The resulting organic phases were combined and concentrated under reduced pressure using a rotary evaporator until no further weight loss was observed (maximum bath temperature 60° C.) to afford $N^2$-[(1,1-dimethylethoxy)carbonyl]-L-lysine 1,1-dimethylethyl ester (Formula (Va)). $^1$H NMR (500 MHz, DMSO-d6) δ 7.06 (d, J=7.7 Hz, 1H), 3.77-3.69 (m, 1H), 2.62 (t, J=7.3, 7.3 Hz, 2H), 1.62-1.50 (m, 2H), 1.50-1.26 (m, 26H). Mass Spectrum positive ionization mode: m/z 303.4 (M+H).

Example 3

Preparation of $N^2$-[(1,1-dimethylethoxy)carbonyl]-L-lysine 1,1-dimethylethyl ester (Formula (Va))

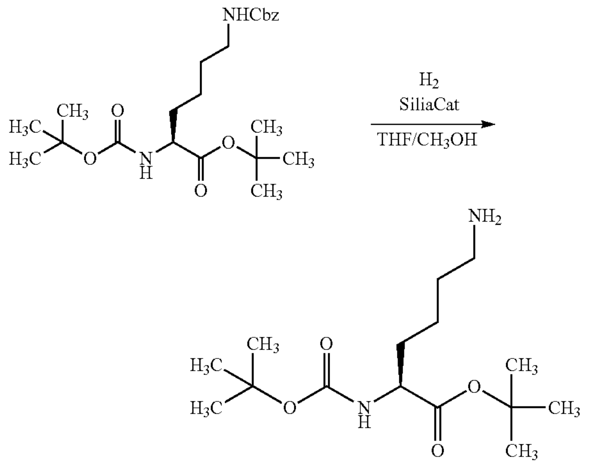

(Va)

A jacketed, 100-liter, stainless steel pressure reactor was equipped with an overhead mechanical stirrer hydrogen gas dispersion tube. To the reactor were added about 4.53 kilograms of $N^2$-[(1,1-dimethylethoxy)carbonyl]-$N^6$-[(phenylmethoxy)carbonyl]-L-lysine 1,1-dimethylethyl ester, about 15 liters of tetrahydrofuran (THF), about 15 liters of methanol, about 1.5 liters of glacial acetic acid, and about 1 kilogram of SiliaCat 10% palladium on carbon. The resulting mixture was stirred under nitrogen for about 15 minutes, after which the reactor was charged with hydrogen, the temperature of the heating jacket was adjusted to a temperature of from about 20° C. to about 25° C., and the resulting mixture was stirred until less than about 1% of the starting material remained. The resulting mixture was filtered through a medium porosity filter, while rising with tetrahydrofuran. The resulting solution was concentrated to a volume of about 6 to 7 liters using a rotary evaporator having a bath temperature of about 30° C., after which the remaining materials were transferred to a reactor, followed by the addition of about 8 liters of methyl tert-butyl ether. About 13 liters of aqueous sodium bicarbonate was added to the solution, the mixture was agitated, and the phases were separated. The aqueous phase was washed with another portion of about 4 liters (×2) of methyl tert-butyl ether, the mixture was agitated, and the phases were separated. The organic layer was washed with about 4 liters of saturated, aqueous sodium bicarbonate, and the layers were separated. The resulting organic layer was washed with about 4 liters of saturated, aqueous sodium chloride solution, the layers were separated, and about 1 kilogram of anhydrous magnesium sulfate was added to the organic layer. The mixture was allowed to stand for about an hour, after which time it was filtered using a medium porosity filter and the filter cake was washed with several portions of methyl tert-butyl ether. The resulting solution was concentrated using a rotary evaporator, having a bath temperature of about 35° C., to afford $N^2$-[(1,1-dimethylethoxy)carbonyl]-L-lysine 1,1-dimethylethyl ester (Formula (Va)) as a solid. The solid was dried in a vacuum oven having an oven temperature of about 35° C., with occasional stirring, until loss on drying was determined to be less than about 0.2% per hour. $^1$H NMR (500 MHz, DMSO-d6) δ 7.06 (d, J=7.7 Hz, 1H), 3.77-3.69 (m, 1H), 2.62 (t, J=7.3, 7.3 Hz, 2H), 1.62-1.50 (m, 2H), 1.50-1.26 (m, 26H). Mass Spectrum positive ionization mode: m/z 303.4 (M+H).

Example 4

Preparation of tert-butyl $N^2$-(tert-butoxycarbonyl)-$N^6$-((2-chloroethoxy)carbonyl)-L-lysinate

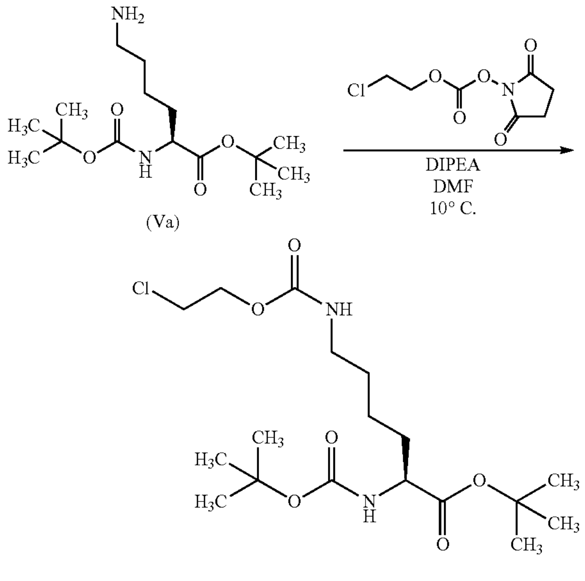

A 100-liter jacketed reactor was equipped with a reactor head, stir assembly, stir shaft, stir paddle, Teflon coated thermocouple and an overhead stirrer, and was placed under positive argon flow. To the reactor were added about 2.9 kg of $N^2$-[(1,1-dimethylethoxy)carbonyl]-L-lysine 1,1-dimethylethyl ester and about 19 liters of anhydrous N,N-dimethylformamide. The resulting mixture was cooled to 0° C. to 5° C. with stirring, followed by the addition of about 1.5 liters of diisopropylethyl amine. To the resulting mixture was gradually added solid about 2.11 kg of 2-chloroethyl (2,5-dioxopyrrolidin-1-yl) carbonate in portions, waiting about 10 minutes between the addition of each portion, while the internal temperature of the mixture was maintained at a temperature of between 2° C. and 7° C. Following the complete addition of the 2-chloroethyl (2,5-dioxopyrrolidin-1-yl) carbonate, the resulting mixture was allowed to stir at a temperature of between 2° C. and 7° C. for a minimum of 4 hours. Reaction progress was followed by determining by HPLC when the amount of $N^2$-[(1,1-dimethylethoxy)carbonyl]-L-lysine 1,1-dimethylethyl ester was less than about 1%. The mixture was then cooled to a temperature of between about −5° C. to about 0° C. and 12 liters of heptane were added, followed by the addition of about 12 liters of ethyl acetate. Into a separate vessel were prepared about 30 liters of a 0.5 molar aqueous hydrochloric acid solution by adding about 28.75 liters of water and about 1.25 liters of concentrated hydrochloric acid to the vessel, which was then stirred and allowed to cool to ambient temperature. About 30 liters of the 0.5 molar hydrochloric acid solution were then added to the reaction mixture in the other vessel, the resulting mixture was stirred, the temperature was adjusted to between about 15° C. and 25° C., stirring was continued for about 15 minutes, following which stirring was stopped and the phases were allowed to separate. The aqueous layer was separated, placed into separate containers and then placed into a 50-liter reactor. To the aqueous layer was added about 2 liters of heptane and 2 liters of ethyl acetate, the resulting mixture was stirred for 10 minutes, and the layers were then allowed to separate. The aqueous layer was separated and placed into separate containers. This process was repeated. The combined organic layers were transferred from the 50-liter reactor into the 100-liter reactor along with the remaining organic layer from the first separation and about 12 liters of water were then added, the mixture was stirred for 15 minutes, after which the layers were allowed to separate. To the remaining organic layers were added about 4 liters of saturated sodium chloride solution, the mixture was stirred, the layers were allowed to separate, and the aqueous layer was removed. This process was repeated with a second portion of 4 liters of saturated sodium chloride solution. To the remaining organic layer were added about 1.5 kg of anhydrous magnesium sulfate, the mixture was stirred and was then filtered through a medium frit funnel. The resulting solution was concentrated under reduced pressure using a rotary evaporator, and using polish-filtered ethyl acetate to complete the transfer from the reactor to the rotary evaporator vessel, while the bath temperature was set to 25° C., with a maximum bath temperature for this process of 40° C. To the remaining residue was added about 4 liters of acetonitrile, which was then removed under reduced pressure using a rotary evaporator. A second portion of about 4 liters of acetonitrile was added and removed under reduced pressure using a rotary evaporator. The remaining residue was transferred to a drying tray and was dried under reduced pressure in a vacuum oven set to a temperature of about 25° C. The solid in the drying tray was occasionally stirred and drying in the vacuum oven at about 25° C. was continued until loss on drying was determined to be less than about 0.2% per hour to afford tert-butyl $N^2$-(tert-butoxycarbonyl)-$N^6$-((2-chloroethoxy)carbonyl)-L-lysinate as a solid. $^1$H NMR (500 MHz, DMSO-d6) δ 7.24-7.16 (m, 1H), 7.02 (d, J=7.6 Hz, 1H), 4.08 (dd, J=5.7, 4.4 Hz, 2H), 3.76-3.69 (m, 1H), 3.50-3.44 (m, 2H), 2.94 (h, J=7.1, 7.1, 7.1, 7.1, 7.1 Hz, 2H), 1.63-1.47 (m, 3H), 1.37 (d, J=2.2 Hz, 22H), 1.30-1.22 (m, 2H), 1.19-1.11 (m, 1H). Mass Spectrum positive ionization mode: m/z 409.4 (M+H).

Example 5

Preparation of tert-butyl $N^6$-((2-azidoethoxy)carbonyl)-$N^2$-(tert-butoxycarbonyl)-L-lysinate (Formula (IIIa))

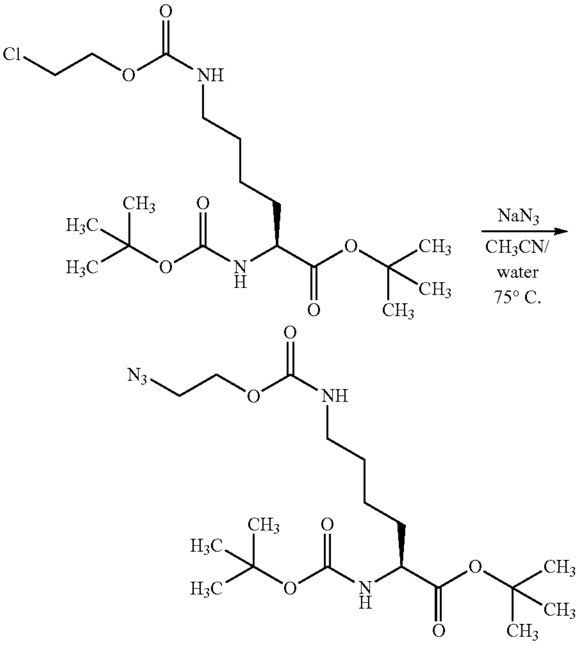

(IIIa)

A 100-liter jacketed reactor was equipped with a reactor head, stir assembly, stir shaft, stir paddle, Teflon coated thermocouple and an overhead stirrer, and was placed under positive argon flow. To the reactor were added about 3.75 kg of tert-butyl $N^2$-(tert-butoxycarbonyl)-$N^6$-((2-chloroethoxy) carbonyl)-L-lysinate and about 19 liters of acetonitrile. Into a separate reaction vessel were placed about 3 kg of sodium azide and about 19 liters of water, and the contents were stirred until the solids were dissolved. The sodium azide solution was then added to the solution of tert-butyl $N^2$-(tert-butoxycarbonyl)-$N^6$-((2-chloroethoxy)carbonyl)-L-lysinate, the resulting mixture was stirred and heated to a temperature of between about 70° C. to about 80° C. and stirring was continued for about 30 hours. The progress of the reaction was monitored by HPLC until it was determined that less than about 1% of tert-butyl N2-(tert-butoxycarbonyl)-N6-((2-chloroethoxy)carbonyl)-L-lysinate remained, after which the reaction mixture was allowed to cool to a temperature of between about 15° C. and 25° C., followed by the addition of about 12 liters of heptane and about 24 liters of ethyl acetate. The resulting mixture was allowed to stir for about 15 minutes, the layers were allowed to separate, and the aqueous layer was removed and discarded. An additional portion of water (about 5 liters) were added to the remaining organic layer, the mixture was stirred, the layers were allowed to separate, and the aqueous layer was separated and discarded. This process was repeated using an additional portion (about 5 liters) of water. To the organic layer was added 2 liters of saturated sodium chloride solution, the resulting mixture was stirred for 15 about minutes, the layers were allowed to separate, and the aqueous layer was separated and discarded. This process was repeated using an additional portion (about 2 liters) of saturated sodium chloride solution. The remaining organic layers was filtered using a medium frit funnel and the solvents were removed under reduced pressure using a rotary evaporator having a bath temperature of 25° C. and a maximum bath temperature of 40° C. The remaining solid was transferred to a drying tray and was dried in a vacuum oven that was purged with argon and set to a temperature of 35° C. Drying was continued until loss of drying was determined to be less than about 0.2% per hour, followed by at least 2 additional hours of drying to afford tert-butyl $N^6$-((2-azidoethoxy) carbonyl)-$N^2$-(tert-butoxycarbonyl)-L-lysinate (Formula (IIIa)) as a solid. $^1$H NMR (500 MHz, DMSO-d6) δ 7.20 (t, J=5.7, 5.7 Hz, 1H), 7.02 (d, J=7.5 Hz, 1H), 4.15-4.05 (m, 2H), 3.72 (td, J=8.3, 7.8, 5.1 Hz, 1H), 3.50-3.45 (m, 2H), 3.01-2.89 (m, 2H), 1.60-1.49 (m, 2H), 1.44-1.24 (m, 25H), 1.19-1.12 (m, 1H). Mass Spectrum positive ionization mode: m/z 416.7 (M+H).

Example 6

Preparation of $N^6$-((2-azidoethoxy)carbonyl)-L-lysine (Formula (VIa))

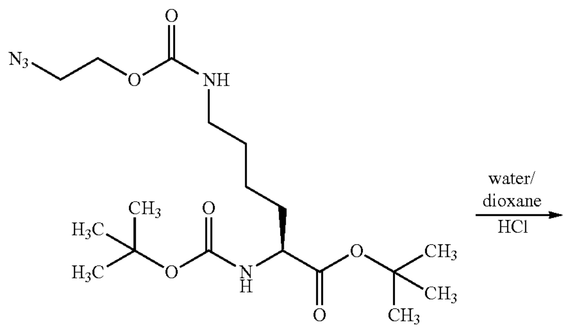

(IIIa)

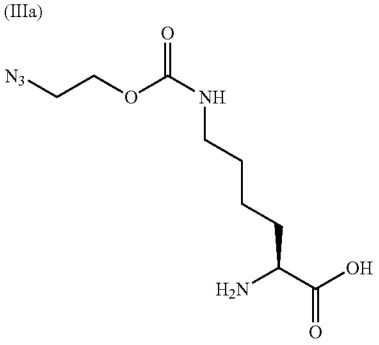

(VIa)

A 100-liter jacketed reactor was equipped with a reactor head, stir assembly, stir shaft, stir paddle, Teflon coated thermocouple an overhead stirrer, and a gas trap, and was placed under positive argon flow. To the reactor were added about 4.53 kg of tert-butyl $N^6$-((2-azidoethoxy)carbonyl)-$N^2$-(tert-butoxycarbonyl)-L-lysinate (Formula (IIIa)) and 11 liters of 1,4-dioxane. The resulting mixture was stirred and cooled to a temperature of between 5° C. and 10° C. To the mixture was added about 9.4 liters of concentrated hydrochloric acid in 0.5 liter portions over 2 hours so the temperature of the reaction mixture was maintained between about 10° C. and 15° C. Following the complete addition of the hydrochloric acid solution, the mixture was stirred and was gradually warmed to a temperature of between 42° C. to 47° C. and stirring was continued at that temperature for about 3 hours. The reaction mixture was then cooled to a temperature of between about 15° C. to about 25° C. and was then filtered through a medium frit funnel into separate containers. About 6 to 7 liters of the solvents were removed under reduced pressure using a rotary evaporator having a bath temperature of about 30° C., with a maximum bath temperature of about 35° C. The remaining contents of the rotary evaporator were transferred to a jacketed reactor, stirred and the temperature was adjusted to a temperature of about 15° C. to about 25° C. Between about 0.9 liters and 1.2 liters of aqueous ammonium hydroxide were slowly added to the reactor to maintain an internal temperature of less than 40° C. until a pH of between about 7 and 8 was achieved. The resulting suspension was cooled to a temperature of between about 5° C. and 10° C., after which time the solid was collected using a medium frit funnel, rinsed with about 3 liters of water, and excess water was removed from the filter cake using a latex dam. The resulting solid was then transferred to drying trays and was dried in a vacuum oven under argon purge with the oven temperature set at 35° C. The solid was allowed to continue to dry under reduced pressure, with occasional stirring until loss of drying was determined to be less than about 0.2% per hour, after which it was allowed to continue to dry for an additional 2 hours to afford $N^6$-((2-azidoethoxy)carbonyl)-L-lysine (Formula (VIa)). $^1$H NMR (500 MHz, Deuterium Oxide) δ 4.12 (t, J=4.8 Hz, 2H), 3.94 (t, J=6.3 Hz, 1H), 3.43-3.37 (m, 2H), 3.04 (t, J=6.7 Hz, 2H), 1.93-1.75 (m, 2H), 1.49-1.38 (m, 2H), 1.38-1.26 (m, 2H). Mass Spectrum positive ionization mode: m/z 260.3 (M+H).

Example 7

Modified Preparation of 2-chloroethyl (2,5-dioxopyrrolidin-1-yl) carbonate

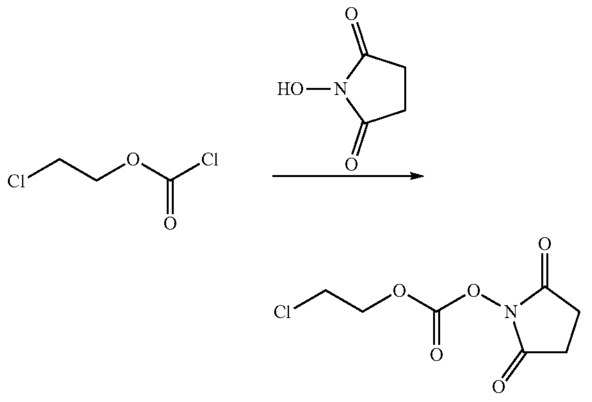

The preparation of 2-chloroethyl (2,5-dioxopyrrolidin-1-yl) carbonate according to Example 1 was modified to facilitate industrial large-scale synthesis. In particular, modifications were made to reduce reaction and work-up volumes, and to replace drying the organic phase with $MgSO_4$ with azeo-distillations for drying. This was achieved, in part, by using 2-methyltetrahydrofuran (2-MeTHF) as the reaction solvent.

A 1 L, 3-neck jacketed reaction flask was equipped with overhead stirring, temperature control (TC), and addition funnel (60 mL) with a nitrogen inlet to a bubbler. The flask was flushed with nitrogen and charged with 2-chloroethyl chloroformate (40.0 g, 0.280 mol), 2-Me-THF (512.8 g), and N-hydroxysuccinimide (41.9 g, 0.364 mol). The stirred mixture was cooled to −4° C. Triethylamine (36.8 g, 0.364 mol) was added slowly over 37 minutes, maintaining the temperature≤1° C. A thick precipitate formed during the addition. The temperature was adjusted to 11° C. over 1 h, and the mixture was stirred at 11° C. for 1 hour. The temperature was adjusted to 6° C., and water (399 g) was added slowly over 16 minutes, maintaining the temperature≤10° C. All solids dissolved during the water addition to provide a 2-liquid phase mixture. The mixture was stirred at 10-11° C. for 40 minutes. Stirring was stopped and the lower phase (aqueous) was removed. The water content of the organic phase was measured by KF (4.670%). The reaction flask was equipped for vacuum distillation: short path distillation head with receiving flask in an acetone/dry ice bath, house vacuum with bleed valve. The vacuum distillation was started. The jacket temperature was adjusted from 10 to 35° C. at the start of the distillation. The distillation was stopped when the pot volume was reduced to 200 mL. The pot temperature range during distillation was 11-21° C. (KF of hazy pot solution was found to be 4.908%). Next, 2-Me-THF (400 mL, 337.2 g) was added to the pot. The solvent was distilled under reduced vacuum until the pot volume was reduced to 200 mL. The pot temperature range during distillation was 31-27° C. A precipitate formed at the end of the distillation (KF of pot supernatant was found to be 0.550%). The temperature was adjusted to 21° C. and the thin slurry was stirred for 30 minutes. N-heptane (400 mL, 273.4 g) was added slowly over 10 minutes, and the resulting slurry was stirred at 21° C. for 16 h. The slurry was filtered (9 cm Buchner funnel, Whatman qualitative 1 paper) and rinsed forward with n-heptane (2×100 mL, 2×67 g). The wet cake was dried to constant weight (−30 inHg, 20° C., 1 h) to provide 56.12 g of the title compound as a solid (90.5%).

Example 8

Alternate Preparation of tert-butyl $N^2$-(tert-butoxycarbonyl)-$N^6$-((2-chloroethoxy)carbonyl)-L-lysinate

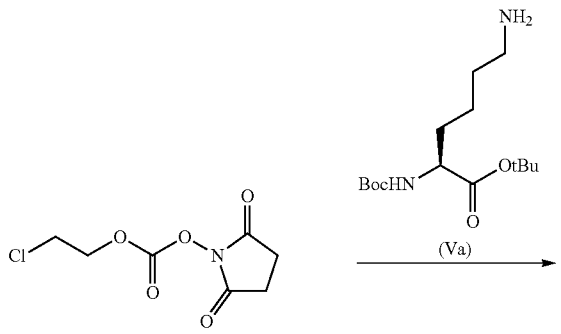

-continued

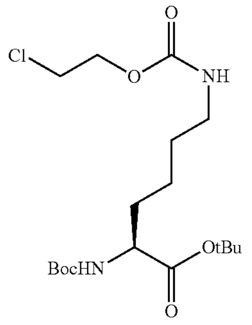

The preparation of tert-butyl $N^2$-(tert-butoxycarbonyl)-$N^6$-((2-chloroethoxy)carbonyl)-L-lysinate according to Example 4 was modified to facilitate industrial large-scale synthesis. This was achieved, in part, by using 2-MeTHF as the reaction solvent, followed by solvent exchange for acetonitrile and subsequently telescoping the reaction to the next step.

A 500 mL, 3-neck jacketed reaction flask containing (S)-tert-butyl 6-amino-2-(tert-butoxycarbonylamino) hexanoate (Formula (Va)) (approximately 49.3 mmol) as a crude solution in 2-MeTHF was equipped with overhead stirring, TC, and addition funnel (60 mL) with a nitrogen inlet to a bubbler. The stirred solution was cooled to 6° C. Next, 2-chloroethyl (2,5-dioxopyrrolidin-1-yl) carbonate (10.9 g, 49.2 mmol) was added in one portion, resulting in a temperature increase to 14° C. The solution was cooled to 9° C. and diisopropylethylamine (DIPEA) (6.70 g, 51.8 mmol) was added via addition funnel over 2 minutes, rinsing forward with 2-Me-THF (1.5 g). The jacket temperature was ramped from 5 to 20° C. over 1 h. The temperature was adjusted to 18° C., and acetic acid solution (5 wt % in $H_2O$, 90 g) was added slowly over 5 minutes, maintaining the temperature≤20° C. The mixture was stirred at 20-22° C. for 15 minutes. The lower aqueous phase was removed and discarded (pH~5, 102.6 g). The organic phase was stirred with $Na_2CO_3$ solution (5 wt % in $H_2O$, 90 g) for 15 minutes. The lower aqueous phase was removed and discarded (pH~10, 101.3 g). The organic phase was stirred with water (90 g) for 15 minutes. The lower aqueous phase was removed and discarded (pH 8-9, 104.1 g). The dark organic phase was polish filtered (0.2 um Polycap PTFE membrane filter via FMI pump), rinsing forward with 2-Me-THF (2×42 g). The solvent was vacuum distilled (jacket temperature of 45° C.) until the pot volume was reduced to 100 mL (pot temperature range of 44-32° C.). Acetonitrile (200 mL, 157.0 g) was added and the solvent was vacuum distilled (jacket temperature of 45° C.) until the pot volume was reduced to 100 mL (pot temperature range of 44 to 28° C.). The temperature was adjusted to 20° C. The solution containing the title compound was directly carried forward to the next step.

Example 9

Alternate Preparation of tert-butyl $N^6$-((2-azidoethoxy)carbonyl)-$N^2$-(tert-butoxycarbonyl)-L-lysinate (Formula (IIIa))

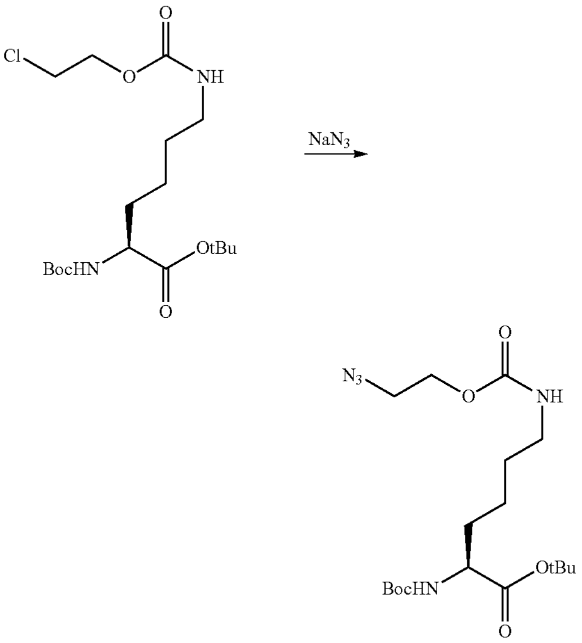

(IIIa)

The preparation of tert-butyl $N^6$-((2-azidoethoxy)carbonyl)-$N^2$-(tert-butoxycarbonyl)-L-lysinate (Formula (IIIa)) according to Example 5 was modified to facilitate industrial large-scale synthesis. This was achieved, in part, by replacing drying the organic phase with $MgSO_4$ with azeo-distillations for drying.

A 500 mL 3-neck jacketed reaction flask containing tert-butyl $N^2$-(tert-butoxycarbonyl)-$N^6$-((2-chloroethoxy)carbonyl)-L-lysinate (approximately 20.1 g, 49.3 mmol) as a crude solution in acetonitrile was equipped with overhead stirring, temperature control (TC), an addition funnel (60 mL), and a nitrogen inlet connected to a bubbler. The reactor jacket was set to 25° C. Sodium azide (14.4 g, 220 mmol) was dissolved in deionized water (101 mL) at 25° C. in a 250 mL Erlenmeyer flask. The sodium azide solution was charged into the reactor in one portion, creating a slight endotherm (+1° C.). The jacket temperature was set to 80° C. Once the internal temperature reached 75° C., the reaction was stirred for no less than (NLT) 20 h. The reactor jacket was set to 25° C. Ethyl acetate (120 mL) was charged into the reactor, followed by addition of n-heptane (60 mL). The reaction mixture was stirred at 25° C. for NLT 20 min. The phases were separated for NLT 15 min. The lower aqueous phase was removed and stored into a tared polypropylene bottle (119.1 g). The organic phase was charged back into the reactor along with $H_2O$ (30 mL). The mixture was stirred at 25° C. for NLT 20 min. The phases were then separated for NLT 15 min. The lower aqueous phase was removed and stored into a tared polypropylene bottle (36.3 g). The organic phase was charged back into the reactor along with $H_2O$ (30 mL), and the mixture was stirred at 25° C. for NLT 20 min. The phases were separated for NLT 15 min. The lower aqueous phase was removed and stored into a tared polypropylene bottle (36.7 g). The organic phase was charged back into the reactor along with $H_2O$ (30 mL). The mixture was stirred at 25° C. for NLT 20 min. The phases were separated for NLT 15 min. The lower aqueous phase was removed and stored into a tared polypropylene bottle (35.2 g). The organic phase was charged back into the reactor along with brine (17.9 g). The mixture was stirred at 25° C. for NLT 20 min. The phases were separated for NLT 15 min. The lower aqueous phase was removed and stored into a tared polypropylene bottle (21.4 g). The organic phase was charged back into the reactor along with brine (17.9 g). The mixture was stirred at 25° C. for NLT 20 min. The phases were separated for NLT 15 min. The lower aqueous phase was removed and stored into a tared polypropylene bottle. (11.51 g). The organic phase was charged back into the reactor and the jacket set to 45° C. Next, the solvent was stripped down to approximately 100 mL. 1,4-Dioxane (200 mL, 207 g) was charged into the reactor and the solution was distilled again under vacuum to approximately 100 mL. The brown organic phase was polish filtered (0.2 μm Polycap PTFE membrane filter via FMI pump), and rinsed forward with 1,4-dioxane (2×103 g). The jacket was set to 65° C. and the solvent was stripped down to ~100 mL. Next, the jacket was set to 25° C. The 1,4-dioxane solution containing the title compound was directly carried forward to the next step.

Example 10

Accelerating Rate Calorimetry (ARC) Studies of tert-butyl azidoethoxy)carbonyl)-$N^2$-(tert-butoxycarbonyl)-L-lysinate (Formula (IIIa))

In order to assess the safety of handling $N^6$-((2-azidoethoxy)carbonyl)-$N^2$-(tert-butoxycarbonyl)-L-lysinate (Formula (IIIa)), accelerating rate calorimetry (ARC) studies were performed. ARC data provide insight into the potential thermal hazard associated with the formation of $N^6$-((2-azidoethoxy)carbonyl)-$N^2$-(tert-butoxycarbonyl)-L-lysinate (Formula (IIIa)), which involves the use of high temperature (~80° C.) over 20 h of reaction time.

Experimental Objective

The ARC test determines the onset of any self-accelerating exothermic activity and gas generation in a chemical system under the pseudo-adiabatic conditions normally encountered during large-scale manufacturing and/or transportation. ARC uses the data to determine the enthalpy of a reaction or decomposition and find the maximum temperature rise should cooling or stirring fail during a critical stage of processing.

The ARC test was performed in a sample bomb (10 $cm^3$) connected at the top to a pressure transducer. The sample was sealed inside the adiabatic bomb enclosure, and the bomb enclosure was contained within the safety chamber of the apparatus. A thermocouple was situated on the wall of the bomb. The adiabatic enclosure consisted of two types of heaters: (i) radiant heaters used to heat the sample to its onset temperature and (ii) heaters used to control the adiabatic environment. When heat output is detected from the sample, these heaters maintain the adiabatic environment by accurately matching the oven temperature to the sample temperature. A very accurate control system is used to detect very small changes in reaction mass temperature and thus the adiabatic control is very efficient. The calorimeter was housed inside a robust chamber capable of withstanding rupture of the bomb that may occur with extremely high rate decomposing or detonating materials.

Results

Tests were undertaken in the ARC in "heat-wait-search" (HWS) mode. This involved heating the sample in regular temperature steps (e.g., 10° C.) and leaving the sample to equilibrate at this temperature for a set period. The control system then searched for any slight temperature increase due to exothermic activity. If the temperature rise detected throughout the searching period was less than 0.02 K·min$^{-1}$, the cycle was repeated until exothermic activity was detected. The ARC control system switched into adiabatic mode when a rate of temperature increase above 0.02 K·min$^{-1}$ was detected. The sample heaters were then used to control the environment of the bomb at the same temperature as the bomb itself.

A sample of $N^6$-((2-azidoethoxy)carbonyl)-$N^2$-(tert-butoxycarbonyl)-L-lysinate (Formula (IIIa) was tested using the HWS mode in the ARC under adiabatic conditions. The experimental parameters for the study are summarized in Table 1.

TABLE 1

Experimental parameters for ARC study of $N^6$-((2-azidoethoxy)carbonyl)-$N^2$-(tert-butoxycarbonyl)-L-lysinate (Formula (IIIa).

| | |
|---|---|
| Test Atmosphere | Air |
| Total Sample weight | 3.08 g |
| Bomb type | Titanium |
| Bomb weight | 7.39 g |
| Bomb heat capacity | 0.585 J · g$^{-1}$ · K$^{-1}$ |
| Sample heat capacity (estimate) | 2.10 J · g−1 · K−1 * |
| Phi Factor | 1.668 |
| Slope sensitivity | 0.02° C. min$^{-1}$ |
| End temperature | 380.0° C. |
| Wait time | 5 minutes |
| Pressure trip | 150.0 bar · g |
| Self-heating rate trip | 1000 K · min$^{-1}$ |
| Pressure Drop Trip | 20 bar · g |

* The heat capacity value is an estimation that is the average of most common organic compounds.

During the test, two self-heat exotherms were observed (Tables 2 and 3). The major exotherm started at an onset temperature of 160.5° C., leading to pressure rise and temperature increase. The maximum self-heat rate recorded was 2.098 K/min at 211.5° C., while the maximum pressure rate was 2.756 bar/min at 208.5° C. The total heat of the two exotherms was relatively mild at 236.0 J/g. At about 380° C., the pressure reached the trip point set at 150 bar, where the experiment was forced to stop, before reaching the target final temperature of 400° C.

TABLE 2

Summary of ARC data for $N^6$-((2-azidoethoxy)carbonyl)-$N^2$-(tert-butoxycarbonyl)-L-lysinate (Formula (IIIa).

| Paramater | Value | Units | 1st Exotherm | 2nd Exotherm |
|---|---|---|---|---|
| Mass of sample: | 3.0795 | grams | 3.08 | 3.08 |
| Heat capacity of sample: | 2.1000 | J/(gm * K) | 2.10 | 2.10 |
| Mass of bomb: | 7.3889 | grams | 7.39 | 7.39 |
| Heat capacity of bomb: | 0.5850 | J/(gm * K) | 0.59 | 0.59 |
| Phi factor (Φ): | 1.6684 | | 1.6684 | 1.6684 |
| Onset temperature of exotherm: | | ° C. | 100.14 | 160.48 |
| Final temperature of exotherm: | | ° C. | 100.79 | 227.19 |
| ΔT: | | ° C. | 0.65 | 66.71 |
| ΔT adiabatic: | | ° C. | 1.08 | 111.29 |
| ΔH reaction: | −235.99 | Joule/gram | −2.27 | −233.71 |

TABLE 3

| ARC data for $N^6$-((2-azidoethoxy)carbonyl)-$N^2$-(tert-butoxycarbonyl)-L-lysinate (Formula (IIIa)). | |
|---|---|
| Maximum temperature of test | 379.2° C. |
| Maximum self-heating rate of test | 2.10 K $min^{-1}$ |
| Temperature at maximum self-heat rate | 211.50° C. |
| Maximum pressure of test | 157.1 Bar gauge |
| Maximum pressure rate of test | 2.756 Bar $min^{-1}$ |
| Temperature at maximum pressure rate | 208.5° C. |
| Exotherm 1 | |
| Onset of exothermic activity | 100.14° C. |
| End of exothermic activity | 100.79° C. |
| Adiabatic Temperature Rise (phi corrected) | 1.08° C. |
| Heat of reaction (exothermic) | −2.27 J · $g^{-1}$ |
| Exotherm 2 | |
| Onset of exothermic activity | 160.48° C. |
| End of exothermic activity | 227.19° C. |
| Adiabatic Temperature Rise (phi corrected) | 111.29° C. |
| Heat of reaction (exothermic) | −233.71 J · $g^{-1}$ |
| Total heat released during the ARC test (all exotherms) | −235.98 J · $g^{-1}$ |

Figure 2:
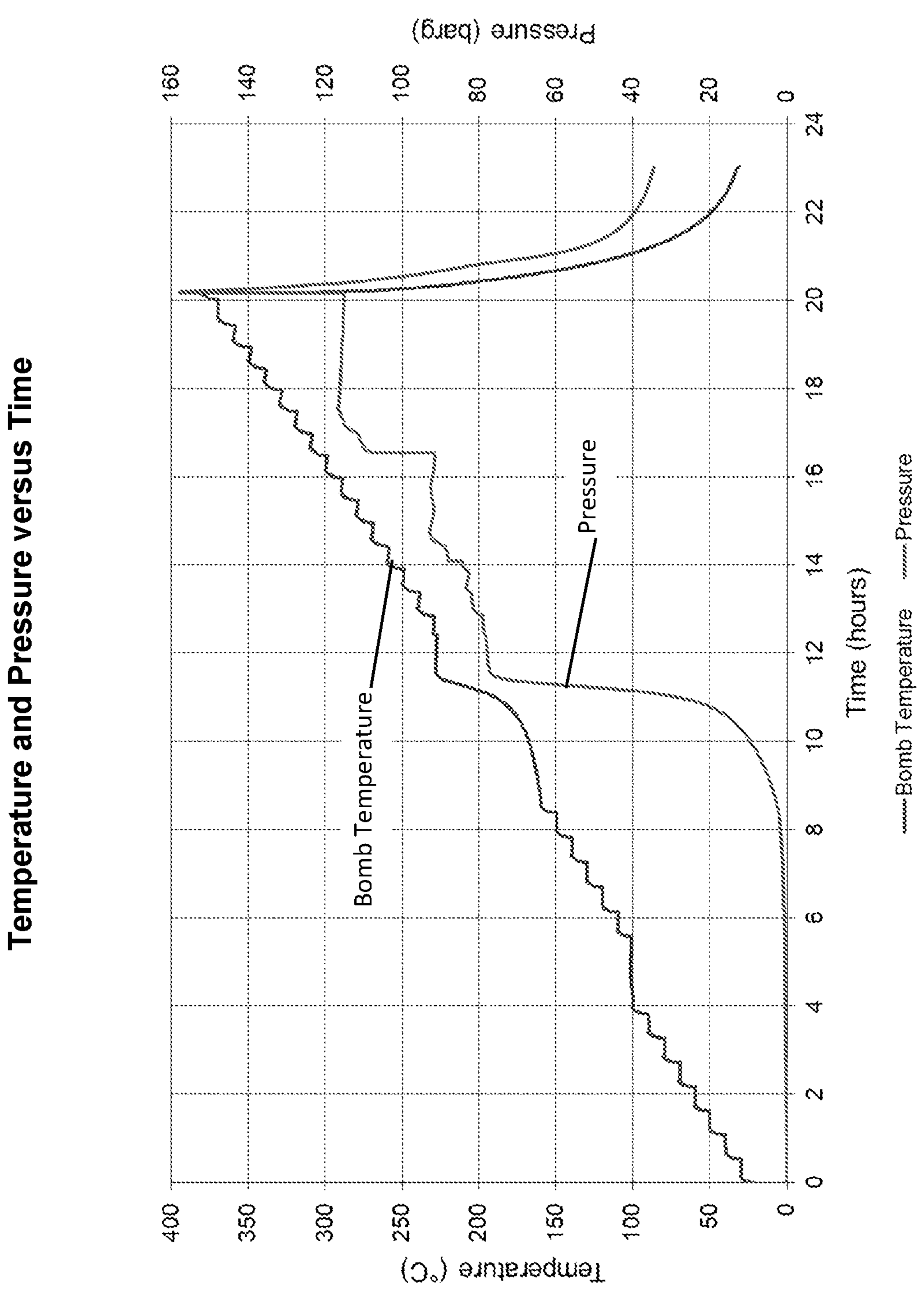
FIG. 2 shows graphs of temperature and pressure versus time of $N^6$-((2-azidoethoxy)carbonyl)-$N^2$-(tert-butoxycarbonyl)-L-lysinate (Formula (IIIa) for the ARC study described in Example 10.
Figure 3:
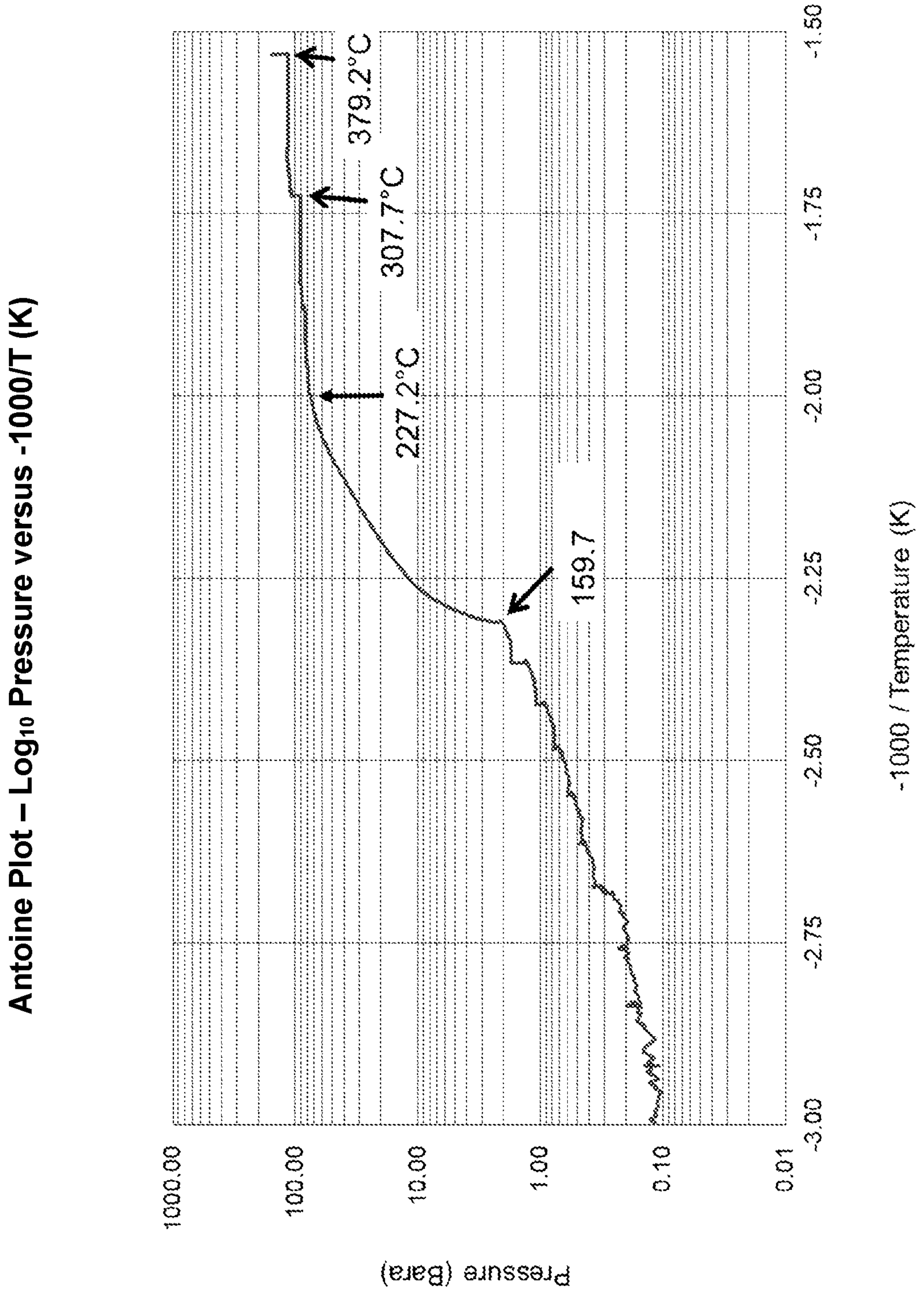
FIG. 3 shows an Antoine plot of $N^6$-((2-azidoethoxy)carbonyl)-$N^2$-(tert-butoxycarbonyl)-L-lysinate (Formula (IIIa) for the ARC study described in Example 10.

Plots of self-heat and pressure rate versus temperature plots are shown in FIG. 1, and temperature and pressure versus time plots are shown in FIG. 2. The Antoine plot shown in FIG. 3 shows that the pressure deviates from Antoine behavior at about 59.7° C., 227.2° C., 307.7° C., and 379.2° C. 35.5 Bar gauge of non-condensable gas remained in the bomb after completion of the test and cooling to near ambient temperature at 30.7° C.

Time to Maximum Rate

Test data obtained from the ARC can be used to estimate the self-accelerating decomposition temperature of a sample (J. K. Wilberforce, "The Use of the Accelerating Rate calorimeter to determine the SADT of organic peroxides," Columbia Scientific Industries, Milton Keynes; Harold G. Fisher and David D. Goetz, "Determination of self-accelerating decomposition temperature using the accelerating rate calorimeter," *J. Loss Prev. Process Ind.*, 1991, Vol 4., 305-316). Time to maximum rate (TMR) is defined as the amount of time that is needed for a reaction to reach its maximum self-heating rate or pressure rate in a thermal runaway reaction. TMR data was extracted from the phi factor corrected test data and a plot of Ln(TMR) against −1000/T was generated (FIG. 4).

Figure 4:
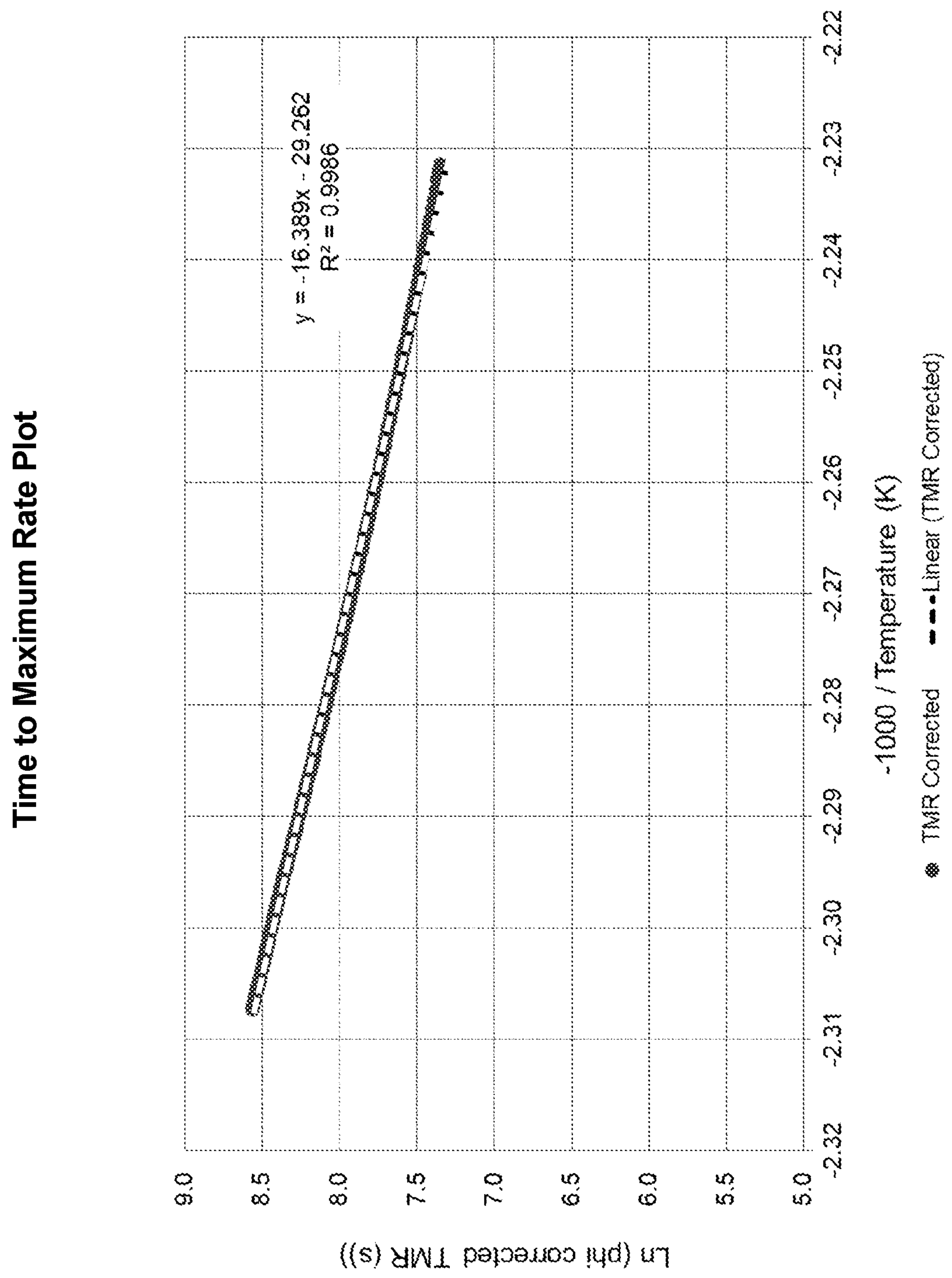
FIG. 4 shows a time to maximum rate plot of $N^6$-((2-azidoethoxy)carbonyl)-$N^2$-(tert-butoxycarbonyl)-L-lysinate (Formula (IIIa) for the ARC study described in Example 10.

The following equation was taken from FIG. 4 to allow the determination of the time to maximum rate as a function of temperature:

$$\mathrm{Ln}(\mathrm{TMR}(s))=-16.389*(-1000/(T(K)))-29.262$$

Figure 5:
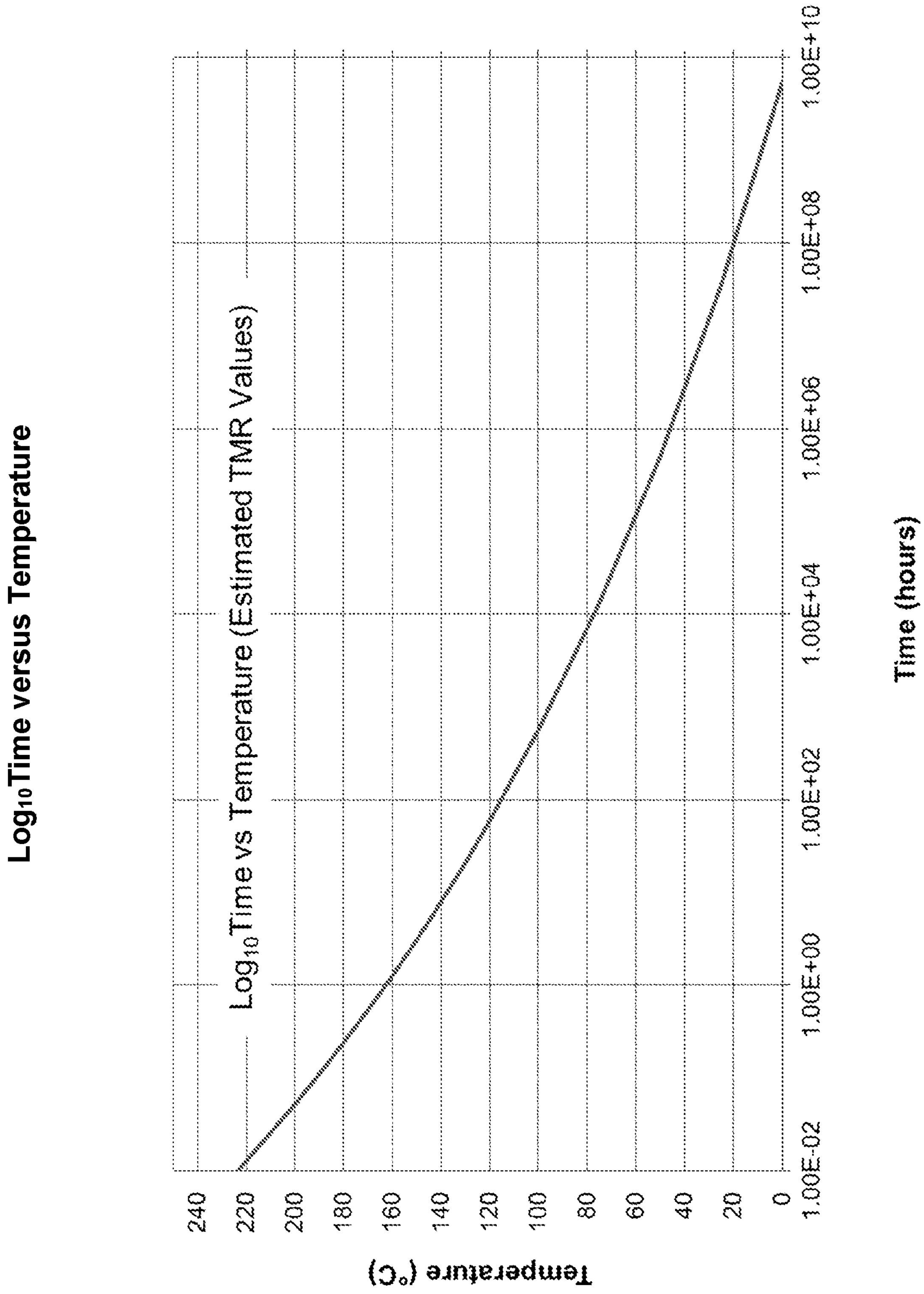
FIG. 5 shows a plot of time (logarithmic scale) versus temperature of $N^6$-((2-azidoethoxy)carbonyl)-$N^2$-(tert-butoxycarbonyl)-L-lysinate (Formula (IIIa) for the ARC study described in Example 10.

The TMR increases as the batch temperature decreases. The measured exotherm was used to estimate the TMR. The results are provided only as a reference, as it is based on a single ARC test and not a detailed kinetic study (FIG. 5). The time to maximum rate results are summarized in Table 4.

TABLE 4

TMR data for $N^6$-((2-azidoethoxy)carbonyl)-$N^2$-(tert-butoxycarbonyl)-L-lysinate (Formula (IIIa)).

| Temperature (° C.) | Hours |
|---|---|
| 122.0 | 48.3 |
| 129.0 * | 23.5 |
| 140.0 | 7.9 |
| 160.0 ** | 1.3 |

* At 129.0° C., the time to maximum rate (TMR) is ~24 hours. TMR24 is a good basis for safety but is dependent on the process conditions.
** Onset temperature of $2^{nd}$ exotherm.

The data demonstrate that there is no significant thermal hazard in preparing $N^6$-((2-azidoethoxy)carbonyl)-$N^2$-(tert-butoxycarbonyl)-L-lysinate (Formula (IIIa)) according to the reactions described herein.

Example 11

Alternate Preparation of $N^6$-((2-azidoethoxy)carbonyl)-L-lysine (Formula (VIa))

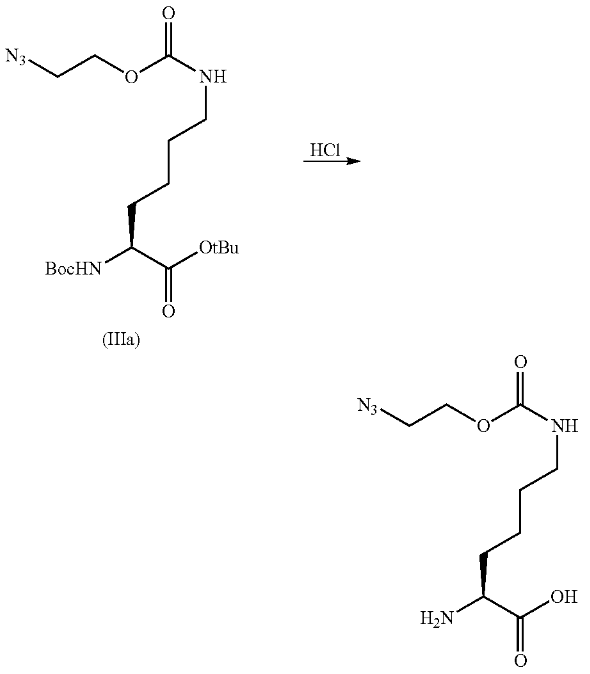

(IIIa)

(VIa)

The preparation of $N^6$-((2-azidoethoxy)carbonyl)-L-lysine (Formula (VIa)) according to Example 6 was modified to facilitate industrial large-scale synthesis. This was achieved, in part, by adjusting the pH of the solution to improve precipitation of the title compound.

A 500 mL 3-neck jacketed reaction flask containing tert-butyl azidoethoxy)carbonyl)-$N^2$-(tert-butoxycarbonyl)-L-lysinate (Formula (IIIa)) (approximately 20.4 g, 49.3 mmol) as a crude solution in 1,4-dioxane was equipped with overhead stirring, temperature control (TC), an addition funnel (60 mL), and a nitrogen inlet connected to a bubbler. The reactor jacket was set to 10° C. Once contents temperature was stable at 10.3° C., concentrated hydrochloric acid (61.2 g, 51 mL, 220 mmol) was charged into the reactor slowly over 1 h. An exotherm of about +3 to +5° C. was observed. The internal temperature was kept under 20±5° C. during the charge. Once the HCl charge was complete, the jacket temperature was ramped to 45° C. over 30 min. The solution was stirred at 45° C. for no less than (NLT) 3 h. Next, the jacket was ramped down from 45° C. to 25° C. over 1 h. The solution was polish-filtered (0.2 μm Polycap PTFE membrane filter via FMI pump), and rinsed forward with 1,4-dioxane (2×103 g). The solution was charged back into the reactor and the jacket temperature was set to 60° C. The solution was stripped down to 5 V under vacuum with the jacket at 60° C. Next, the jacket temperature was set to 10° C. With contents temperature stable at 10.4° C., ammonium hydroxide (35 mL) was added slowly into the reactor over 1 h. A +5 to +15° C. exotherm can be observed based on speed of addition. Contents temperature was kept under 25° C. The solution turned into an off-white slurry as the $NH_4OH$ addition proceeded. Ammonium hydroxide was added until the pH reached 8-9. Once addition was complete, the jacket was set to 5° C. and the slurry was aged for 16 h. The slurry was filtered on a "fine" fritted funnel. The wet cake was washed with $H_2O$ previously cooled to 5° C. (2×30 g). The solids were air-dried on the covered fritted funnel for 12 h, then under vacuum at 25° C. for 72 h to afford the title compound as a solid (7.22 g, 57%).

Example 12

Effect of pH on Solubility of $N^6$-((2-azidoethoxy)carbonyl)-L-lysine (Formula (VIa)) in Water To further purify $N^6$-((2-azidoethoxy)carbonyl)-L-lysine (Formula (VIa)), a suspension of $N^6$-((2-azidoethoxy)carbonyl)-L-lysine (Formula (VIa)) in water was prepared, followed by addition of HC1 to form a solution. Neutralization of the resulting solution with ammonium hydroxide reprecipitates the product and further purges the material of residual impurities, which remain in solution. In order to improve product yield, the effect of pH on the solubility of $N^6$-((2-azidoethoxy)carbonyl)-L-lysine (Formula (VIa)) was examined. Briefly, this study involved suspending $N^6$-((2-azidoethoxy)carbonyl)-L-lysine (Formula (VIa)) in water, progressively basifying the mixture, and determining the amount of $N^6$-((2-azidoethoxy)carbonyl)-L-lysine (Formula (VIa)) in the supernatant as a function of pH.

$N^6$-((2-azidoethoxy)carbonyl)-L-lysine (Formula (VIa)) (0.95 g) was charged into a 20 mL glass scintillation vial along with water (7.2 g). The resulting suspension was thoroughly mixed on a vortex apparatus for 60 seconds, then allowed to settle for 5 minutes. The pH of the supernatant was measured at 4.44 and an aliquot was taken and diluted with HPLC eluent ($H_2O$:$CH_3CN$ 1:1, 0.1% TFA). The sample was analyzed by HPLC (column: ACE Excel 3 Super C18, 4.6×150 mm, 3.0 μm, flow rate: 1.2 mL/min, phase A: 0.1% TFA in water, phase B: 0.1% TFA in acetonitrile) and the content of $N^6$-((2-azidoethoxy)carbonyl)-L-lysine (Formula (VIa)) was calculated based on HPLC analysis of Formula (VIa) standards.

The contents of the scintillation vial were basified by addition of a drop of 28-30% ammonium hydroxide, and the suspension was vortexed, allowed to decant, and the supernatant was again sampled and analyzed by HPLC. This basification/analysis procedure was repeated 5 more times, and the results are shown in Table 5.

TABLE 5

Effect of pH on Solubility of $N^6$-((2-azidoethoxy)carbonyl)-L-lysine (Formula (VIa)).

| Supernatant | pH | Amount of Formula (VIa) (mg) |
|---|---|---|
| 1 | 4.44 | 36 |
| 2 | 8.13 | 37 |
| 3 | 8.58 | 38 |
| 4 | 8.73 | 40 |
| 5 | 8.86 | 42 |
| 6 | 9.00 | 44 |
| 7 | 9.26 | 44 |

HPLC analysis shows that in a pH range from 4 to 8, a saturated aqueous solution of $N^6$-((2-azidoethoxy)carbonyl)-L-lysine (Formula (VIa)) contains roughly the same amount of product in its supernatant. Recovery of $N^6$-((2-azidoethoxy)carbonyl)-L-lysine (Formula (VIa)) can be achieved by precipitating the product at a pH range of 4 to 10, such as at a pH of about 7 to 8 or 8 to 9, or between about 8 and 8.5.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby. The disclosures of all patent and scientific literature cited herein are expressly incorporated herein in their entirety by reference. To the extent that any incorporated material is inconsistent with the express content of this disclosure, the express content controls.

The invention claimed is:

1. A method of preparing a compound of Formula (VI)

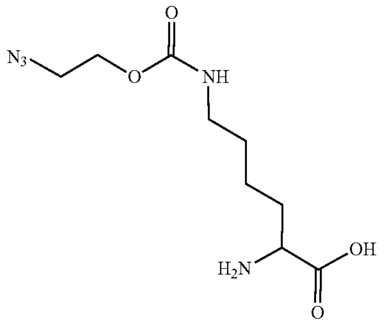

(VI)

or a salt thereof, comprising reacting a compound of Formula (III)

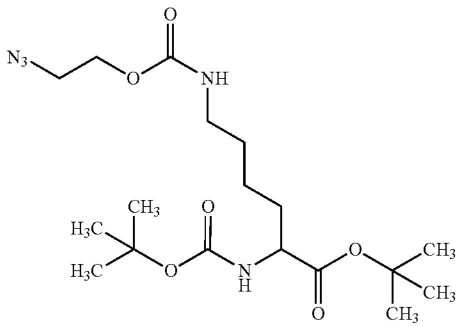

(III)

with an acid to afford the compound of Formula (VI) or a salt thereof.

2. The method of claim 1, wherein the acid is one or more of phosphoric acid, hydrochloric acid, acetic acid, and trifluoroacetic acid.

3. The method of claim 1, wherein the reaction of the compound of Formula (III) with the acid is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400, and polyethylene glycols.

4. The method of claim 1, wherein the method further comprises addition of a base.

5. The method of claim 4, wherein addition of the base provides a solution having a pH in a range from 4 to 10.

6. The method of claim 1, wherein the compound of Formula (VI) is a compound of Formula (VIa)

(VIa)

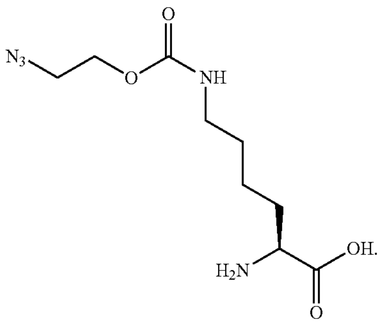

7. A method of preparing a compound of Formula (III)

(III)

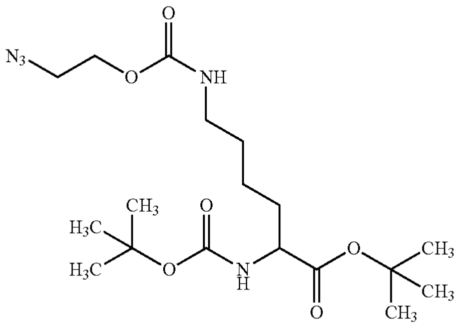

comprising reacting a compound of Formula (II)

(II)

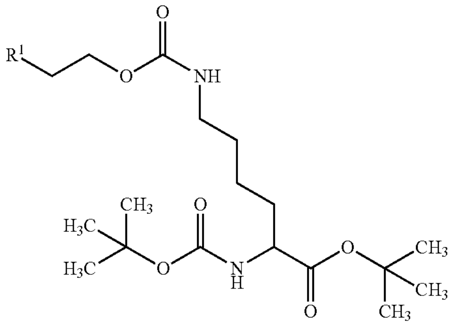

wherein $R^1$ is selected from chloro, bromo, and iodo, with an alkali azide salt to afford the compound of Formula (III).

8. The method of claim 7, wherein the alkali azide salt is selected from lithium azide, sodium azide, and potassium azide.

9. The method of claim 7, wherein the reaction of the compound of Formula (II) with the alkali azide salt is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400, and polyethylene glycols.

10. The method of claim 9, wherein the solution further comprises water.

11. The method of claim 7, wherein the compound of Formula (III) is a compound of Formula (IIIa)

(IIIa)

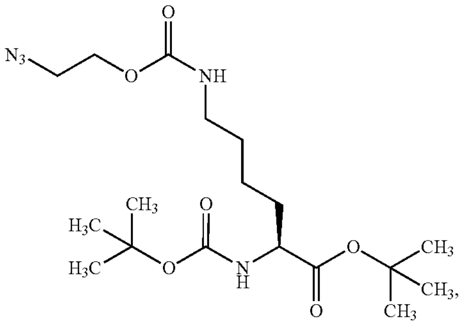

and the compound of Formula (II) is a compound of Formula (IIa)

(IIa)

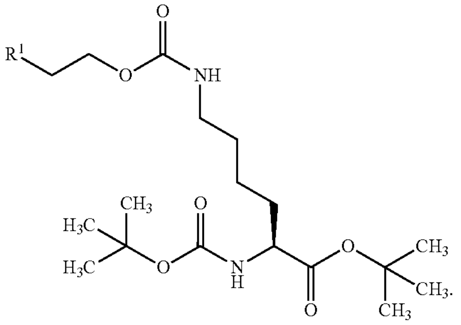

wherein $R^1$ is selected from chloro, bromo, and iodo.

12. A method of preparing a compound of Formula (II)

(II)

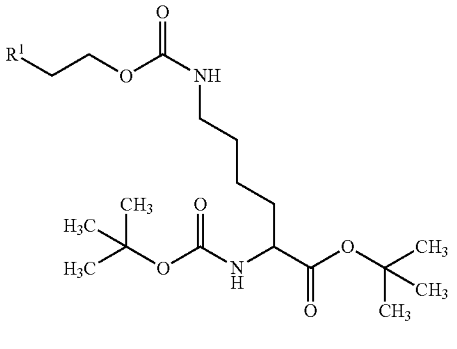

comprising reacting a compound of Formula (I)

(I)

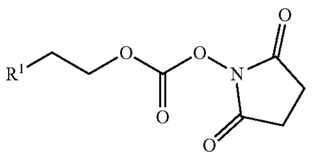

with a compound of Formula (V)

(V)

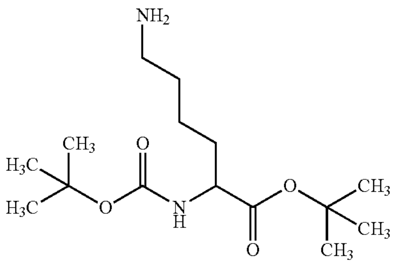

to afford the compound of Formula (II), wherein in each of the compounds of Formula (I) and Formula (II), $R^1$ is the same and is selected from chloro, bromo, and iodo.

13. The method of claim 12, wherein the reaction of the compound of Formula (V) with the compound of Formula (I) is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400, and polyethylene glycols.

14. The method of claim 12, wherein the compound of Formula (II) is a compound of Formula (IIa)

(IIa)

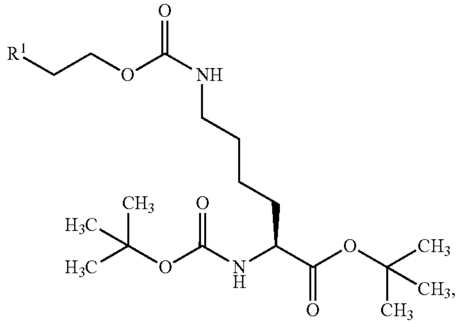

wherein $R^1$ is selected from chloro, bromo, and iodo, and the compound of Formula (V) is a compound of Formula (Va)

(Va)

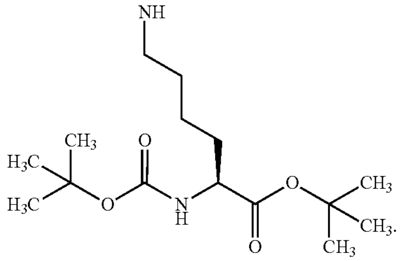

15. A method of preparing a compound of Formula (I)

(I)

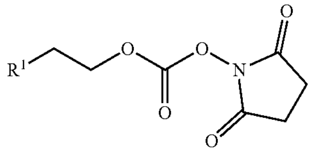

comprising reacting a compound of Formula (IV)

(IV)

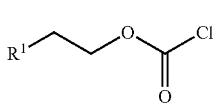

with N-hydroxysuccinimide to afford the compound of Formula (I), wherein in each of the compounds of Formula (I) and Formula (IV), $R^1$ is the same and is selected from chloro, bromo, and iodo.

16. The method of claim 15, wherein the reaction of the compound of Formula (IV) with N-hydroxysuccinimide is performed in a solution comprising an aprotic solvent selected from acetonitrile, acetone, methyl ethyl ketone, dichloromethane, chloroform, tetrahydrofuran, 2-methyltetrahydrofuran, N-methylpyrrolidine, dimethylsulfoxide, N,N-dimethylformamide, dimethylacetamide, 1,4-dioxane, sulfolane, gamma butyrolactone, pyrrolidones, 1-methyl-2-pyrrolidinone, methylpyrroline, ethylene glycol monomethyl ether, diethylene glycol monomethyl ether, PEG400, and polyethylene glycols.

17. The method of claim 16, wherein the solution further comprises a base.

18. A method of preparing a compound of Formula (VIa), or a salt thereof, comprising the following steps:

(i) reacting

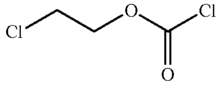

with

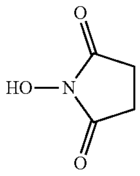

to form

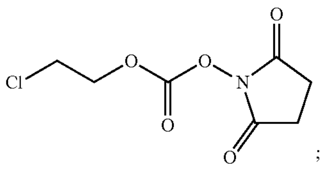 [SMILES: O=C(OCCCl)ON1C(=O)CCC1=O]

;

(ii) reacting

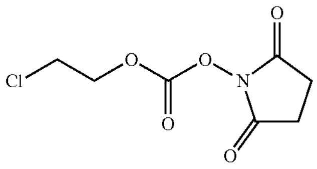 [SMILES: O=C(OCCCl)ON1C(=O)CCC1=O]

with (Va)

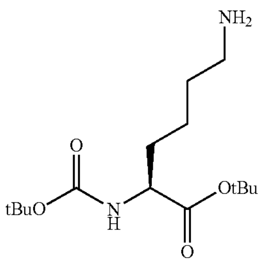

to form

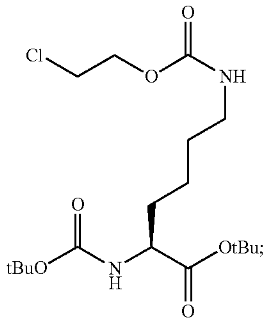 [SMILES: CC(C)(C)OC(=O)N[C@@H](CCCCNC(=O)OCCCl)C(=O)OC(C)(C)C]

(iii) reacting

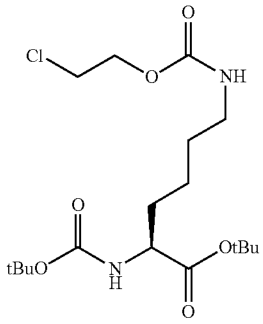 [SMILES: CC(C)(C)OC(=O)N[C@@H](CCCCNC(=O)OCCCl)C(=O)OC(C)(C)C]

with $NaN_3$ to form (IIIa)

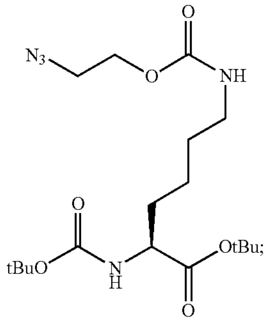

and (iv) reacting (IIIa)

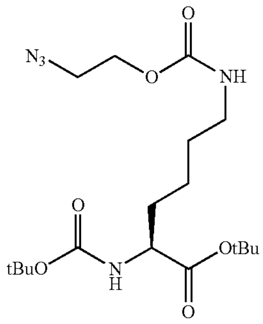

with HCl to form (VIa)

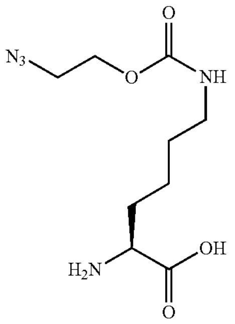

or a salt thereof.

19. A compound selected from:

a) a compound of Formula (I):

(I)

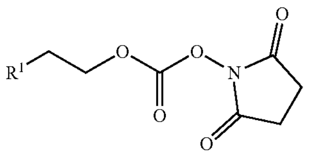

wherein $R^1$ is selected from chloro, bromo, and iodo;

b) a compound of Formula (II):

(II)

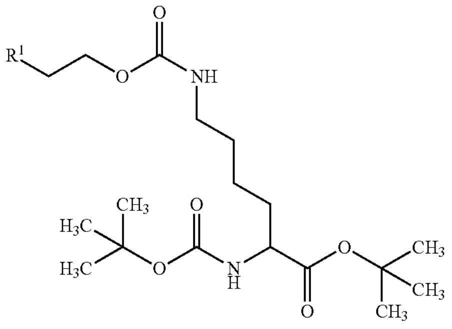

wherein $R^1$ is selected from chloro, bromo, and iodo;

c) a compound of Formula (III):

(III)

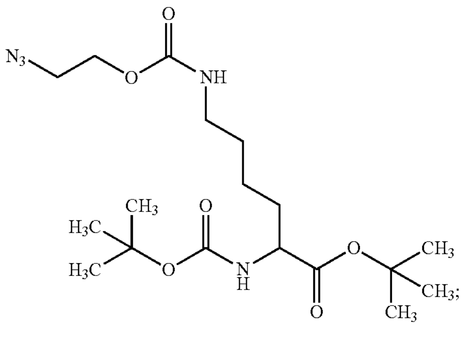

d) a compound of Formula (VII):

(VII)

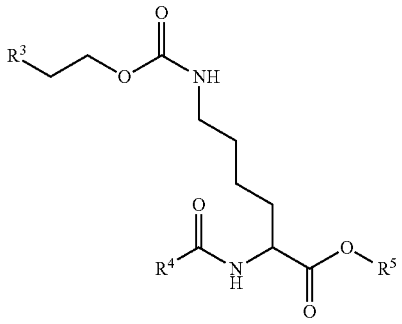

wherein:

$R^3$ is selected from chloro, bromo and iodo;

$R^4$ is selected from —$OR^6$, —$CF_3$, —$CH_2C_6$-$C_{12}$aryl, and $C_1$-$C_6$ alkyl;

$R^5$ is —$CH_2C_6$-$C_{12}$aryl or $C_1$-$C_6$ alkyl; and $R^6$ is selected from $C_1$-$C_6$ alkyl, $C_6$-$C_{12}$aryl, and —$CH_2C_6$-$C_{12}$ aryl; and e) a compound of Formula (VIII):

(VIII)

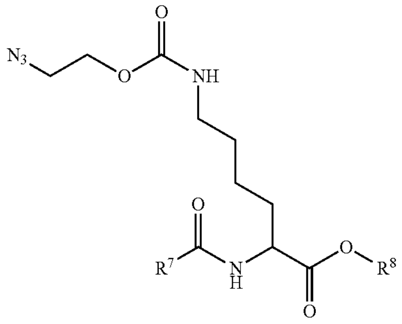

wherein:

$R^7$ is selected from —$OR^9$, —$CF_3$, —$CH_2C_6$-$C_{12}$aryl, and $C_1$-$C_6$ alkyl;

$R^8$ is —$CH_2C_6$-$C_{12}$aryl or $C_1$-$C_6$ alkyl; and $R^9$ is selected from $C_1$-$C_6$ alkyl, $C_6$-$C_{12}$aryl, and —$CH_2C_6$-$C_{12}$aryl.

20. The method of claim 3, wherein the aprotic solvent is selected from acetonitrile, tetrahydrofuran, N,N-dimethylformamide, and 1,4-dioxane.

21. The method of claim 4, wherein the base is one or more of ammonium hydroxide, sodium hydroxide, and potassium hydroxide.

22. The method of claim 4, wherein addition of the base provides a solution having a pH in a range from 8 to 9.

23. The method of claim 9, wherein the aprotic solvent is selected from acetonitrile, tetrahydrofuran, N,N-dimethylformamide, and 1,4-dioxane.

24. The method of claim 13, wherein the aprotic solvent is selected from 2-methyltetrahydrofuran, N,N-dimethylformamide, dichloromethane, chloroform, and tetrahydrofuran.

25. The method of claim 16, wherein the aprotic solvent is selected from tetrahydrofuran, dichloromethane, chloroform, acetonitrile, and 2-methyltetrahydrofuran.

26. The method of claim 17, wherein the base is a trialkylamine.

27. The compound of claim 19, wherein the compound is a compound of Formula (VII), wherein $R^3$ is chloro; $R^4$ is —$OR^6$; $R^5$ is $C_1$-$C_6$ alkyl; and $R^6$ is $C_1$-$C_6$ alkyl.

28. The compound of claim 27, wherein $R^5$ and $R^6$ are each tert-butyl.

29. The compound of claim 19, wherein the compound is a compound of Formula (VIII), wherein $R^7$ is —$OR^9$; $R^8$ is $C_1$-$C_6$ alkyl; and $R^9$ is $C_1$-$C_6$ alkyl.

30. The compound of claim 29, wherein $R^8$ and $R^9$ are each tert-butyl.

* * * * *